United States Patent
Boock et al.

(10) Patent No.: US 12,409,515 B2
(45) Date of Patent: Sep. 9, 2025

(54) CONTINUOUS ANALYTE SENSORS AND METHODS OF MAKING SAME

(71) Applicant: DexCom, Inc., San Diego, CA (US)

(72) Inventors: Robert Boock, Carlsbad, CA (US); Jeff Jackson, Poway, CA (US); Huashi Zhang, San Diego, CA (US); Jason Mitchell, Poway, CA (US)

(73) Assignee: DEXCOM, INC., San Diego, CA (US)

( * ) Notice: Subject to any disclaimer, the term of this patent is extended or adjusted under 35 U.S.C. 154(b) by 424 days.

(21) Appl. No.: 17/867,608

(22) Filed: Jul. 18, 2022

(65) Prior Publication Data
US 2022/0346674 A1     Nov. 3, 2022

Related U.S. Application Data

(63) Continuation of application No. 16/452,364, filed on Jun. 25, 2019, now abandoned, which is a (Continued)

(51) Int. Cl.
*B23K 26/362* (2014.01)
*A61B 5/145* (2006.01)
(Continued)

(52) U.S. Cl.
CPC ........ *B23K 26/362* (2013.01); *A61B 5/14503* (2013.01); *A61B 5/1451* (2013.01);
(Continued)

(58) Field of Classification Search
None
See application file for complete search history.

(56) References Cited

U.S. PATENT DOCUMENTS

| 65,604 A | 6/1867 | Reynolds |
| 1,966,575 A | 7/1934 | Whiting |

(Continued)

FOREIGN PATENT DOCUMENTS

| EP | 0127958 A2 | 12/1984 |
| EP | 0351892 A2 | 1/1990 |

(Continued)

OTHER PUBLICATIONS

US 7,530,950 B2, 05/2009, Brister et al. (withdrawn)
(Continued)

*Primary Examiner* — Jiong-Ping Lu
(74) *Attorney, Agent, or Firm* — Christopher J. Knors; Moore & Van Allen PLLC

(57) ABSTRACT

Described here are embodiments of processes and systems for the continuous manufacturing of implantable continuous analyte sensors. In some embodiments, a method is provided for sequentially advancing an elongated conductive body through a plurality of stations, each configured to treat the elongated conductive body. In some of these embodiments, one or more of the stations is configured to coat the elongated conductive body using a meniscus coating process, whereby a solution formed of a polymer and a solvent is prepared, the solution is continuously circulated to provide a meniscus on a top portion of a vessel holding the solution, and the elongated conductive body is advanced through the meniscus. The method may also comprise the step of removing excess coating material from the elongated conductive body by advancing the elongated conductive body through a die orifice. For example, a provided elongated conductive body 510 is advanced through a pre-coating treatment station 520, through a coating station 530, through a thickness control station 540, through a drying or (Continued)

curing station 550, through a thickness measurement station 560, and through a post-coating treatment station 570.

19 Claims, 24 Drawing Sheets

Related U.S. Application Data continuation of application No. 12/829,337, filed on Jul. 1, 2010, now abandoned.

(60) Provisional application No. 61/222,716, filed on Jul. 2, 2009, provisional application No. 61/222,815, filed on Jul. 2, 2009, provisional application No. 61/222,751, filed on Jul. 2, 2009.

(51) Int. Cl.
*A61B 5/1473* (2006.01)
*A61B 5/1486* (2006.01)
*B05C 3/02* (2006.01)
*B05C 3/10* (2006.01)
*B05C 3/12* (2006.01)
B05C 5/02 (2006.01)
B05D 1/18 (2006.01)
B05D 3/06 (2006.01)
B23K 26/08 (2014.01)
C23C 2/00 (2006.01)

(52) U.S. Cl.
CPC ...... *A61B 5/14517* (2013.01); *A61B 5/14532* (2013.01); *A61B 5/14546* (2013.01); *A61B 5/1473* (2013.01); *A61B 5/14865* (2013.01); *B05C 3/02* (2013.01); *B05C 3/10* (2013.01); *B05C 3/125* (2013.01); A61B 2560/0223 (2013.01); A61B 2562/0209 (2013.01); A61B 2562/043 (2013.01); A61B 2562/125 (2013.01); B05C 5/0241 (2013.01); B05D 1/18 (2013.01); B05D 3/06 (2013.01); B23K 26/0823 (2013.01); B29C 2791/009 (2013.01); C23C 2/00 (2013.01)

(56) References Cited

U.S. PATENT DOCUMENTS

| | | |
|---|---|---|
| 2,447,531 A | 8/1948 | Pierce |
| 2,489,456 A | 11/1949 | Liebel |
| 2,497,894 A | 2/1950 | Clare et al. |
| 2,728,831 A | 12/1955 | Pope |
| 2,889,239 A | 6/1959 | Meissner |
| 3,499,828 A | 3/1970 | Vittorio et al. |
| 3,599,600 A | 8/1971 | Carleton et al. |
| 3,608,294 A | 9/1971 | Donaldson et al. |
| 3,658,571 A | 4/1972 | Marzocchi |
| 3,930,462 A | 1/1976 | Day |
| 3,933,593 A | 1/1976 | Sternberg |
| 4,126,510 A | 11/1978 | Moscony et al. |
| 4,225,410 A | 9/1980 | Pace |
| 4,292,423 A | 9/1981 | Kaufmann et al. |
| 4,422,583 A | 12/1983 | Maxner et al. |
| 4,644,898 A | 2/1987 | Jochem et al. |
| 4,726,381 A | 2/1988 | Jones |
| 4,736,748 A | 4/1988 | Nakamura et al. |
| 4,763,658 A | 8/1988 | Jones |
| 4,777,205 A | 10/1988 | La Scola et al. |
| 4,826,706 A | 5/1989 | Hilker et al. |
| 4,832,034 A | 5/1989 | Pizziconi et al. |
| 4,848,348 A | 7/1989 | Craighead |
| 4,886,562 A | 12/1989 | Pinson |
| 4,890,621 A | 1/1990 | Hakky |
| 4,935,345 A | 6/1990 | Guilbeau et al. |
| 4,973,320 A | 11/1990 | Brenner et al. |
| 4,979,509 A | 12/1990 | Hakky |
| 5,063,081 A | 11/1991 | Cozzette et al. |
| 5,147,725 A | 9/1992 | Pinchuk |
| 5,165,407 A | 11/1992 | Wilson et al. |
| 5,200,051 A | 4/1993 | Cozzette et al. |
| 5,212,050 A | 5/1993 | Mier et al. |
| 5,248,249 A | 9/1993 | Yamamoto et al. |
| 5,269,891 A | 12/1993 | Colin |
| 5,270,079 A | 12/1993 | Bok |
| 5,310,469 A | 5/1994 | Cunningham et al. |
| 5,312,590 A | 5/1994 | Gunasingham |
| 5,372,293 A | 12/1994 | Corlay et al. |
| 5,380,422 A | 1/1995 | Negishi et al. |
| 5,466,575 A | 11/1995 | Cozzette et al. |
| 5,497,772 A | 3/1996 | Schulman et al. |
| 5,524,338 A | 6/1996 | Martyniuk et al. |
| 5,554,339 A | 9/1996 | Cozzette et al. |
| 5,565,143 A | 10/1996 | Chan |
| 5,640,954 A | 6/1997 | Pfeiffer et al. |
| 5,660,163 A | 8/1997 | Schulman et al. |
| 5,662,969 A | 9/1997 | Ling |
| 5,665,222 A | 9/1997 | Heller et al. |
| 5,682,884 A | 11/1997 | Hill et al. |
| 5,683,514 A | 11/1997 | Cox et al. |
| 5,772,903 A | 6/1998 | Hirsch |
| 5,773,270 A | 6/1998 | D'Orazio et al. |
| 5,791,344 A | 8/1998 | Schulman et al. |
| 5,837,454 A | 11/1998 | Cozzette et al. |
| 5,879,828 A | 3/1999 | Debe et al. |
| 5,928,155 A | 7/1999 | Eggers et al. |
| 5,928,571 A | 7/1999 | Chan |
| 5,931,814 A | 8/1999 | Alex et al. |
| 6,063,637 A | 5/2000 | Arnold et al. |
| 6,103,033 A | 8/2000 | Say et al. |
| 6,106,486 A | 8/2000 | Tenerz et al. |
| 6,134,461 A | 10/2000 | Say et al. |
| 6,175,752 B1 | 1/2001 | Say et al. |
| 6,187,378 B1 | 2/2001 | Doncsecz |
| 6,214,115 B1 | 4/2001 | Taylor et al. |
| 6,248,067 B1 | 6/2001 | Causey, III et al. |
| 6,275,717 B1 | 8/2001 | Gross et al. |
| 6,299,583 B1 | 10/2001 | Eggers et al. |
| 6,306,594 B1 | 10/2001 | Cozzette et al. |
| 6,341,232 B1 | 1/2002 | Conn et al. |
| 6,360,888 B1 | 3/2002 | McIvor et al. |
| 6,368,658 B1 | 4/2002 | Schwarz et al. |
| 6,393,318 B1 | 5/2002 | Conn et al. |
| 6,398,562 B1 | 6/2002 | Butler et al. |
| 6,407,195 B2 | 6/2002 | Sherman et al. |
| 6,413,393 B1 | 7/2002 | Van Antwerp et al. |
| 6,424,847 B1 | 7/2002 | Mastrototaro et al. |
| 6,438,414 B1 | 8/2002 | Conn et al. |
| 6,442,413 B1 | 8/2002 | Silver |
| 6,461,496 B1 | 10/2002 | Feldman et al. |
| 6,484,045 B1 | 11/2002 | Holker et al. |
| 6,484,046 B1 | 11/2002 | Say et al. |
| 6,520,326 B2 | 2/2003 | McIvor et al. |
| 6,558,320 B1 | 5/2003 | Causey, III et al. |
| 6,558,321 B1 | 5/2003 | Burd et al. |
| 6,561,978 B1 | 5/2003 | Conn et al. |
| 6,565,509 B1 | 5/2003 | Say et al. |
| 6,579,690 B1 | 6/2003 | Bonnecaze et al. |
| 6,592,745 B1 | 7/2003 | Feldman et al. |
| 6,613,379 B2 | 9/2003 | Ward et al. |
| 6,618,934 B1 | 9/2003 | Feldman et al. |
| 6,641,533 B2 | 11/2003 | Causey, III et al. |
| 6,650,471 B2 | 11/2003 | Doi |
| 6,654,625 B1 | 11/2003 | Say et al. |
| 6,740,214 B1 | 5/2004 | Dobson et al. |
| 6,801,041 B2 | 10/2004 | Karinka et al. |
| 6,809,653 B1 | 10/2004 | Mann et al. |
| 6,892,085 B2 | 5/2005 | McIvor et al. |
| 6,895,263 B2 | 5/2005 | Shin et al. |
| 6,895,265 B2 | 5/2005 | Silver |
| 6,965,791 B1 | 11/2005 | Hitchcock et al. |
| 6,973,706 B2 | 12/2005 | Say et al. |
| 6,975,893 B2 | 12/2005 | Say et al. |
| 6,989,891 B2 | 1/2006 | Braig et al. |
| 6,990,366 B2 | 1/2006 | Say et al. |

(56) References Cited

U.S. PATENT DOCUMENTS

| | | |
|---|---|---|
| 6,998,247 B2 | 2/2006 | Monfre et al. |
| 7,003,336 B2 | 2/2006 | Holker et al. |
| 7,003,341 B2 | 2/2006 | Say et al. |
| 7,033,322 B2 | 4/2006 | Silver |
| 7,061,593 B2 | 6/2006 | Braig et al. |
| 7,098,803 B2 | 8/2006 | Mann et al. |
| 7,163,511 B2 | 1/2007 | Conn et al. |
| 7,190,988 B2 | 3/2007 | Say et al. |
| 7,241,586 B2 | 7/2007 | Gulati et al. |
| 7,310,544 B2 | 12/2007 | Brister et al. |
| 7,366,566 B2 | 4/2008 | Henry et al. |
| 7,367,942 B2 | 5/2008 | Grage et al. |
| 7,381,184 B2 | 6/2008 | Funderburk et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,613,491 B2 | 11/2009 | Boock et al. |
| 7,615,007 B2 | 11/2009 | Shults et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,771,352 B2 | 8/2010 | Shults et al. |
| 7,857,760 B2 | 12/2010 | Brister et al. |
| 7,927,274 B2 | 4/2011 | Rasdal et al. |
| 7,949,381 B2 | 5/2011 | Brister et al. |
| 2001/0008187 A1 | 7/2001 | Hanssen et al. |
| 2002/0023852 A1 | 2/2002 | McIvor et al. |
| 2002/0084196 A1 | 7/2002 | Liamos et al. |
| 2002/0128546 A1 | 9/2002 | Silver |
| 2003/0009093 A1 | 1/2003 | Silver |
| 2003/0078481 A1 | 4/2003 | McIvor et al. |
| 2003/0088166 A1 | 5/2003 | Say et al. |
| 2003/0100040 A1 | 5/2003 | Bonnecaze et al. |
| 2003/0100821 A1 | 5/2003 | Heller et al. |
| 2003/0125613 A1 | 7/2003 | Enegren et al. |
| 2003/0187338 A1 | 10/2003 | Say et al. |
| 2003/0188427 A1 | 10/2003 | Say et al. |
| 2003/0188965 A1 | 10/2003 | King et al. |
| 2003/0199744 A1 | 10/2003 | Buse et al. |
| 2004/0010207 A1 | 1/2004 | Flaherty et al. |
| 2004/0039298 A1 | 2/2004 | Abreu |
| 2004/0074785 A1 | 4/2004 | Holker et al. |
| 2004/0078219 A1 | 4/2004 | Kaylor et al. |
| 2004/0106859 A1 | 6/2004 | Say et al. |
| 2004/0133164 A1 | 7/2004 | Funderburk et al. |
| 2004/0152187 A1 | 8/2004 | Haight et al. |
| 2004/0167801 A1 | 8/2004 | Say et al. |
| 2004/0176672 A1 | 9/2004 | Silver et al. |
| 2004/0236200 A1 | 11/2004 | Say et al. |
| 2004/0258915 A1 | 12/2004 | Hasui et al. |
| 2005/0028731 A1 | 2/2005 | Lindholm |
| 2005/0065464 A1 | 3/2005 | Talbot et al. |
| 2005/0121322 A1 | 6/2005 | Say et al. |
| 2005/0136500 A1 | 6/2005 | Yang et al. |
| 2005/0153379 A1 | 7/2005 | Hoon et al. |
| 2005/0173245 A1 | 8/2005 | Feldman et al. |
| 2005/0192557 A1 | 9/2005 | Brauker et al. |
| 2005/0196974 A1 | 9/2005 | Weigel et al. |
| 2005/0197554 A1 | 9/2005 | Polcha |
| 2005/0215871 A1 | 9/2005 | Feldman et al. |
| 2005/0239154 A1 | 10/2005 | Feldman et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0272989 A1 | 12/2005 | Shah et al. |
| 2005/0288596 A1 | 12/2005 | Eigler et al. |
| 2006/0001550 A1 | 1/2006 | Mann et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020188 A1 | 1/2006 | Kamath et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0052745 A1 | 3/2006 | Van Antwerp et al. |
| 2006/0079740 A1 | 4/2006 | Silver et al. |
| 2006/0118415 A1 | 6/2006 | Say et al. |
| 2006/0127562 A1 | 6/2006 | Lewis et al. |
| 2006/0142651 A1 | 6/2006 | Brister et al. |
| 2006/0155180 A1 | 7/2006 | Brister et al. |
| 2006/0163744 A1 | 7/2006 | Vanheusden et al. |
| 2006/0183178 A1 | 8/2006 | Gulati et al. |
| 2006/0183984 A1 | 8/2006 | Dobbles et al. |
| 2006/0189863 A1 | 8/2006 | Peyser et al. |
| 2006/0195029 A1 | 8/2006 | Shults et al. |
| 2006/0200020 A1 | 9/2006 | Brister et al. |
| 2006/0200970 A1 | 9/2006 | Brister et al. |
| 2006/0222566 A1 | 10/2006 | Brauker et al. |
| 2006/0235285 A1 | 10/2006 | Brister et al. |
| 2006/0253085 A1 | 11/2006 | Geismar et al. |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0258929 A1 | 11/2006 | Goode et al. |
| 2006/0270922 A1 | 11/2006 | Brauker et al. |
| 2006/0270923 A1 | 11/2006 | Brauker et al. |
| 2006/0293576 A1 | 12/2006 | Van et al. |
| 2007/0016381 A1 | 1/2007 | Kamath et al. |
| 2007/0027370 A1 | 2/2007 | Brauker et al. |
| 2007/0027385 A1 | 2/2007 | Brister et al. |
| 2007/0032706 A1 | 2/2007 | Kamath et al. |
| 2007/0038044 A1 | 2/2007 | Dobbles et al. |
| 2007/0045902 A1 | 3/2007 | Brauker et al. |
| 2007/0059196 A1 | 3/2007 | Brister et al. |
| 2007/0066873 A1 | 3/2007 | Kamath et al. |
| 2007/0084560 A1 | 4/2007 | Fuentes |
| 2007/0135698 A1 | 6/2007 | Shah et al. |
| 2007/0141245 A1 | 6/2007 | Tsai |
| 2007/0155851 A1 | 7/2007 | Alli et al. |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0179436 A1 | 8/2007 | Braig et al. |
| 2007/0197889 A1 | 8/2007 | Brister et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0227633 A1 | 10/2007 | Basol |
| 2007/0227907 A1 | 10/2007 | Shah et al. |
| 2007/0232879 A1 | 10/2007 | Brister et al. |
| 2008/0033254 A1 | 2/2008 | Kamath et al. |
| 2008/0033260 A1 | 2/2008 | Sheppard et al. |
| 2008/0083617 A1* | 4/2008 | Simpson ............... A61B 5/1486 204/403.01 |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0091094 A1 | 4/2008 | Heller et al. |
| 2008/0091095 A1 | 4/2008 | Heller et al. |
| 2008/0108942 A1 | 5/2008 | Brister et al. |
| 2008/0115727 A1 | 5/2008 | Otis et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0188731 A1 | 8/2008 | Brister et al. |
| 2008/0194935 A1 | 8/2008 | Brister et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0214915 A1 | 9/2008 | Brister et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |

(56) References Cited

U.S. PATENT DOCUMENTS

| | | |
|---|---|---|
| 2008/0287765 A1 | 11/2008 | Rasdal et al. |
| 2008/0296155 A1 | 12/2008 | Shults et al. |
| 2008/0306435 A1 | 12/2008 | Kamath et al. |
| 2008/0306444 A1 | 12/2008 | Brister et al. |
| 2009/0018424 A1 | 1/2009 | Kamath et al. |
| 2009/0030294 A1 | 1/2009 | Petisce et al. |
| 2009/0036763 A1 | 2/2009 | Brauker et al. |
| 2009/0062633 A1 | 3/2009 | Brauker et al. |
| 2009/0076360 A1 | 3/2009 | Brister et al. |
| 2009/0076361 A1 | 3/2009 | Kamath et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156924 A1 | 6/2009 | Shariati et al. |
| 2011/0024043 A1 | 2/2011 | Boock et al. |
| 2011/0027453 A1 | 2/2011 | Boock et al. |
| 2011/0027458 A1 | 2/2011 | Boock et al. |
| 2012/0138871 A1 | 6/2012 | Dorfman et al. |
| 2013/0245412 A1 | 9/2013 | Rong et al. |
| 2014/0123893 A1 | 5/2014 | Boock et al. |
| 2014/0343386 A1 | 11/2014 | Boock et al. |
| 2019/0307371 A1 | 10/2019 | Boock et al. |

FOREIGN PATENT DOCUMENTS

| | | |
|---|---|---|
| EP | 0351891 B1 | 9/1993 |
| EP | 0747069 A2 | 12/1996 |
| EP | 0885932 A2 | 12/1998 |
| EP | 1092764 A2 | 4/2001 |
| EP | 1153571 A1 | 11/2001 |
| EP | 0856064 B1 | 6/2002 |
| EP | 1266607 A2 | 12/2002 |
| EP | 1413245 A2 | 4/2004 |
| EP | 0717838 B1 | 5/2004 |
| EP | 1504113 B1 | 11/2006 |
| EP | 1522255 B1 | 5/2008 |
| EP | 2223710 A1 | 9/2010 |
| EP | 2226086 A1 | 9/2010 |
| JP | 2003297163 A | 10/2003 |
| WO | 9005910 A1 | 5/1990 |
| WO | 9010861 A1 | 9/1990 |
| WO | 9013021 A1 | 11/1990 |
| WO | 9201928 A1 | 2/1992 |
| WO | 9313408 A1 | 7/1993 |
| WO | 9314693 A1 | 8/1993 |
| WO | 9404241 A2 | 3/1994 |
| WO | 9408236 A1 | 4/1994 |
| WO | 9513838 A1 | 5/1995 |
| WO | 9522597 A1 | 8/1995 |
| WO | 9625089 A1 | 8/1996 |
| WO | 9701986 A1 | 1/1997 |
| WO | 9803431 A1 | 1/1998 |
| WO | 9811884 A1 | 3/1998 |
| WO | 9824358 A2 | 6/1998 |
| WO | 9956613 A1 | 11/1999 |
| WO | 0012720 A2 | 3/2000 |
| WO | 0019887 A1 | 4/2000 |
| WO | 0020626 A1 | 4/2000 |
| WO | 0032098 A1 | 6/2000 |
| WO | 0033065 A1 | 6/2000 |
| WO | 0045696 A1 | 8/2000 |
| WO | 0049940 A2 | 8/2000 |
| WO | 0049941 A1 | 8/2000 |
| WO | 0078210 A1 | 12/2000 |
| WO | 0078992 A2 | 12/2000 |
| WO | 0133216 A1 | 5/2001 |
| WO | 0134243 A1 | 5/2001 |
| WO | 0152727 A1 | 7/2001 |
| WO | 0158348 A2 | 8/2001 |
| WO | 0173109 A2 | 10/2001 |
| WO | 0188534 A2 | 11/2001 |
| WO | 0202755 A2 | 1/2002 |
| WO | 02058537 A2 | 8/2002 |
| WO | 02062210 A1 | 8/2002 |
| WO | 02082989 A1 | 10/2002 |
| WO | 03072269 A1 | 9/2003 |
| WO | 03074107 A2 | 9/2003 |
| WO | 03076937 A2 | 9/2003 |
| WO | 03082091 A2 | 10/2003 |
| WO | 03094714 A1 | 11/2003 |
| WO | 03097866 A1 | 11/2003 |
| WO | 03098165 A1 | 11/2003 |
| WO | 2004028337 A2 | 4/2004 |
| WO | 2004036183 A2 | 4/2004 |
| WO | 2004098685 A1 | 11/2004 |
| WO | 2004113901 A1 | 12/2004 |
| WO | 2004113912 A1 | 12/2004 |
| WO | 2005001462 A1 | 1/2005 |
| WO | 2005011489 A1 | 2/2005 |
| WO | 2005020797 A2 | 3/2005 |
| WO | 2005026689 A2 | 3/2005 |
| WO | 2005026690 A2 | 3/2005 |
| WO | 2005041766 A1 | 5/2005 |
| WO | 2005048834 A1 | 6/2005 |
| WO | 2005065542 A2 | 7/2005 |
| WO | 2005078424 A1 | 8/2005 |
| WO | 2005026689 A9 | 10/2005 |
| WO | 2005121355 A1 | 12/2005 |
| WO | 2005121785 A2 | 12/2005 |
| WO | 2006001029 A2 | 1/2006 |
| WO | 2006001929 A1 | 1/2006 |
| WO | 2006017358 A1 | 2/2006 |
| WO | 2006019623 A2 | 2/2006 |
| WO | 2006019665 A1 | 2/2006 |
| WO | 2006029293 A1 | 3/2006 |
| WO | 2006063735 A1 | 6/2006 |
| WO | 2006063736 A1 | 6/2006 |
| WO | 2006076412 A1 | 7/2006 |
| WO | 2006086423 A2 | 8/2006 |
| WO | 2006088576 A2 | 8/2006 |
| WO | 2006108811 A1 | 10/2006 |
| WO | 2006119887 A1 | 11/2006 |
| WO | 2006122048 A1 | 11/2006 |
| WO | 2006122533 A1 | 11/2006 |
| WO | 2006122553 A1 | 11/2006 |
| WO | 2006133171 A2 | 12/2006 |
| WO | 2007005170 A2 | 1/2007 |
| WO | 2007028271 A2 | 3/2007 |
| WO | 2007033007 A1 | 3/2007 |
| WO | 2007053497 A2 | 5/2007 |
| WO | 2007053832 A2 | 5/2007 |
| WO | 2007056638 A2 | 5/2007 |
| WO | 2007070486 A2 | 6/2007 |
| WO | 2007079015 A2 | 7/2007 |
| WO | 2007086997 A2 | 8/2007 |
| WO | 2007097754 A1 | 8/2007 |
| WO | 2007114943 A2 | 10/2007 |
| WO | 2007126920 A1 | 11/2007 |
| WO | 2008001091 A1 | 1/2008 |
| WO | 2008013849 A2 | 1/2008 |
| WO | 2008016501 A2 | 2/2008 |
| WO | 2008021913 A2 | 2/2008 |
| WO | 2008048452 A2 | 4/2008 |
| WO | 2008048709 A1 | 4/2008 |
| WO | 2008051407 A2 | 5/2008 |
| WO | 2008052199 A2 | 5/2008 |
| WO | 2008067314 A2 | 6/2008 |
| WO | 2008076868 A2 | 6/2008 |
| WO | 2008083179 A2 | 7/2008 |
| WO | 2008086541 A2 | 7/2008 |
| WO | 2008094249 A1 | 8/2008 |
| WO | 2007079015 A9 | 10/2008 |
| WO | 2008134561 A1 | 11/2008 |
| WO | 2008134587 A1 | 11/2008 |
| WO | 2008150633 A2 | 12/2008 |

(56) References Cited

FOREIGN PATENT DOCUMENTS

| WO | 2008150917 A1 | 12/2008 | | |
|---|---|---|---|---|
| WO | WO2010027712 | * | 11/2010 | ........... H01L 21/027 |

OTHER PUBLICATIONS

Abel, et al., "Biosensors for in Vivo Glucose Measurements: Can We Cross the Experimental Stage," Biosensors & Bioelectronics, 2002, vol. 17, pp. 1059-1070.
Atanasov P., et al., "Implantation of a Refillable Glucose Monitoring-Telemetry Device," Biosensors and Bioelectronics, vol. 12 (7), 1997, pp. 669-680.
Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.
Chen M., et al., "A Novel Drug-Eluting Stent Spray-Coated with Multi-Layers of Collagen and Sirolimus," J. Controlled Release, vol. 108, 2005, pp. 178-189.
Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.
Currie J.F., et al., "Novel Non-Intrusive Trans-Dermal Remote Wireless Micro-Fluidic Monitoring System Applied to Continuous Glucose and Lactate Assays for Casualty Care and Combat Readiness Assessment," RTO HFM Symposium, RTO-MP-HFM-109, Aug. 16-18, 2004, pp. '24-1' - '24-18'.
Dassau E., et al., "In Silico Evaluation Platform for Artificial Pancreatic β-Cell Development—A Dynamic Simulator for Closed-Loop Control with Hardware-in-the-loop," Diabetes Technology & Therapeutics, vol. 11 (3), 2009, pp. 1-8.
Davies M.L., et al., "Polymer Membranes in Clinical Sensor Applications," An overview of membrane function, Biomaterials, vol. 13 (14), 1992, pp. 971-978.
Decher G., et al., "Buildup of Ultrathin Multilayer Films by a Self-Assembly Process: III. Consecutively Alternating Adsorption of Anionic and Cationic Polyelectrolytes on Charged Surfaces," Thin Solid Films, vol. 210/211, 1992, pp. 831-835.
Frohnauer M.K., et al., "Graphical Human Insulin Time-Activity Profiles Using Standardized Definitions," Diabetes Technology & Therapeutics, vol. 3 (3), 2001, pp. 419-429.
Gough D.A., "The implantable Glucose Sensor: An Example of Bioengineering Design," Introduction to Bioengineering, 2001, Chapter 3, pp. 57-66.
Gross T.M., et al., "Performance Evaluation of the Minimed® Continuous Glucose Monitoring System During Patient Home Use," Diabetes Technology & Therapeutics, vol. 2(1), 2000, pp. 49-56.
Hamilton, "Complete Guide to Selecting the Right Hamilton Gastight, Microliter, and Specialty Syringe for your Application," Syringe Selection, www.hamiltoncompany.com 2006, 20 pages.
Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.
Hunter I., et al., "Minimally Invasive Glucose Sensor and Insulin Delivery System," MIT Home Automation and Healthcare Consortium, Mar. 31, 2000, Progress Report No. 25, 17 pages.
International Preliminary Report on Patentability for Application No. PCT/US2010/040839 mailed Jan. 4, 2012, 5 pages.
International Search Report and Written Opinion for Application No. PCT/US2010/040839 mailed Feb. 10, 2011, 10 pages.
Jaffari S.A., et al., "Recent Advances in Amperometric Glucose Biosensors for In Vivo Monitoring," Physiological Measurement, 1995, vol. 16, pp. 1-15.

Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.
Kunzler J F., et al., "Contact Lens Materials," Chemistry & Industry, Aug. 21, 1995, pp. 651-655.
Kurtz T.W., et al., "Recommendations for Blood Pressure Measurement in Humans and Experimental Animals, Part 2: Blood Pressure Measurement In Experimental Animals: A Statement for Professionals From the Subcommittee of Professional and Public Education of the American Heart Association Council on High Blood Pressure Research," Hypertension, Feb. 2005, vol. 45, pp. 299-310.
Loffler P., et al., "Separation and Determination of Traces of Ammonia in Air by Means of Chromatomembrane Cells," Fresenius Journal of Analytical Chemistry, 1995, vol. 352, pp. 613-614.
Mancy K.H., et al., "A Galvanic Cell Oxygen Analyzer," Journal of Electroanalytical Chemistry, vol. 4, 1962, pp. 65-92.
Martin R.F., "General Deming Regression for Estimating Systematic Bias and its Confidence Interval in Method-Comparison Studies," Clinical Chemistry, vol. 46 (1), 2000, pp. 100-104.
Mastrototaro J.J., et al., "An Electroenzymatic Glucose Sensor Fabricated on a Flexible Substrate," Sensors and Actuators B, vol. 5, 1991, pp. 139-144.
Metzger M., et al., "Reproducibility of Glucose Measurements using the Glucose Sensor," Diabetes Care, vol. 25 (6), Jul. 2002, pp. 1185-1191.
Murphy S.M., et al., "Polymer Membranes in Clinical Sensor Applications, II. The Design and Fabrication of Permselective Hydrogels for Electrochemical Devices," Biomaterials, 1992, vol. 13 (14), pp. 979-990.
Quinn C.A.P., et al., "Biocompatible, Glucose-Permeable Hydrogel for In situ Coating of Implantable Biosensors," Biomaterials, vol. 18 (24), 1997, pp. 1665-1670.
Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.
Ramdane, "Thickening Factor in Marangoni Coating," Langmuir (1997), vol. 13, pp. 2911-2916.
Rebrin K., et al., "Subcutaneous Glucose Monitoring by Means of Electrochemical Sensors: Fiction or Reality?," Journal of Biomedical Engineering, vol. 14, Jan. 1992, pp. 33-40.
Selam J.L., "Management of Diabetes with Glucose Sensors and Implantable Insulin Pumps," From the Dream of the 60s to the Realities of the 90s, ASAIO Journal 1997, vol. 43, pp. 137-142.
Thompson M., et al., "In Vivo Probes: Problems and Perspectives," Clinical Biochemistry, vol. 19 (5), Oct. 1986, pp. 255-261.
Torjman M.C., et al., "Glucose Monitoring in Acute Care: Technologies on the Horizon," Journal of Diabetes Science and Technology, vol. 2 (2), Mar. 2008, pp. 178-181.
Updike S.J., et al., "Continuous Glucose Monitor Based on an Immobilized Enzyme Electrode Detector," Journal of Laboratory and Clinical Medicine, vol. 93(4), 1979, pp. 518-527.
Updike S.J., et al., "Laboratory Evaluation of New Reusable Blood Glucose Sensor," Diabetes Care, vol. 11 (10), Nov.-Dec. 1988, pp. 801-807.
Ward W.K., et al., "A New Amperometric Glucose Microsensor: In Vitro and Short-Term In Vivo Evaluation," Biosensors & Bioelectronics, vol. 17, 2002, pp. 181-189.
Wientjes K.J.C., "Development of a Glucose Sensor for Diabetic Patients," (Ph.D. Thesis), 2000, 212 pages.
Wilson G.S., et al., "Enzyme-Based Biosensors for In Vivo Measurements," Chem. Rev., vol. 100, 2000, pp. 2693-2704.
Wood W D., et al., "Hermetic Sealing with Epoxy," Pave Technology-Mechanical Engineering, Mar. 1990, 3 pages.
U.S. Appl. No. 16/452,364, filed Jun. 25, 2019, Abandoned.
U.S. Appl. No. 12/829,337, filed Jul. 1, 2010, Abandoned.

* cited by examiner

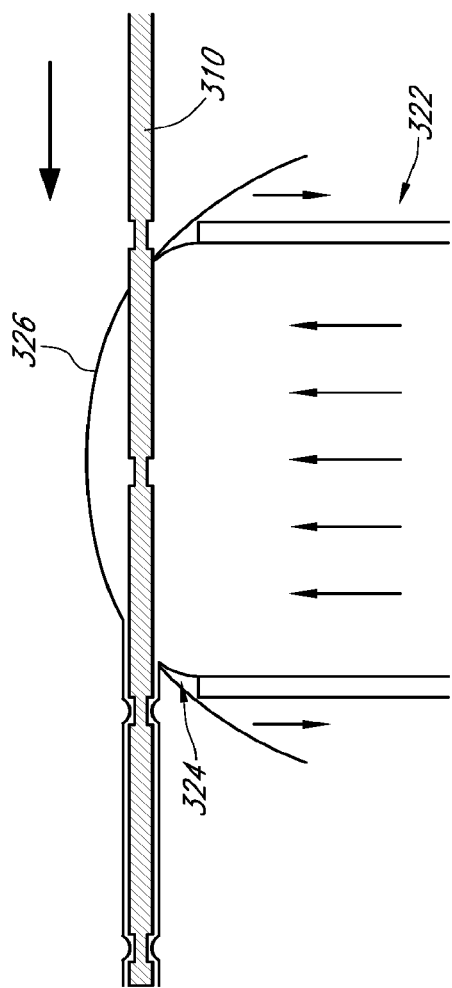

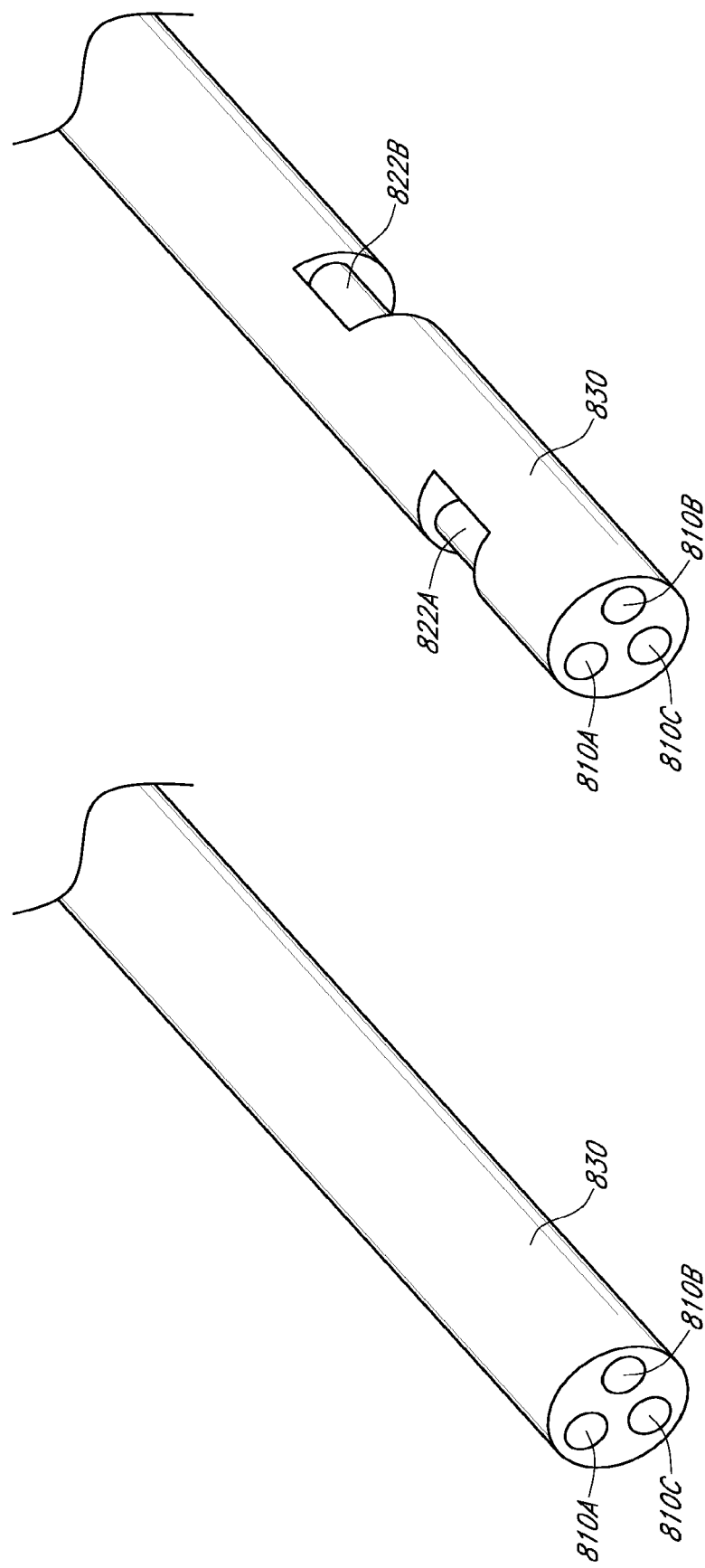

CONTINUOUS ANALYTE SENSORS AND METHODS OF MAKING SAME

INCORPORATION BY REFERENCE TO RELATED APPLICATIONS

This application is a continuation of U.S. application Ser. No. 16/452,364, filed Jun. 25, 2019, which is a continuation of U.S. application Ser. No. 12/829,337, filed Jul. 1, 2010, which claims the benefit of priority under 35 U.S.C. § 119(e) to U.S. Provisional Application No. 61/222,716 filed on Jul. 2, 2009, U.S. Provisional Application No. 61/222,815 filed on Jul. 2, 2009, and U.S. Provisional Application No. 61/222,751 filed on Jul. 2, 2009, the disclosures of which are hereby expressly incorporated by reference in their entireties and are hereby expressly made a portion of this application.

FIELD OF THE INVENTION

The embodiments described herein relate generally to continuous analyte sensors and systems and methods for making these sensors.

BACKGROUND OF THE INVENTION

Diabetes mellitus is a chronic disease, which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (e.g., kidney failure, skin ulcers, or bleeding into the vitreous of the eye) associated with the deterioration of small blood vessels. Sometimes, a hypoglycemic reaction (low blood sugar) is induced by an inadvertent overdose of insulin, or after a normal dose of insulin or glucose-lowering agent accompanied by extraordinary exercise or insufficient food intake.

A variety of implantable continuous electrochemical analyte sensors have been developed for continuously measuring blood glucose concentrations. Typically, these types of sensors have been made by batch processes, which may not be suitable for large-scale, low-cost manufacturing, and which often result in batch-to-batch variations, thereby resulting in property variations among the sensors produced.

SUMMARY OF THE INVENTION

Accordingly, there is a need for a process and system that will reduce production costs through labor reduction and minimize variations among the sensors produced, by providing automated, continuous manufacturing of continuous analyte sensors.

In a first aspect, a method is provided for manufacturing a continuous analyte sensor, the method comprising applying an insulating material to an elongated conductive body comprising a conductive surface by advancing the elongated conductive body through a meniscus comprising the insulating material; and drying or curing the applied insulating material to form a coating of the insulating material on the elongated conductive body, the coating comprising a portion of the continuous analyte sensor, whereby a continuous analyte sensor configured for in vivo use is obtained.

In an embodiment of the first aspect, the method further comprises continuously circulating a liquid comprising the insulating material in a vessel, whereby the meniscus is provided at a wall of the vessel.

In an embodiment of the first aspect, the method further comprises removing a fraction of the insulating material applied to the elongated conductive body.

In an embodiment of the first aspect, removing is performed by advancing the elongated conductive body through a die.

In an embodiment of the first aspect, the method further comprises determining whether a thickness of the coating is within a predetermined range; and repeating applying the insulating material to the elongated conductive body if the thickness of the coating is outside of the predetermined range.

In an embodiment of the first aspect, the predetermined range of the thickness of the coating is from about 5 microns to about 50 microns.

In an embodiment of the first aspect, the method further comprises applying an adhesion promoter to the elongated conductive body before applying the insulating material.

In an embodiment of the first aspect, the method further comprises etching a portion of the coating.

In an embodiment of the first aspect, the method further comprises cutting the elongated conductive body into a plurality of sections.

In an embodiment of the first aspect, each section is associated with an individual continuous analyte sensor.

In an embodiment of the first aspect, the insulating material is selected from the group consisting of polyurethane, polyethylene, and polyimide.

In an embodiment of the first aspect, the elongated conductive body is a wire with a circular cross-sectional shape or a substantially circular cross-sectional shape.

In an embodiment of the first aspect, the conductive surface of the elongated conductive body comprises platinum.

In an embodiment of the first aspect, the conductive surface of the elongated conductive body comprises at least one conductive material selected from the group consisting of platinum-iridium, gold, palladium, iridium, graphite, carbon, conductive polymers, and combinations thereof.

In an embodiment of the first aspect, advancing the elongated conductive body through the meniscus is performed by a reel-to-reel system.

In a second aspect, a method is provided for manufacturing a continuous analyte sensor, the method comprising applying a conductive material to an elongated conductive body by advancing the elongated conductive body through a liquid comprising the conductive material; drying or curing the applied liquid to form a coating of the conductive material on the elongated conductive body, the coating comprising a portion of the continuous analyte sensor; determining whether a thickness of the coating is within a predetermined range; and, if the thickness is below the predetermined range, repeating steps of applying a conductive material and drying or curing the applied liquid until the thickness of the coating is determined to be within the predetermined range, whereby a continuous analyte sensor configured for in vivo use is obtained.

In an embodiment of the second aspect, the method further comprises removing a fraction of the conductive material applied to the elongated conductive body.

In an embodiment of the second aspect, removing is performed by advancing the elongated conductive body through a die.

In an embodiment of the second aspect, the conductive material is Ag/AgCl.

In an embodiment of the second aspect, the predetermined range of the thickness of the coating is from about 1 micron to about 20 microns.

In an embodiment of the second aspect, the conductive material is platinum.

In an embodiment of the second aspect, the predetermined range is from about 1 micron to about 10 microns.

In an embodiment of the second aspect, the method further comprises applying an adhesion promoter to the elongated conductive body before applying the conductive material.

In an embodiment of the second aspect, the method further comprises etching a portion of the coating.

In an embodiment of the second aspect, the method further comprises cutting the elongated conductive body into a plurality of sections.

In an embodiment of the second aspect, each section is associated with an individual continuous analyte sensor.

In an embodiment of the second aspect, the conductive material is Ag/AgCl.

In an embodiment of the second aspect, the conductive material has a particle size associated with a maximum particle dimension that is less than about 100 microns.

In an embodiment of the second aspect, the elongated conductive body is a wire with a circular cross-sectional shape or a substantially circular cross-sectional shape.

In an embodiment of the second aspect, the elongated conductive body comprises an outer surface comprising an insulating material selected from the group consisting of polyurethane, polyethylene, and polyimide.

In an embodiment of the second aspect, applying a conductive material is performed by a reel-to-reel system.

In a third aspect, a system is provided for manufacturing a continuous analyte sensor, the system comprising a coating vessel configured to hold a coating material in liquid form; a reel-to-reel system configured to advance an elongated conductive body through the coating material, whereby the coating material is applied to the elongated conductive body; a thickness measurement sensor configured to measure a dimension indicative of a thickness of a coating formed from the coating material applied to the elongated conductive body; an etching system configured to remove a portion of the coating material applied to the elongated conductive body; and a cutter configured to cut the elongated conductive body into a plurality of sections, wherein each section is associated with an individual continuous analyte sensor.

In an embodiment of the third aspect, the system further comprises a die configured to remove a portion of the coating material applied to the elongated conductive body.

In an embodiment of the third aspect, the elongated conductive body is a wire with a circular cross-sectional shape or a substantially circular cross-sectional shape.

In an embodiment of the third aspect, the coating material comprises an insulating material selected from the group consisting of polyurethane, polyethylene, and polyimide.

In an embodiment of the third aspect, the coating material comprises a conductive material selected from the group consisting of platinum, silver/silver chloride, platinum-iridium, gold, palladium, iridium, graphite, carbon, conductive polymers, and alloys and combinations thereof.

In an embodiment of the third aspect, the system further comprises a pump and conduit system configured to circulate the coating material in liquid form in the coating vessel to provide a meniscus at a wall of the coating vessel.

In an embodiment of the third aspect, coating material is a component of a solution, wherein the solution is controlled to have a predetermined viscosity.

In an embodiment of the third aspect, the viscosity is controlled by selecting a concentration of the coating material in the solution or by selecting a solution temperature.

BRIEF DESCRIPTION OF THE DRAWINGS

FIG. 3B is a schematic diagram providing a detailed view of the interface between the elongated conductive body and the meniscus, of the embodiment illustrated in FIG. 3A.

FIG. 8A illustrates one embodiment of an elongated conductive body; FIG. 8B illustrates the embodiment of FIG. 8A after it has undergone laser ablation treatment.

Figure 1A:
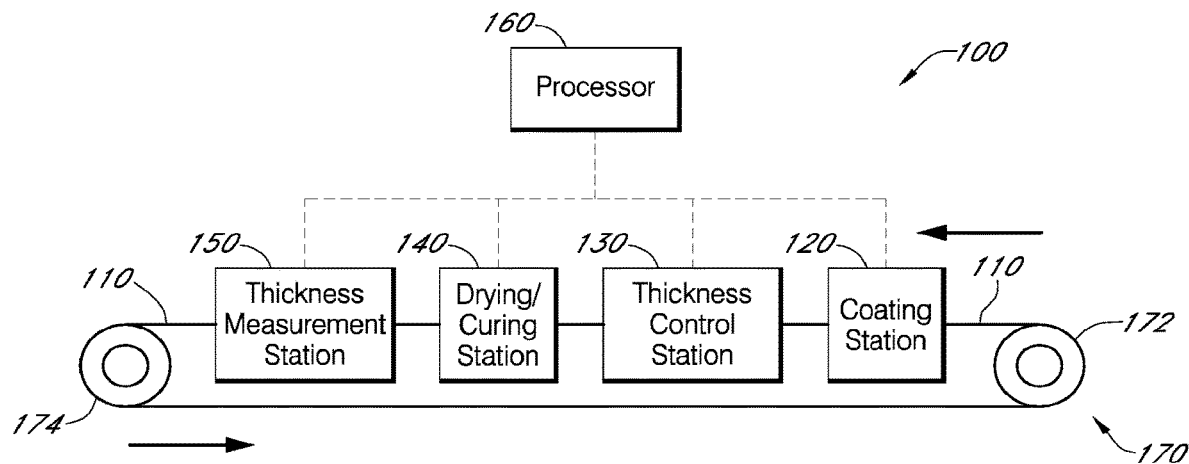
FIG. 1A is a schematic diagram of one embodiment of an automated, continuous system for manufacturing continuous analyte sensors.

It should be understood that the figures shown herein are not necessarily drawn to scale.

DETAILED DESCRIPTION OF THE PREFERRED EMBODIMENT

The following description and examples describe in detail some exemplary embodiments of systems and methods for manufacturing continuous analyte sensors. It should be understood that there are numerous variations and modifications of the systems, methods, and devices described herein that are encompassed by the present invention. Accordingly, the description of a certain exemplary embodiment should not be deemed to limit the scope of the present invention.

Definitions

In order to facilitate an understanding of the devices and methods described herein, a number of terms are defined below.

The term "analyte," as used herein, is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "continuous," as used herein in reference to analyte sensing, is a broad term, and is to be given its ordinary and customary meaning to a person of ordinary skill in the art (and is not to be limited to a special or customized meaning), and refers without limitation to the continuous, continual, or intermittent (e.g., regular) monitoring of analyte concentration, such as, for example, performing a measurement about every 1 to 10 minutes.

The term "elongated conductive body," as used herein is a broad term, and is to be given its ordinary and customary meaning to a person of ordinary skill in the art (and is not to be limited to a special or customized meaning), and refers without limitation to an elongated body formed at least in part of a conductive material and includes any number of coatings that may be formed thereon. By way of example, an "elongated conductive body" can mean a bare elongated core (e.g., a conductive metal wire, a non-conductive polymer rod) or an elongated core coated with one, two, three, four, five, or more layers of material that may be or may not be conductive.

The terms "electrochemically reactive surface" and "electroactive surface," as used herein, are broad terms, and are to be given their ordinary and customary meaning to a person of ordinary skill in the art (and are not to be limited to a special or customized meaning), and refer without limitation to the surface of an electrode where an electrochemical reaction is to take place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte.

The phrase "distal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include a membrane system having a diffusion resistance layer and an enzyme layer. If the sensor is deemed to be the point of reference and the diffusion resistance layer is positioned farther from the sensor than the enzyme layer, then the diffusion resistance layer is more distal to the sensor than the enzyme layer.

The phrase "proximal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a diffusion resistance layer and an enzyme layer. If the sensor is deemed to be the point of reference and the enzyme layer is positioned nearer to the sensor than the diffusion resistance layer, then the enzyme layer is more proximal to the sensor than the diffusion resistance layer.

The term "interferents," as used herein, is a broad term, and is to be given its ordinary and customary meaning to a person of ordinary skill in the art (and is not to be limited to a special or customized meaning), and refers without limitation to effects or species that interfere with the measurement of an analyte of interest in a sensor to produce a signal that does not accurately represent the analyte measurement. In an exemplary electrochemical sensor, interferents can include compounds with an oxidation potential that overlaps with that of the analyte to be measured.

The terms "membrane system" and "membrane," as used herein, are broad terms, and are to be given their ordinary and customary meaning to a person of ordinary skill in the art (and are not to be limited to a special or customized meaning), and refer without limitation to a permeable or semi-permeable membrane that can comprise one or more layers and constructed of materials, which are permeable to oxygen and may or may not be permeable to an analyte of interest. In one example, the membrane system comprises an immobilized glucose oxidase enzyme, which enables an electrochemical reaction to occur to measure a concentration of glucose.

The term "coefficient of variation," as used herein, is a broad term, and is to be given its ordinary and customary meaning to a person of ordinary skill in the art (and is not to be limited to a special or customized meaning), and refers without limitation to the ratio of the standard deviation of a distribution to its arithmetic mean. The coefficient of variation can be calculated by the equation: coefficient of variation=standard deviation/mean.

The term "sensitivity," as used herein, is a broad term, and is to be given its ordinary and customary meaning to a person of ordinary skill in the art (and is not to be limited to a special or customized meaning), and refers without limitation to an amount of electrical current produced by a predetermined amount (unit) of the measured analyte. For example, in one embodiment, a sensor has a sensitivity (or slope) of from about 1 to about 300 picoAmps of current for every 1 mg/dL of glucose analyte.

The term "current density," as used herein, is a broad term, and is to be given its ordinary and customary meaning to a person of ordinary skill in the art (and is not to be limited to a special or customized meaning), and refers without limitation to an amount of electrical current per area produced by a predetermined amount (unit) of the measured analyte. For example, in one embodiment, a sensor has a sensitivity (or slope) of from about 3 to about 1,000 picoAmps of current per $mm^2$ of electroactive surface, for every 1 mg/dL of glucose analyte.

The term "chamber," as used herein, is a broad term, and is to be given its ordinary and customary meaning to a person of ordinary skill in the art (and is not to be limited to a special or customized meaning), and refers without limitation to a partially or fully enclosed space (e.g., chambers, conduits, channels, capillaries, tubes, wells, cells, vessels, microchannels, or the like).

Overview

FIG. 1A provides a schematic diagram of one embodiment of an automated, continuous system 100 for manufacturing continuous analyte sensors, whereby an elongated conductive body 110 is continuously advanced through a series of stations, each of which treats the elongated conductive body 110. As shown, these stations can include, but are not required to include, a coating station 120 for depositing coating material (e.g., insulating, conductive, or membrane material) onto the elongated conductive body 110, a thickness control station 130 for removing excess coating material from the elongated conductive body 110, a drying/curing station 140 for curing the coating material on the elongated conductive body 110, and a thickness measurement station 150 for measuring the thickness of the elongated conductive body 110 (including any coatings thereon). During the coating process, the elongated conductive body 110 can be advanced through this series of stations repeatedly, i.e., by making multiple repeated passes, until a preselected thickness has been formed on the elongated conductive body. The system 100 described herein is merely exemplary, and some stations may be omitted or replaced by other stations.

Although not shown in FIG. 1A, in some embodiments, the system can also include an etching station for removing or stripping portions of a coated assembly structure on the elongated conductive body (e.g., to create window regions corresponding to working electrodes on the elongated conductive body). Etching to create window regions can be achieved by removing a portion of the insulating layer, conductive layer, or the like, from the elongated conductive body, using ablation (e.g., laser skiving), chemical etching, or other known techniques. Additionally or optionally, the system can also include a pre-coating treatment station for pre-cleaning the elongated conductive body before the coating process, and a post-coating treatment station for post-cleaning after the coating process. Additionally or optionally, the system can also include a singulation station for cutting the elongated conductive body into individual pieces corresponding individual sensors.

The system 100 can also be equipped with an automated control system comprising detector elements, control elements, and a processor 160. The detector and control elements can be embedded in the stations and disposed anywhere on or near the pathway of the elongated conductive body 110. The detector elements are configured to transmit to the processor 160 signals relating to certain process conditions of the system 100, such as, for example, the temperature of the coating solution, the humidity of the atmosphere immediately around a region of the elongated conductive body which is undergoing or about to undergo meniscus coating or laser ablation, the rate at which the elongated conductive body 110 is advancing, or the last measured thickness of the elongated conductive body 110. The processor 160 is programmed to process these input signals and transmit output signals to control operation of the control elements, e.g., valves, motors, pumps, agitators, heat lamps, die opening, etc., so that preselected process conditions for optimum controlled coating processing can be achieved and maintained. By managing the processing conditions at a predetermined optimal level, the yield and reproducibility of the continuous analyte sensors fabricated can be increased.

In some embodiments, a detector element in the form of a temperature transducer (e.g., a thermistor) and a control element in the form of a heat source (e.g., a heat lamp) is disposed at certain positions along the pathway of the elongated conductive body 110 to provide temperature control of the elongated conductive body 110. During operation, if the temperature transducer detects a temperature that is less than a preselected temperature range, the temperature transducer is configured to transmit a signal to the processor 160, which in turn responds by transmitting a signal to activate the heat source to heat the elongated conductive body 110 to the preselected temperature. In further embodiments, the heat source is positioned near the entrance of the coating station 120, so that the elongated conductive body 110 is heated to a preselected temperature that facilitates the coating process. Alternatively or additionally, a heat source can be provided near the exit of the coating station 120 to speed the evaporation of residual solvent on the elongated conductive body 110.

In the embodiment shown in FIG. 1A, the system 100 comprises a transport mechanism 170 for sequentially advancing the elongated conductive body 110 through the various stations. In this particular embodiment, the system 100 employs a reel-to-reel mechanism comprising a motor (not shown in FIG. 1A), a rotatable supply spool 172, and a rotatable return spool 174. During operation, the elongated conductive body 110 is attached to both the supply spool 172 and the return spool 174. Although in some embodiments, the elongated conductive body is configured to sequentially advance through the stations in a horizontal or substantially horizontal arrangement, in other embodiments, a vertical or substantially vertical arrangement can also be used for one or more of the stations, for example, to address any gravity-induced sagging issues with respect to a fresh coating on the elongated conductive body.

Figure 2B:
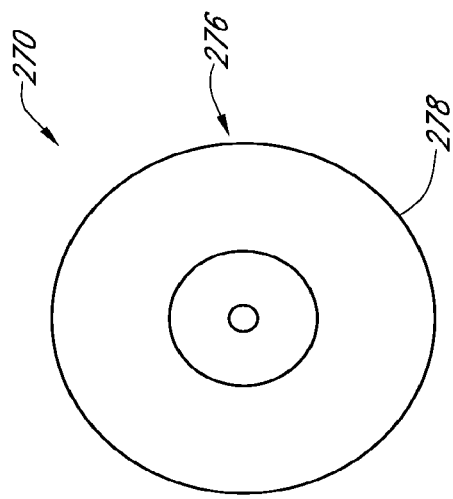
FIG. 2B is a front view of the embodiment illustrated in FIG. 2A.
Figure 2A:
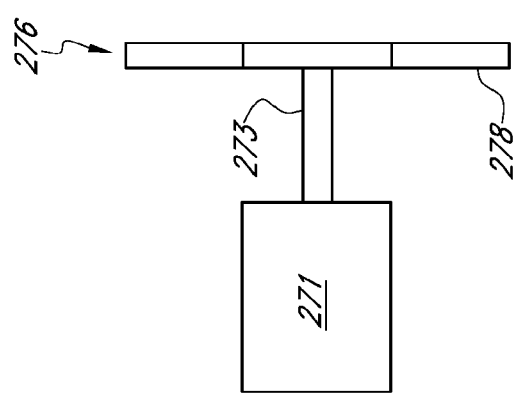
FIG. 2A is a side view of one embodiment of a transport mechanism.

It is contemplated that any of a variety of transport mechanisms can be used to advance the elongated conductive body 110. For example, FIGS. 2A and 2B, illustrate a side view and a front view, respectively, of one embodiment of a transport mechanism 270 comprising a spool 276, suitable for use as a supply spool, a return spool, or any other spool employed by the system. The spool 276 can include a reel 278 mechanically connected to a motor 271 via a rotatable shaft 273. The motor 271 can be any of a variety of conventional motors suitable for the applications contemplated. The reel 278 can be any type of reel upon which the elongated conductive body can be wound, and can comprise a soft material, such as silicone rubber, polyurethane, or nylon, for example, that will not cut away at coatings on the elongated conductive body and will not allow the elongated conductive body to slide freely over the reel when the reel is rotated. The diameter and width of the reel 278 can be varied depending in part on the dimensions of the elongated conductive body and other design considerations. In some embodiments, reels with a small width can be employed where there are tight space constraints. In these embodiments, coils of the elongated conductive body on the reel can overlap and touch portions of adjacent coils. In other embodiments, however, reels having a large width can be desirable, such that the coils can be arranged to not touch each other. In some embodiments, reels with large diameters can be used, resulting in a smaller bend radius, thereby minimizing the risk that materials on the elongated conductive body will crack or chip off.

Although in the embodiment shown in FIG. 1A, the system 100 comprises one supply spool 172 and one return spool 174, in other embodiments the system can comprise any number of spools. For example, in other embodiments, the system can comprise two, three, four, five, or more supply spools associated with an equal number or a different number of return spools.

Figure 1B:
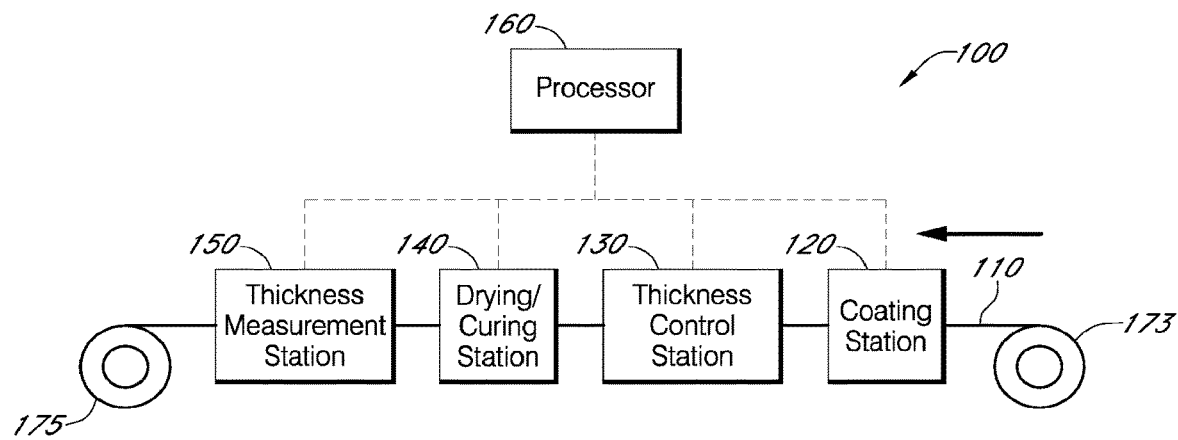
FIG. 1B is a schematic diagram of another embodiment of an automated, continuous system for manufacturing continuous analyte sensors.
Figure 1C:
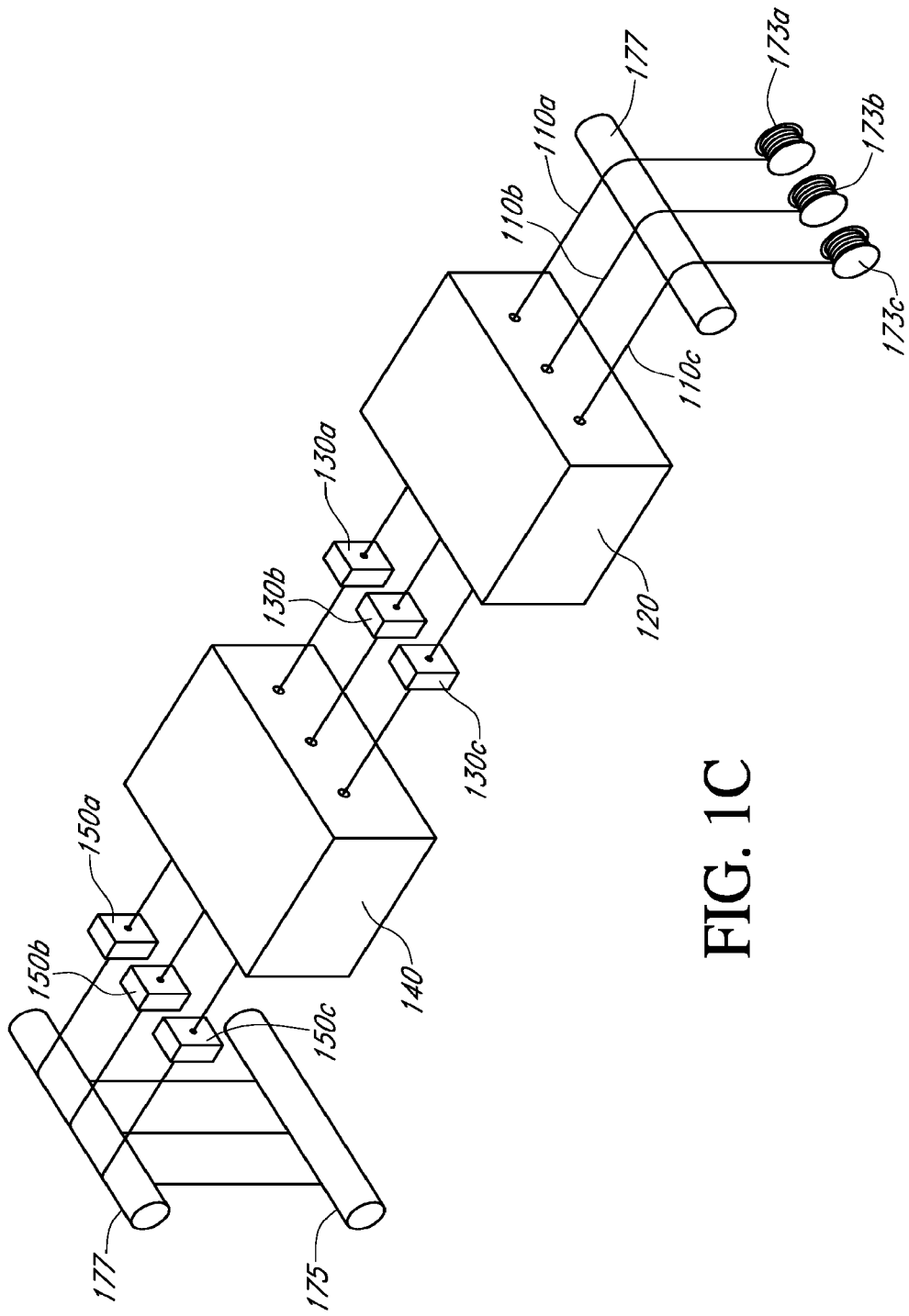
FIG. 1C is a schematic diagram of yet another embodiment of an automated, continuous system for manufacturing continuous analyte sensors.

In addition, the system can comprise any number of stations. As illustrated in FIG. 1C, in one exemplary embodiment, the system can comprise three supply spools 173a, 173b, 173c that provide three elongated conductive bodies 110a, 110b, 110c, each of which are wound into a single take-up spool 175. In this particular embodiment, the system comprises one coating station 120, three thickness control stations 130a, 130b, 130c, one drying/curing station 140, and three thickness measurement stations 150a, 150b, 150c. In other embodiments, the system can comprise any number of station combinations. For instance, in one embodiment, the system can comprise five coating stations, five thickness control stations, one drying/curing station, and one thickness measurement station. In another embodiment, the system can comprise three coating stations, three thickness stations, three drying/curing stations, and one thickness measurement station.

Figure 1D:
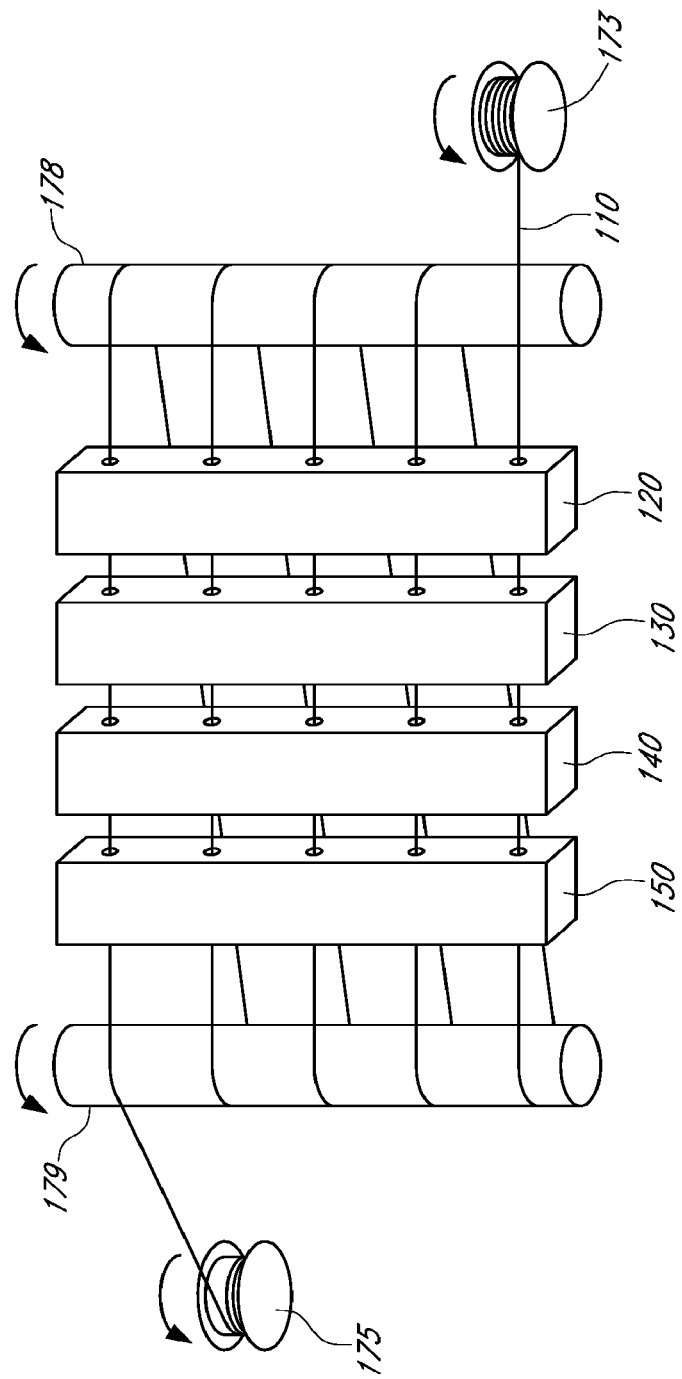
FIG. 1D is a schematic diagram of yet another embodiment of an automated, continuous system for manufacturing continuous analyte sensors.

In yet another embodiment, as illustrated in FIG. 1D, the system can comprise four stations, each of which is configured to treat multiple portions of the elongated conductive body 110. In this particular embodiment, the elongated conductive body 110 is unwound from a supply spool 173 and becomes engaged with a first guide roller 178 that guides the elongated conductive body 110 to a coating station 120. Thereafter, the elongated conductive body 110 is advanced through a thickness control station 130, a drying/curing station 140, and a thickness measurement station 150. After exiting the measurement station 150, the elongated conductive body 110 engages a second guide roller 179, by which it is returned to the first guide roller 178. As illustrated in FIG. 1D, the elongated conductive body 110 is then advanced through additional coating station/thickness control station/drying/curing station/thickness measurement station series/sequences. After passing through a preselected number of the aforementioned series/sequences, the elongated conductive body 110 is advanced to the second guide roller 179, by which it is wound into the take-up spool 175. Although in the embodiment illustrated in FIG. 1D, the system is configured to provide five series/sequences of stations; in other embodiments the system can comprise a different number of series/sequences. For example, the system can be configured to provide two, three, five, six, seven, or more series/sequences of stations.

As shown in FIGS. 1C and 1D, in some embodiments, the system can include one or more pulleys or guide rollers 177, 178, 179 for guiding the elongated conductive body 110 as it advances through the various stations of the system 100. The guide rollers can be positioned at any suitable location along the pathway of the elongated conductive body 110. For example, in one embodiment, a guide roller can be disposed at a position near the entrance of a certain station, such as the coating station 120. In another embodiment, a guide roller can be disposed at a position near the exit of a certain station, such as a thickness control station 130. In yet another embodiment, guide rollers can be disposed near both the entrance and exit of a certain station. In other embodiments, the system does not use guide rollers, but instead uses the tension present in the elongated conductive body 110 (derived from the transport mechanism 170) to guide it along its pathway as it advances through the various stations.

In the embodiment shown in FIG. 1A, the pathway of the elongated conductive body 110 is a cyclical pathway, i.e., the pathway extends from the supply spool 172 to the return spool 174, and then extends back to the supply spool 172 from the return spool 174. In other embodiments, however, the pathway may not be cyclical, but is single directional instead. As illustrated in FIG. 1B, in some of these embodiments, the elongated conductive body 110 is unwound from a supply spool 173 and wound into a take-up spool 175, after which it can be retrieved by an operator and loaded onto another system for further processing.

In some embodiments, each of the spools is associated with a motor configured to drive the spool. In other embodiments, one or more of the spools is not associated with a motor. For example, in one embodiment, wherein the pathway is single direction, the transport mechanism can comprise a take-up spool driven by a motor to rotate at a preselected speed of rotation, while a corresponding supply spool is maintained effectively freely rotatable. More specifically, in this embodiment, whereas rotation of the take-up spool is actively driven by a motor, rotation of the supply spool is driven by translational forces from the moving elongated conductive body, as it is driven by the rotating take-up spool. When the transport mechanism is activated, the torque exerted by the take-up spool provides tension to the elongated conductive body as it unwinds from the supply spool, advances through the various stations of the system, and eventually winds into the take-up spool. An increase in the torque exerted by the take-up spool may also increase the tension present in the elongated conductive body.

The tension present in the elongated conductive body 110 can be measured by any of a variety of tension detectors. For example, in some embodiments, a tension detector is disposed at various positions along the pathway of the elongated conductive body 110 to directly measure its tension. In other embodiments, the tension is indirectly measured by measuring the torques exerted by the various spools and calculating the torque differences between the spools. If the tension is determined to be greater or less than a preselected value, the tension detector can be configured to transmit a signal to the processor, which is programmed to determine whether a problem exists (e.g., a severed elongated conductive body or one detached from the reel). If the determination is positive, the system can optionally respond with an alert or alarm to notify an operator.

In some of the embodiments described herein, the transport mechanism 170 is configured to advance the elongated conductive body 110 at a constant or substantially constant preselected speed. Selection of the preselected speed can depend in part on design considerations associated with certain preselected process conditions (e.g., the preselected viscosity and solids content of the coating solution, suspension, dispersion, or other liquid comprising the coating material) that will provide optimal coating thickness control. In some embodiments, the elongated conductive body is configured to advance at a preselected speed greater than about 0.5 cm per minute, or greater than about 10 cm per minute, or greater than about 25 cm per minute, or greater than about 50 cm per minute, or even greater than about 250 cm per minute. In alternative embodiments, a variable-speed transport mechanism can be used to advance the elongated conductive body at varying speeds. For example, in some embodiments, the transport mechanism can be configured to periodically halt the advancement of the elongated conductive body.

To confirm that the elongated conductive body is advancing at the preselected speed, a speed measurement system (e.g., a vision system) can be employed to measure the elongated conductive body's actual speed. If the measured speed is not within a certain range of the preselected speed, the vision system is configured to transmit a signal to the processor, which in turn can adjust motor settings in response.

While the transport mechanism has been described hereinabove with respect to a reel-to-reel embodiment, the elongated conductive body 110 may also be advanced through the series of stations with any of a variety of other transport mechanisms, such as, for example, a robotic system, a conveyor system, and other like systems. These other transport mechanisms may be used in combination with (or as an alternative to) a reel-to-reel system. For example, in one embodiment, a reel-to-reel system is used to move the elongated conductive body 110 before it is singulated into individual pieces 110', and a robotic system is used to move the individual pieces 110' after the singulation process.

Figure 1E:
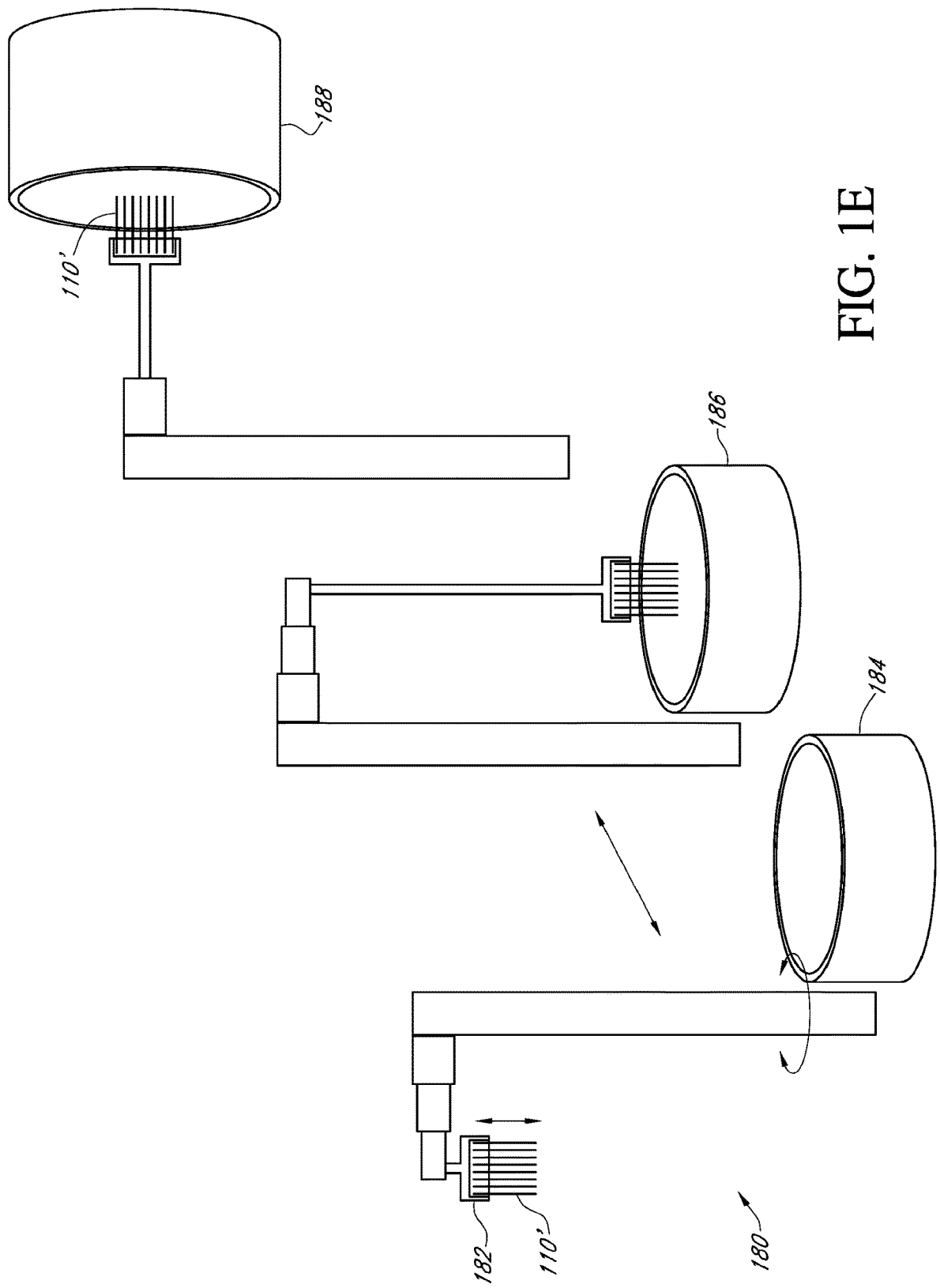
FIG. 1E is a schematic diagram of yet another embodiment of an automated, continuous system for manufacturing continuous analyte sensors.

FIG. 1E illustrates one embodiment of a robotic system 180, which can range in size from a large device suitable for industrial scale use to a small device suitable for laboratory bench tops. Robotic systems may be advantageous in certain instances because they can provide accurate, precise positioning of the elongated conductive body 110' in two or three dimensions. In addition, they are highly flexible and reconfigurable, which can be advantageous for facilitating the physical transfer of individual pieces to/from a variety of stations, vessels, containers, chambers, or the like. Referring back to FIG. 1E, the robotic system 180 comprises an elongated conductive body holder 182 (e.g., a robot arm) designed to move an elongated conductive body 110' through variable programmed motions for performance of a variety of tasks (e.g., for transferring the elongated conductive body 110' from one coating vessel 184 to another 186 for different coating applications, and from one station to another for a variety of treatments). Although in the embodiment illustrated in FIG. 1E, the elongated conductive body holder 182 is shown holding a four elongated conductive bodies 110', in alternative embodiments, the elongated conductive body holder 182 may be capable of holding any number of elongated conductive bodies 110'.

In certain embodiments, the elongated conductive body holder 182 is capable of both vertical movements and horizontal movements (e.g., linear or rotational), thereby allowing not only for movement between stations, vessels, containers, chambers, or the like, but also for movement that causes the elongated conductive body 110' to be submerged or dipped in a coating solution of a coating vessel 184, or movement that causes the elongated conductive body 110' to be placed into a curing or drying chamber 188. By using an elongated conductive body holder 182 capable of various programmed movements, both the number of times and the length of time that an elongated conductive body 110' is in a station or is being coated, cured, dried, or treated in a vessel or chamber can be controlled. By way of example and not to be limiting, the robot's elongated conductive body holder 182 can be instructed to dip the elongated conductive body 110' (i.e., post-singulation in the form of an individual piece) into the coating vessel 184 for a plurality of dips, with each dip interspersed by drying or curing of the coating. While the coating process has been described hereinabove primarily with respect to a dipping technique, it should be understood that any of a variety of other coating techniques, such as, for example, spraying, electro-depositing, dipping, or casting, may also be used in addition to (or as an alternative to) dipping. For instance, in certain embodiments, the elongated conductive body holder 182 is instructed to place the elongated conductive body 110' in a position for one or more spraying sessions with a certain coating material to form a particular layer of the membrane, and then to dip the elongated conductive body 110' for one or more coating sessions in a coating solution to form another layer. The length of time of each dip/spray session and the length of time between each session can be varied or constant.

In one embodiment involving the robotic system 180, the elongated conductive body 110' (in the form of an individual piece) is dipped one or more times for a predetermined time period in a pretreatment solution, then dipped one or more times for a predetermined time period into a solution containing a material that is to form the electrode and/or interference layer, then dipped one or more times for a predetermined time period into a solution containing a material that is to form the enzyme layer, and then dipped one or more times (for a predetermined time period) into a solution containing a material that is to form the diffusion resistance layer. Before, after, and between the dips/sprays, the elongated conductive body 110' may be treated (e.g., conditioned, cleaned, cured, dried, etc.) or else maintained under normal ambient conditions. It should be understood that the process described above is merely exemplary, and some steps may be omitted or replaced by other steps.

Elongated Conductive Body

Figure 7A:
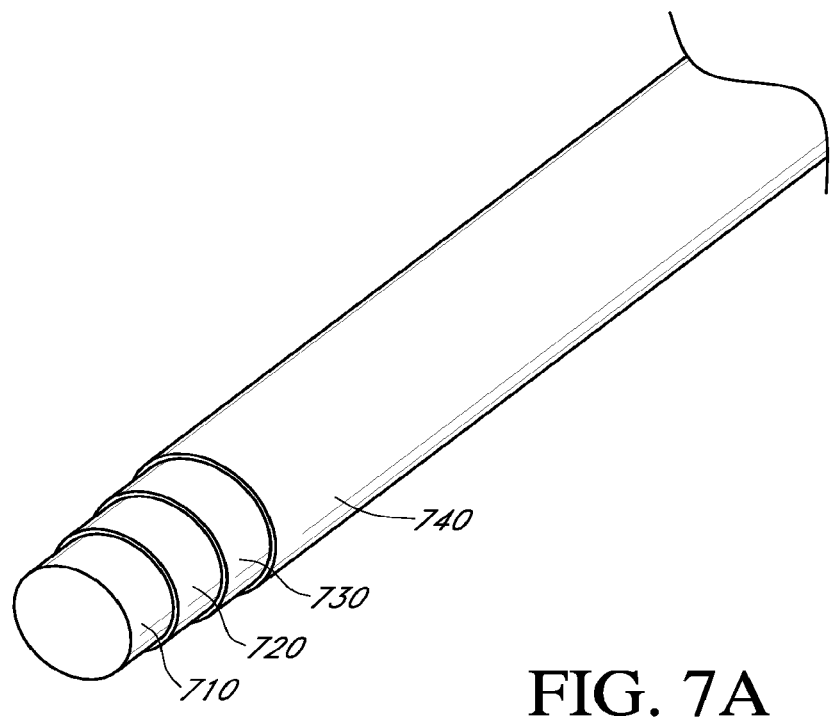
FIG. 7A illustrates one embodiment of an elongated conductive body.

Any of a variety of elongated conductive bodies can be treated by the systems and methods described herein. FIG. 7A illustrates one embodiment of an elongated conductive body comprising an elongated core 710, a first layer 720 that at least partially surrounds the core 710, a second layer 730 that at least partially surrounds the first layer 720, and a third layer 740 that at least partially surrounds the second layer 730. These layers, which collectively form a coating assembly structure, can be deposited onto the elongated core by any of a variety of techniques, such as, for example, by employing the coating processes described elsewhere herein. In some embodiments, the first layer 720 can comprise a conductive material, such as, for example, platinum, platinum-iridium, gold, palladium, iridium, graphite, carbon, a conductive polymer, an alloy, and/or the like, configured to provide suitable electroactive surfaces for one or more working electrodes. In certain embodiments, the second layer 730 can correspond to an insulator and comprise an insulating material, such as a non-conductive (e.g., dielectric) polymer, such as polyurethane, polyimide, polyolefin (e.g., polyethylene), for example. In some embodiments, the third layer 740 can correspond to a reference electrode and comprise a conductive material, for example, a silver-containing material, including, but not limited to, a polymer-based conducting mixture.

Figure 7B:
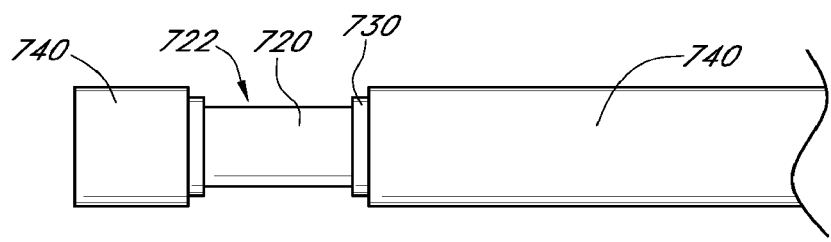
FIG. 7B illustrates the embodiment of FIG. 7A after it has undergone laser ablation treatment.
Figure 7C:
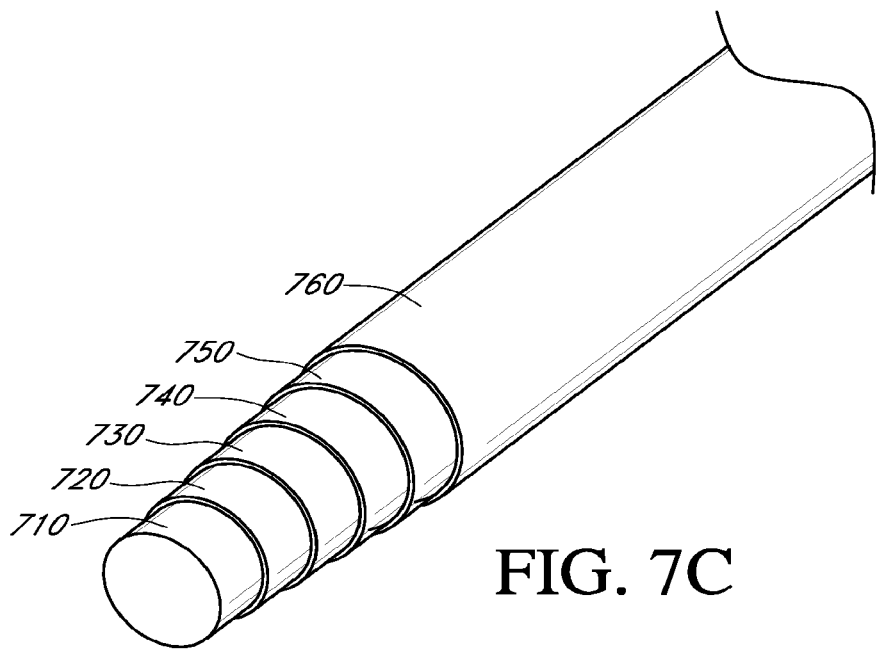
FIG. 7C illustrates another embodiment of an elongated conductive body.

FIG. 7C illustrates another embodiment of an elongated conductive body. In this embodiment, in addition to an elongated core 710, a first layer 720, a second layer 730, and a third layer 740, the elongated conductive body further comprises a fourth layer 750 and a fifth layer 760. In a further embodiment, the first layer 720 and the second layer 730 can be formed of a conductive material and an insulating material, respectively, similar to those described in the embodiment of FIG. 7A. However, unlike the embodiment of FIG. 7A, in this particular embodiment, the third layer 740 can be configured to provide the sensor with a second working electrode, in addition to the first working electrode provided by the first layer 720. In this particular embodiment, the fourth layer 750 can comprise an insulating material and provide insulation between the third layer 740 and the fifth layer 760, which can correspond to a reference electrode and comprise the aforementioned silver-containing material. It is contemplated that other similar embodiments are possible. For example, in alternative embodiments, the elongated conductive body can have 6, 7, 8, 9, 10, or more layers, each of which can be formed of conductive or non-conductive material.

Figure 8D:
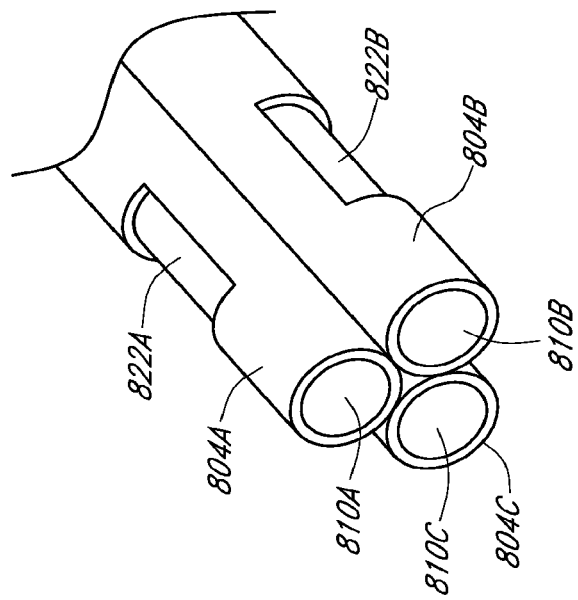
FIG. 8D illustrates the embodiment of FIG. 8C after it has undergone laser ablation treatment.
Figure 8C:
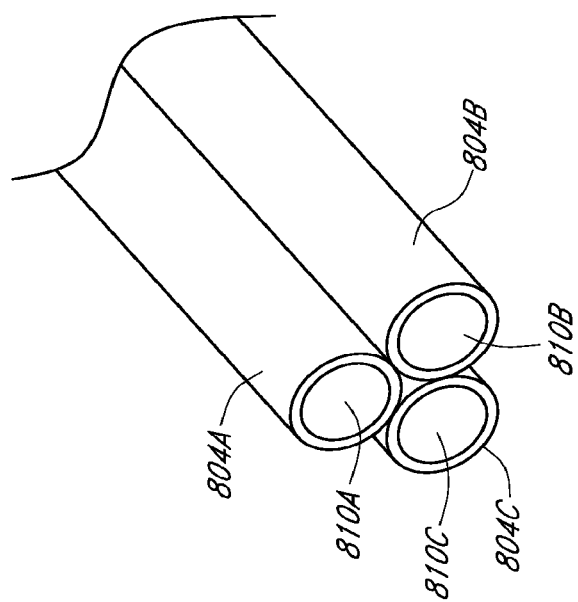
FIG. 8C illustrates another embodiment of an elongated conductive body.

FIGS. 8A and 8C illustrate other embodiments of the elongated conductive body. In the embodiment illustrated in FIG. 8A, the elongated conductive body comprises three elongated cores 810A, 810B, and 810C located in (e.g., embedded in, coated with) the insulator 830. FIG. 8C illustrates another embodiment of the elongated conductive body comprising three insulated conductive bodies, wherein each insulated conductive body includes an elongated core 810A, 810B, and 810C coated with an insulator 804A, 804B, and 804C). In some embodiments, the elongated cores (e.g., coated with insulator) are bundled together, such as by an elastic band, an adhesive, wrapping, a shrink-wrap or C-clip, as is known in the art. In other embodiments, the inner bodies (e.g., coated with insulator) are twisted, such as into a triple-helix or similar configuration. In one embodiment, two of the elongated cores (e.g., coated with insulator) are twisted together to form a twisted pair, and then a third core (e.g., with insulator) and/or elongated conductive body is twisted around the twisted pair. In some embodiments, the sensor can comprise additional elongated cores.

While in some embodiments described herein, the elongated core is shaped like a wire and has a circular cross-section, in other embodiments the cross-section of the elongated core can be oval, square, rectangular, triangular, polyhedral, star-shaped, C-shaped, T-shaped, X-shaped, Y-Shaped, irregular, or the like. The elongated core can be formed of any of a variety of suitable material, such as, platinum, platinum-iridium, gold, palladium, iridium, graphite, carbon, conductive or non-conductive polymer, alloys, glass, for example. In some embodiments, the elongated core comprises an inner core and a first layer, wherein an exposed electroactive surface of the first layer provides the working electrode of the continuous analyte sensor being manufactured. For example, in some embodiments, the inner core comprises stainless steel, titanium, tantalum and/or a polymer, and the first layer comprises platinum, platinum-iridium, gold, palladium, iridium, graphite, carbon, a conductive polymer, and/or an alloy.

The elongated conductive body can be designed (e.g., by material selection, by diameter selection, by treatment) to have certain mechanical properties. For instance, an elongated conductive body may be designed to meet a certain minimal level of tensile strength or minimal length of diameter, so that the elongated conductive body will not be prone to breakage during a reel-to-reel processing. In some embodiments, the tensile strength of the elongated conductive body is at least about 200 MPa, or at least about 500 MPa, or at least about 1,000 MPa, or at least about 2,000 MPa, or even at least about 5,000 MPa. In certain embodiments, the diameter of the elongated conductive body is at least about 5 microns, or at least about 15 microns, or at least about 25 microns, or at least about 50 microns, or at least about 75 microns, or at least about 100 microns, and or even at least about 200 microns. Other possible embodiments and features of the elongated conductive body are described in U.S. Provisional Application No. 61/222,751, the contents of which are incorporated by reference herein in its entirety.

Workpiece Station

The material that eventually forms the elongated conductive body may initially be in the form of one or more workpieces. The workpiece may be formed of any of a variety of materials, such as, for example, platinum, platinum-iridium, gold, palladium, iridium, graphite, carbon, conductive polymers, and alloys or combinations thereof. In some embodiments, the initial workpiece possesses the desired dimensions, shapes, and mechanical specifications, and thus minimal (or no) substantial mechanical or structural changes need to be made to the workpiece before it is treated and processed (e.g., coated, dried, etched, singulated, etc.) to form a continuous analyte sensor. In certain embodiments, the initial workpiece may already possess the desired shape (e.g., wire, tube, planar substrate, etc), but not the desired dimensions. In these embodiments, processing may involve resizing the workpiece to the desired dimensions.

In other embodiments, however, the initial workpiece does not possess any of the above-described desired specifications and properties, and thus the workpiece has to undergo processing, whereby the workpiece itself is worked on by machine or hand tools to impart structural and/or mechanical changes. These changes may involve, for example, cutting or shaping of the workpiece. They can also involve the addition of a layer (e.g., coating, cladding, plating, etc.) that circumscribes the outer surface of the workpiece. For example, the elongated conductive body may be fabricated to include a core and a cladding surrounding the core, both of which are formed from different materials. In some instances, fabricating the elongated conductive body to have a core formed with a less expensive, yet strong and flexible material (e.g., palladium, tantalum, stainless steel, or the like) and a thin layer of a more expensive material (e.g., platinum) to form the electroactive surface of the continuous analyte sensor, can enable a substantial reduction in the material costs required to build the continuous analyte sensor.

In one embodiment, fabrication of the elongated conductive body can be performed by inserting (e.g., by slip fitting) a rod or wire into a tube, the combination of which forms an initial structure of an elongated conductive body. The rod or wire may be formed of any of a variety of materials including, but not limited to, stainless steel, titanium, tantalum, and/or a polymer. The tube may be formed of a conductive material, such as, for example, platinum, platinum-iridium, gold, palladium, iridium, alloys thereof, graphite, carbon, or a conductive polymer. Alternatively, instead of using a tube to form the cladding, a layer of conductive material may be deposited onto the core. Deposition of the conductive material may be performed by any of a variety of techniques, such as, for example, chemical vapor deposition, physical vapor deposition (e.g., sputtering, vacuum deposition), chemical and electrochemical techniques, dip coating, spray coating, and optical coating. In some embodiments, the dip coating and spray coating processes described elsewhere herein may be used to deposit a coating layer onto the outer surface of the rod or wire.

After a cladding/plating/layer has been formed around the rod or wire, the elongated conductive body can then be passed through a series of dies to draw down the diameter of the elongated conductive body from a large diameter to a small diameter. With each pass through the die (e.g., a diamond die), the cross-sectional profile of the elongated conductive body is compressed, and the diameter associated therewith is reduced. It has been found that while compression tends to increase the tensile strength of the elongated conductive body, compression also tends to increase susceptibility of the elongated conductive body to brittleness, stress cracking, and even breakage. Accordingly, in some embodiments, an annealing step is used to cause changes in the mechanical and structural properties of the elongated conductive body, and more specifically, to relieve internal stresses, refine the structure by making it homogeneous, and improve cold working properties. It has also been found that drawing down the diameter of the elongated conductive body through large numbers of dies in small incremental steps, instead of through one or a few number of large incremental step(s), can result in better mechanical and structural properties. Accordingly, in some embodiments, the elongated conductive body is passed through a series of dies, with each successive die having a progressively smaller diameter. Between each die passing, the elongated conductive body may undergo an annealing treatment (e.g., by using an annealing oven), through which the elongated conductive body is softened and its ductility increased.

Figure 10B:
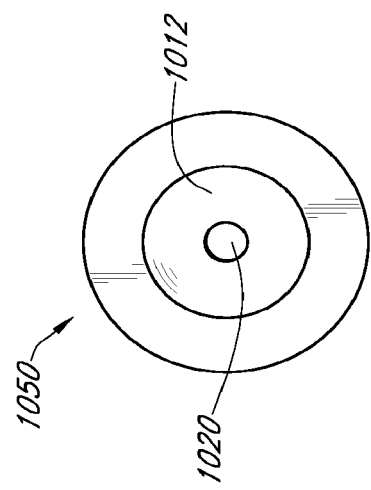
FIG. 10B provides a view of the die on lines 10B-10B of FIG. 10A.
Figure 10A:
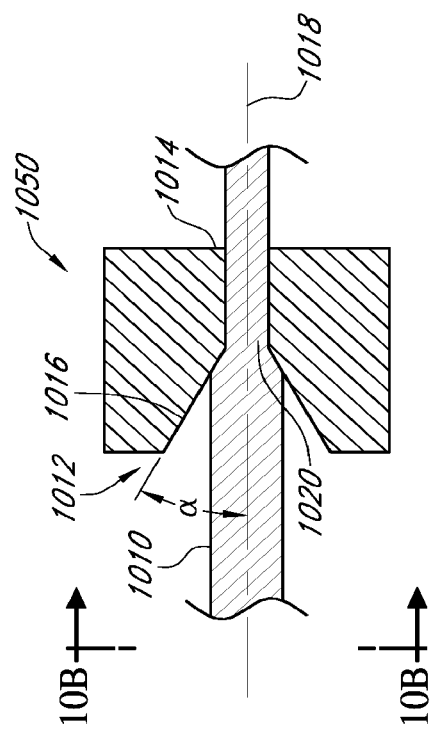
FIG. 10A illustrates one embodiment of a die.

FIG. 10A illustrates one embodiment of a die 1050 used to compress the elongated conductive body, so as to reduce its cross-sectional profile. FIG. 10B provides a view of the die on lines 10B-10B of FIG. 10A. As shown, the die 1050 comprises an orifice 1020, a front portion 1012, through which an elongated conductive body 1010 enters the die 1050, and a back portion 1014, through which the elongated conductive body 1010 exits. The edge 1016 of the front portion 1012 may have a tapering angle α defined by the longitudinal axis 1018 of die 1050 and the front edge 1016. The elongated conductive body 1010 is drawn through a die 1050 (e.g., diamond die, etc.) and through its orifice 1020.

In some embodiments, the shape and dimensions of the orifice 1020 may be changed, so that the elongated conductive body can be shaped and sized to have any desired cross sectional shape and dimensions.

As the elongated conductive body 1010 is forced through the die orifice 1050 to impart a shape or to reduce dimensions, the elongated conductive body 1010 becomes deformed. Drawing the elongated conductive body 1010 through a die with a large tapering angle will cause greater compression of the elongated conductive body 1010 than a die with a smaller tapering angle. Accordingly, drawing the elongated conductive body 1010 through a series of dies with large tapering angles may minimize the number of dies that an elongated conductive body has to be drawn through. However, it has been found that drawing the elongated conductive body 1010 through a successive number of dies, each with a smaller tapering angle, can substantially reduce the risk of breakage, brittleness, stress cracking, or other mechanical deficiencies that may be imparted on the elongated conductive body 1010. In some embodiments, the tapering angle $\alpha$ of the die is less than about 60 degrees, sometimes less than about 45 degrees, sometimes less than about 30 degrees, sometimes less than about 30 degrees, and sometimes less than about 10 degrees.

With certain embodiments (e.g., an elongated conductive body in the form of a wire), obtaining and maintaining concentricity of the elongated conductive body is important. Without concentricity of the elongated conductive body, subsequent coatings of the conductive, insulating, and membrane materials may not be uniform, and consequently performance of the fabricated continuous analyte sensor may be negatively impacted. For elongated conductive bodies with circular (or substantially circular) cross-sectional shape, a lack of uniformity of compressive forces exerted on the cross-sectional circumference of the elongated conductive body, can lead to loss of concentricity between the core and the clad/plate/layer and thereby cause certain portions of the elongated conductive body to be thicker than other portions. Accordingly, in some embodiments, the die 1050 is configured to cause the elongated conductive body 1010 to compress in a way such that compressive forces exerted on the cross-sectional circumference of the elongated conductive body are substantially uniform across the circumference, so that concentricity can be maintained. The risk of concentricity loss may also be reduced by use of a positioning system (e.g., a vision system) that may be disposed near or along the die 1050. The positioning system can be used to confirm that the elongated conductive body 110 is aligned correctly during its entry into and exit out of the die 1050, and that it is moving along a certain predetermined path (e.g., a path that is perpendicular to the plane defined by the orifice 1020). As an additional measure to minimize the risk of concentricity loss, portions of the die 1050, such as the orifice 1020, may be coated with a lubricant (e.g., oil) to reduce any buildup of friction associated with the advancement of the elongated conductive body 1010 through the die 1050.

In some embodiments involving a wire-shaped elongated conductive body with a substantially circular cross-sectional profile, the workpiece station comprises a series of dies, which collectively are capable of reducing the thickness of the elongated conductive body, while still substantially maintaining the concentricity of the elongated conduct body. In these embodiments, the reduction in thickness corresponds to the reduction from an original elongated conductive body diameter of up to about 250 microns, sometimes up to about 500 microns, sometimes up to about 1,000 microns, and sometimes up to about 2,500 microns, to a final diameter no less than about 100 microns, sometimes no less than about 50 microns, sometimes no less than about 25 microns, and sometimes no less than about 13 microns.

In addition (or as an alternative) to the treatments described above, the elongated conductive body can undergo any of a variety of processing to change its physical (and sometimes chemical) properties. For example, the elongated conductive body can undergo annealing, quenching, tempering, drawing, rolling, normalizing, work hardening, and/or work softening processes, so that the elongated conductive body acquires certain desired physical properties.

Etching Station

The automated, continuous system for manufacturing continuous analyte sensors may comprise an etching station, whereby portions of the coated assembly structure is stripped or otherwise removed. In some embodiments, removal of portions of deposited layers of coating can be performed to expose the one or more electroactive surface(s) of the elongated conductive body, thereby forming recessed regions or window regions/surfaces 420 corresponding to working electrodes. The terms "etching" and "etched" as used herein are broad terms, and are to be given their ordinary and customary meaning to a person of ordinary skill in the art (and are not to be limited to a special or customized meaning), and refer without limitation to a mechanism for forming one or more recessed regions within the elongated conducted body. It should be understood that the terms "etching" and "etched" as used herein is not limited to chemical etching. Rather, as used herein, "etching" and "etched" can also include, but are not limited to, techniques, such as laser etching/ablation/skiving, grit-blasting (e.g., with sodium bicarbonate or other suitable grit), or the like, that can be employed to expose certain surfaces of the elongated conductive body (e.g., the electroactive surfaces corresponding to a conductive layer or a surface corresponding to an insulating layer).

Achieving accuracy and precision with respect to the particular depth of one or more materials of a coated assembly which are removed by etching can be important. Without precision and accuracy (e.g., for certain embodiments involving an elongated conductive body with a circular or substantially circular cross-section), uniformity of ablation depth may not be achieved, and thus concentricity of the elongated conductive body may be lost. Without achieving and maintaining concentricity with a proximal layer of the elongated conductive body, any subsequent (i.e., distal) layers coated over the proximal layer would also not have concentricity. Loss of concentricity can result in certain portions of the elongated conductive body being thicker than other portions, which in turn, can negatively affect sensor performance (e.g., accuracy).

In some embodiments, the etching process involves etching a single layer of material (e.g., etching only an insulating layer or a conductive layer), but in other embodiments, the etching process involves etching a plurality of layers (e.g., both a conductive layer and an insulating layer), such as two, three, four, five, or more layers. In certain embodiments, portions of the elongated conductive body can be masked prior to depositing the insulating layer in order to maintain an exposed electroactive surface area.

As noted above, in some embodiments, laser ablation is used to remove certain layers that have been deposited on the elongated conductive body. Removal of layers can be performed to expose electroactive surfaces on the elongated conductive body or else merely to remove certain insulating or conductive layers or portions thereof. During the laser ablation process, a laser beam, which can be pulsed and have a particular wavelength and power selected to ablate the desired layers, portions, or patterns, is directed at certain portions of the elongated conductive body to irradiate the layers in accordance with a preselected pattern. The pattern can be controlled by the processor to provide for spacings between the portions of the elongated conductive body that are ablated. In certain embodiments, these spacings are from about 5 mm to about 50 mm, or from about 10 mm to about 30 mm, or even from about 20 mm to about 25 mm.

The power, duration of the laser pulse, repetition rate of the laser pulse, and speed of the laser can be varied to control the speed of the ablation, the amount of material ablated, and the depth of the ablation. The selected ablation settings may depend on the shape, size, and other physical properties of the elongated conductive body. They may also depend on the ablation depth, area, or shape desired. By controlling the parameters described above, the risk of the ablation process leaving a substantial amount of residual ablation debris on the elongated conductive body can be minimized. In some embodiments relating to laser etching of polyurethane, the laser beam has a wavelength of from about 100 nm to about 800 nm, or from about 200 nm to about 300 nm, or from about 220 nm to about 265 nm, or even from about 245 nm to about 250 nm.

In certain embodiments, the elongated conductive body is spun around its longitudinal axis as a laser beam is directed on the elongated conductive body. In further embodiments, the rotation rate is greater than about 0.5 revolutions per second, or greater than about 1 revolution per second, or greater than about 2 revolutions per minute, or greater than about 5 revolutions per minute, or even greater than about 10 revolutions per minute. The laser beam can be generated by any of a variety of laser sources, such as, an excimer laser, YAG laser, CO2 laser, diode laser, for example. The laser beam energy beam density can be established to be sufficient to ablate or remove a layer or portion from the elongated conductive body at a certain predetermined depth and area, but low enough so as to not damage the layers and materials outside the predetermined depth and area. The laser beam energy beam setting can also selected in consideration of the type of material(s) that is the target of the ablation. In some embodiments, the laser ablation process involves directing a beam to remove a small fraction of the total thickness (e.g., a few microns) of a layer with every pulse or pass. Multiple passes are then performed, so that the desired ablated depth is achieved. In certain embodiments, with every pulse or pass, a coating material corresponding to a depth of 0.5 microns from the surface is removed, or a coating material corresponding to a depth of 1 micron from the surface is removed, or a coating material corresponding to a depth of 1.5 micron from the surface is removed, or a coating material corresponding to a depth of 2 microns from the surface is removed, or a coating material corresponding to a depth of 2.5 microns from the surface is removed, or a coating material corresponding to a depth of 3 microns from the surface is removed, or a coating material corresponding to a depth of 5 microns from the surface is removed, or even a coating material corresponding to a depth of 10 micron from the surface is removed.

In certain embodiments, instead of using a single laser beam, multiple laser beams (e.g., two, three, four, or five laser beams) can be distributed around the elongated conductive body. In some of these embodiments, the elongated conductive body may not be configured to rotate during the laser ablation process. Instead, the plurality of laser beams around the elongated conductive body can be configured to turn on simultaneously, sequentially, or in some preselected pattern to remove the desired portion or pattern. A multibeam arrangement can be obtained by using multiple laser sources, or by using one laser source and dividing the laser beam from this source into multiple branches with use of beamsplitters. Each of the smaller beams can then be guided or redirected with individual optical components such as mirrors and lenses, so that the beams are directed to the elongated conductive body from different directions or angles. From this, multiple laser beams can be distributed around a perimeter or circumference of a cross section of the elongated conductive body to remove a layer all around the perimeter or circumference of the elongated conductive body. In alternative embodiments, only certain preselected sections of a perimeter or circumference of the elongated conductive body cross section are removed.

FIG. 7B illustrates one embodiment of the elongated conductive body of FIG. 7A, after it has undergone laser ablation treatment. As shown, a window region 722 is formed when the ablation removes the second and third layers 730, 740, to expose an electroactive surface of the first conductive layer 720, wherein the exposed electroactive surface of the first conductive layer 720 correspond to a working electrode. In the embodiment illustrated in FIG. 7B, the laser ablation treatment of the elongated conductive body is carried out in steps, as evidenced by the multistepped topography. In a first step, a segment of the third layer 740 is ablated, and in a second step, a segment of the second layer 730 is ablated. In this embodiment, the segment of the third layer 740 removed is longer than the segment of the second layer 730 removed. Accordingly, the risk of third layer material falling onto the exposed electroactive surfaces of the first layer 720 may be minimized. Alternatively, in other embodiments, a single step ablation method can be employed, whereby both the second and third layers 730, 740, are removed simultaneously.

Figure 7D:
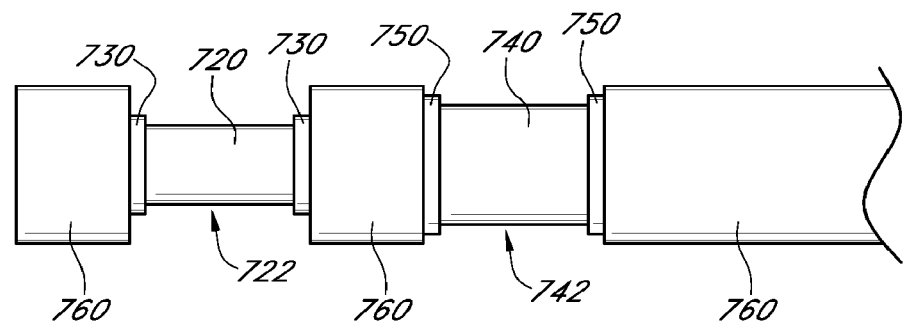
FIG. 7D illustrates the embodiment of FIG. 7C after it has undergone laser ablation treatment.

FIG. 7D illustrates one embodiment of the elongated conductive body of FIG. 7C, after it has undergone laser ablation treatment. Here, two window regions, a first window region 722 and a second window region 742, are formed, with each window region having a different depth and corresponding to a working electrode distinct from the other. As previously described, a multi-step laser ablation treatment can be employed. In forming the first window region 722, in a first step, a segment of the third, fourth, and fifth layers 740, 750, 760 are simultaneously removed. In a second step, a segment of the second layer 730 is removed to expose electroactive surfaces of the first conductive layer 720. As illustrated in FIG. 7D, in this particular embodiment, the segment of the second layer 720 that is removed is shorter than that removed of the third, fourth, and fifth layers 740, 750, 760, to minimize the risk of third, fourth, and fifth layer materials falling onto the exposed electroactive surfaces of the first layer 720. Similarly, in forming the second window region 744, in a first step, a segment of the fifth layer 760 is removed, and in a second step, a segment of the fourth layer 750 shorter than that of the fifth layer 760 is removed.

FIGS. 8B and 8D illustrate the elongated conductive bodies illustrated in FIGS. 8A and 8C, respectively, after they have undergone ablation treatment. As shown in FIG. 8B, the ablation treatment removes portions of the insulator from the elongated conductive body illustrated in FIG. 8A to form a plurality of window regions, thereby exposing a portion of the elongated cores 810A, 810B, and 810C. In this particular embodiment, window region 822A is formed in the insulator such that a portion of elongated 810A is exposed. Similarly, window region 822B is formed in the insulator such that a portion of elongated core 810B is exposed. In other embodiments, the window regions can be staggered and/or non-staggered along the longitudinal length of the sensor.

As shown in FIG. 8D, after ablation treatment, the elongated conductive body illustrated in FIG. 8C is formed with a first window region 822A configured to expose an electroactive portion of the first elongated core 810A and with a second window region 822B configured to expose an electroactive portion of the second elongated core 810B. In some embodiments, the first and second elongated cores are configured to function as first and second working electrodes, respectively, and the third elongated core is configured to function as a reference or counter electrode.

In other embodiments, grit blasting is implemented to expose the electroactive surfaces of an elongated core or conductive layer. This can be performed by using a grit material that is sufficiently hard to ablate the coated material, while being sufficiently soft so as to minimize or avoid damage to the underlying elongated core or conductive layer. Although a variety of "grit" materials can be used (e.g., sand, talc, walnut shell, ground plastic, sea salt, and the like), in some embodiments, sodium bicarbonate can be used as a grit-material because it is sufficiently hard to ablate a certain coating (e.g., a polyurethane, polyimide, or polyethylene insulating layer) without damaging an underlying core (e.g., platinum conductor). One additional advantage of sodium bicarbonate blasting includes its polishing action on certain metals as it strips the polymer layer, thereby potentially eliminating a cleaning step that might otherwise be necessary.

Figure 9A:
FIG. 9A illustrates a recessed region formed with a curved edge.
Figure 9B:
FIG. 9B illustrates a recessed region formed with a sharp edge.

In yet other embodiments, mechanical skiving can be used. Mechanical skiving can involve using a scribe, a high speed grinder, mechanical machining, mechanical wheels, or other tools to impart a recess on the elongated conductive body to expose electroactive surfaces. In some instances, mechanical skiving can be advantageous because mechanical skiving typically results in a recessed region with a curved edge (as illustrated in FIG. 9A), instead of a recessed region with a sharp edge (as illustrated in FIG. 9B), as is typically created by a laser ablation process. In some instances, a recessed region with a curved edge and surface may provide for better control of coating thickness and/or coating thickness profile in the window region.

In yet other embodiments, chemical etching is used to expose the electroactive surfaces. During the chemical etching process, a mask, typically formed of an organic film, is deposited onto selected regions of the elongated conductive body, i.e., the regions not intended to be etched. The sections between the masked regions are then etched, and the mask is subsequently removed.

Pre-Coating Treatment Station

Prior to the coating process, the elongated conductive body 110 can be cleaned to remove organics or other surface contaminants that may interfere with the coating process. It is contemplated that any known suitable cleaning method can be used. For example, in some embodiments, the system uses an ultrasonic cleaning device comprising a cleaning vessel and a roller or pulley, for guiding the elongated conductive body inside the cleaning vessel. During the cleaning process, the cleaning vessel can be filled with a cleaning solvent, such as isopropanol, acetone, tetrahydrofuran (THF), or citric acid, for example. Next, the elongated conductive body is drawn through the cleaning vessel, where it is cleaned by ultrasonic sound waves and the cleaning solvent, such that when the elongated conductive body exits the ultrasonic cleaning device, it is cleaned essentially free of surface contaminants.

In some embodiments, a drying chamber can be provided adjacent to the exit of the cleaning vessel. In these embodiments, as the elongated conductive body exits the drying chamber, it passes through the drying chamber, where residual solvent on the surface can be removed, for example, by evaporating the solvent at a higher rate than that under ambient conditions. Use of a drying chamber can drive out the solvent using any conventional methods known, such as by using heat from an evaporator or an inlet supply of heated inert gas (e.g., nitrogen), or by using vacuum evaporation, for example.

In some embodiments, the elongated conductive body can be cleaned by a plasma device, as an alternative or in addition to the ultrasonic cleaning device. In these embodiments, the elongated conductive body can be treated within a vacuum chamber filled with an inert gas (e.g., Argon), which is electrically charged to bombard the surface of the elongated conductive body with sufficient energy for contaminant removal. The resulting contaminant effluent can then be removed from the drying chamber by a vacuum pump. Because plasma cleaning does not involve chemical reactions, under certain conditions, it may remove certain inorganic contaminants that are not easily removed by ultrasonic cleaning or chemical processes.

In certain embodiments, the elongated conductive body can also undergo surface treatment prior to the coating process to enhance uniformity of the subsequent coating deposition. The surface treatment can be carried out by any of a variety of known techniques. For example, electrostatic charging and/or plasma surface treatment can be used to modify the surface energy of the elongated conductive body. Using ionizing gases such as argon or nitrogen, plasma surface treatment can create highly reactive species even at low temperatures. Typically, only a few atomic layers on the surface are involved in the process, so the bulk properties of the elongated conductive body remain substantially unaltered by the chemistry. In some instances, plasma surface treatment may reduce surface contact angles and provide adequate surface activation for enhanced wetting and adhesive bonding. Other known surface treatments that can be used include, but are not limited to, surface washing with a solvent and corona discharge and UV/ozone treatment.

Coating Station

Figure 3A:
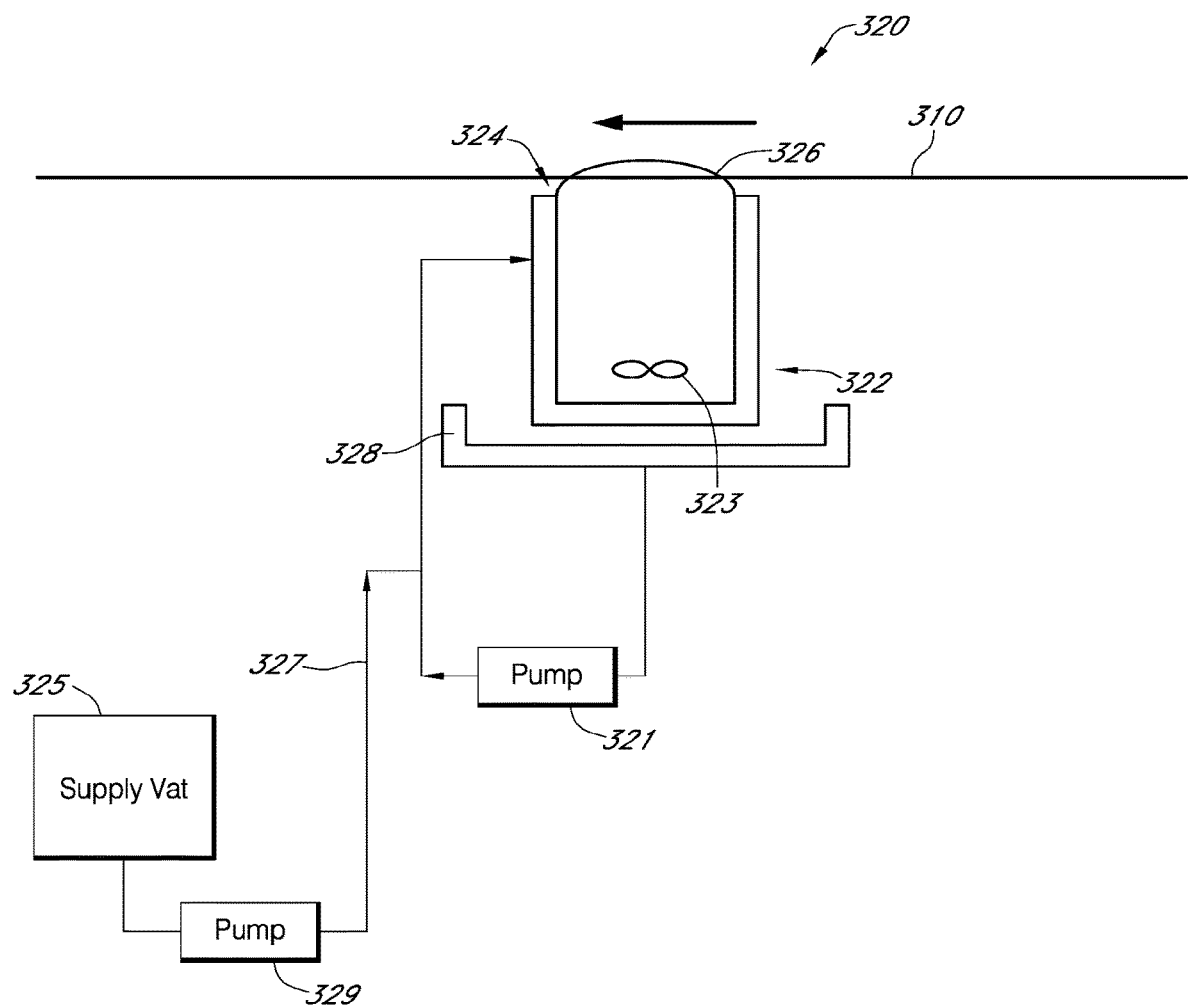
FIG. 3A is a schematic diagram of one embodiment of a coating station.

FIG. 3A provides a schematic diagram of one embodiment of a coating station 320. As the elongated conductive body 310 advances through a meniscus 326 comprising a coating solution formed of a solvent and a coating material, the elongated conductive body's surface becomes immersed in the coating solution. As it separates from the meniscus 326, the elongated conductive body 310 retains a coating with a layer of substantially uniform thickness on its outer surface, as illustrated in FIG. 3B. A solid layer of coating material is then formed on the surface, as the solvent portion of the coating solution evaporates.

As shown in the embodiment illustrated in FIGS. 3A and 3B, the coating station 320 can include a coating vessel 322 with an opening 324 at its top configured for establishing a meniscus 326. The coating vessel 322 can be formed of any of a variety of known inert materials (e.g., ordinary glass or ceramic ware or an inert polymer such as polyethylene) suitable for the coating processes contemplated. In addition, the coating vessel 322 can comprise a collecting section 328 for collecting overflow. In some embodiments, the coating station 320 can comprise an inert gas source, which introduces inert gas (e.g., nitrogen, argon) into the coating station. The inert gas is subsequently removed, so as to purge certain sections of the coating station. It is contemplated that in some embodiments the coating station 320 can also comprise a heat source (e.g., a heat lamp) disposed somewhere near the meniscus to speed solvent evaporation. In some embodiments, the environment in or surrounding the coating station 320 can be controlled. For example, in one system, the coating station 320 can comprise a temperature control unit disposed near or surrounding the coating vessel 322 to control the vapor pressure of the evaporating solvent. Additionally or alternatively, the coating station 320 can also comprise a humidity control unit configured to maintain a relatively constant humidity in the coating station 320. The temperature and humidity inside the coating vessel 320 can each be independently above, below, or substantially the same as the ambient temperature and humidity outside of the coating station 320.

The coating vessel 322 can also comprise various elements for detecting and controlling certain coating solution conditions, such as solids content (also commonly referred to as concentration of coating material), viscosity, and temperature. For example, the coating vessel 322 can include a temperature detector, a coating material concentration detector, a viscosity detector, a heat exchanger, and an agitator (e.g., a stirrer). The processor is operatively connected to detectors configured to transmit signals indicative of certain coating solution conditions to the processor. The processor is also operatively connected to various control elements (e.g., a heater, stirrer, control valve, etc.) that can be used to adjust certain coating solution conditions. Collectively, these various elements and the processor provide a closed-loop feedback mechanism for controlling coating solution conditions.

The embodiments described herein are capable of producing coatings of a precise thickness. This may be achieved in part by controlling certain coating solution conditions, which in turn allows for thickness control of the coating layer deposited onto the elongated conductive body. For example, controlling the temperature of the coating solution may facilitate thickness control, given that certain properties of the coating solution, such viscosity, will vary with temperature changes. As another example, controlling the viscosity may also facilitate thickness control, given that a highly viscous coating solution (e.g., with a high solids content) may sometimes present technical challenges with respect to thickness uniformity. Additionally, inconsistency in the viscosity and solids content of the coating solution between different periods of the coating process may cause inconsistencies in coating thickness between various segments of the elongated conductive body.

During the coating process, a meniscus 326 is established at the opening 324 at the top of the coating vessel 322, by activating the pump 321 which drives the solution to continuously circulate at a precisely controlled rate. To facilitate formation of the meniscus 326, the opening 324 of the coating vessel 322 can have any of a variety of shapes and dimensions, depending in part on the system's preselected process parameters (e.g., the solution used, the temperature of the solution, the speed at which the elongated conductive body advances through the coating station, etc.). For example, in some embodiments, the opening 324 of the coating vessel 322 can be formed with a circular or substantially circular shape, but in other embodiments, the opening can be formed with a shape that resembles an ellipse, a polygon (e.g., triangle, square, rectangle, parallelogram, trapezoid, pentagon, hexagon, octagon), or the like. The coating vessel 322 can also have any suitable dimension. For example, in some embodiments, the coating vessel can have large dimensions, so as to accommodate a plurality (e.g., 3, 4, 5, or 5) of elongated conductive bodies.

To prevent possible agglomeration of coating material particles in the coating vessel 322, the coating vessel 322 can be provided with an agitator 323 (e.g., a stirrer) to ensure that the coating solution is well mixed. The agitator 323 can also be used to prevent possible sedimentation of coating material particles at the bottom of the coating vessel 322. Although not shown in FIG. 3A or 3B, in some embodiments, the coating vessel can be configured to be in fluid communication with a solvent source and a coating material source. During the coating process, if the concentration of the coating material is measured to be outside a preselected range, the processor can respond by making adjustments to various control element setting, for example, by opening a control valve to introduce a solvent or coating material into the coating vessel, to return the coating solution to a preselected concentration.

Referring back to FIG. 3A, in some embodiments, the coating station 320 comprises a supply vat 325 that continuously feeds solution into the coating vessel 322 at a precisely controlled, consistent rate via a line 327 and a pump 329. Accordingly, as the coating process progresses, the solution held in the coating vessel 322 can be continuously replenished from the supply vat 325. By maintaining a controlled, consistent rate of flow of the coating solution from the supply vat 325 to the coating vessel 322, a continuous, consistent overflow flowing out of the opening 324 is sustained. In addition, this flow control may allow for control of the contour and dimensions of the meniscus, which in turn may provide consistency of coating thickness between different segments of the elongated conductive body. Overflow flowing out of the coating vessel can be collected by a collecting section 328, so that the overflow fluid can be further processed, such as, recycled, replenished by combining it with solvent and/or coating material, discarded, etc.

Although not shown, the supply vat 325 can be connected to one or more storage tanks that feed coating material and solvent into the supply vat 325. In some embodiments, the coating solution can be formed of one coating material and one solvent. In these embodiments the supply vat 325 can be connected to one storage tank holding one solvent and another storage tank holding another coating material. In other embodiments, the coating solution can be formed of a plurality of coating materials and/or a plurality of solvents. In these embodiments, the supply vat 325 can be connected to a plurality of storage tanks each holding a different solvent and/or a plurality of storage tanks each holding a different coating material. Similar to the coating vessel 322, the supply vat 325 can also be provided with an agitator (e.g., a stirrer) to agitate the solution and mix the coating material with the solvent, to prevent possible agglomeration of coating material particles in the supply vat 325, and to prevent possible sedimentation of coating material particles at the bottom of the supply vat 325. In some embodiments, the supply vat 325 can include a level indicator for monitoring the level of the coating solution in the supply vat 325. If the fluid level falls below a certain preselected level, the level indicator is configured to transmit a signal to the processor, so that new coating solution can be prepared.

Figure 4A:
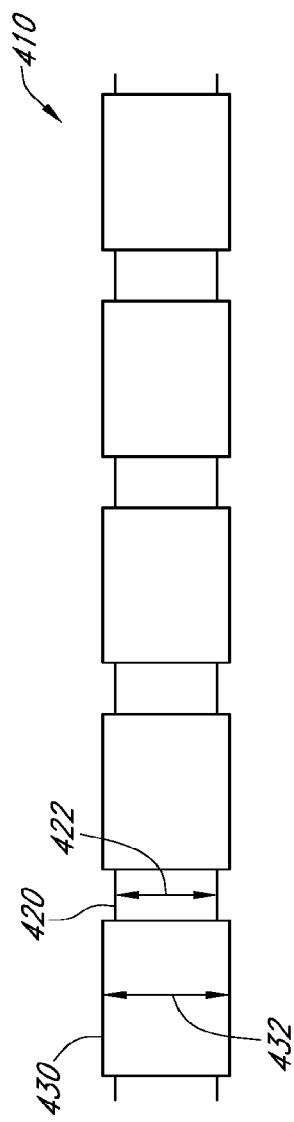
FIG. 4A is side view of an elongated conductive body having portions that are covered by one or more layers of material and portions that are uncovered.

As described elsewhere herein, in some embodiments, the elongated conductive body selected to undergo the membrane coating process may already have been coated with one or more layers of one or more materials (e.g., an elongated core covered with an insulating layer and/or a conductive layer). Following the ablation/etching process described elsewhere herein, as illustrated in FIG. 4A, the surface of the elongated conductive body can have a stepped topography configuration with a plurality of window regions 420, where portions of the insulating and/or conductive layers were previously removed. As shown, the window regions 420 are associated with a diameter 422 (also referred to herein as a window diameter 422) that is less than the diameter 432 associated with the outer surface 430 of the elongated conductive body 410. Because of the stepped topography configuration, controlling the coating thickness on the elongated conductive body 410, particularly the thickness in the window region 420, presents various technical challenges when conventional dip coating techniques are used. The embodiments described herein are configured to overcome these challenges by providing a mechanism that provides precise control of certain process parameters.

Figure 4B:
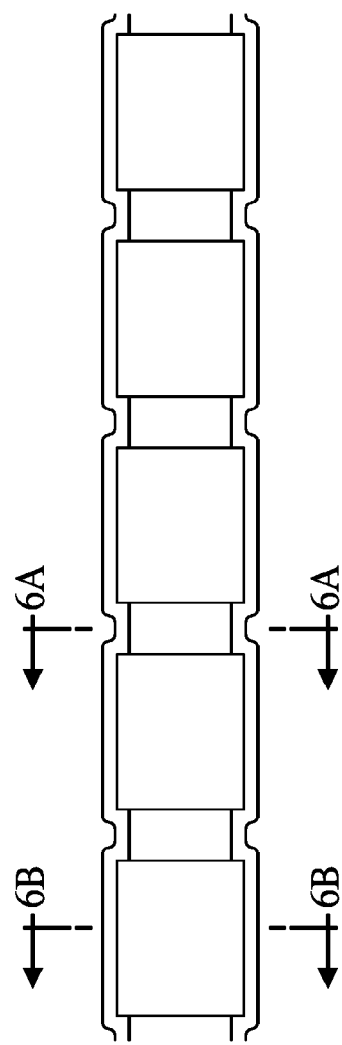
FIG. 4B is a side view of the elongated conductive body of FIG. 4A after it has been coated with a layer of coating material.

As described elsewhere herein, the system may be provided with a thickness control station 130 configured to control the coating thickness of certain portions (i.e., the unetched and/or unablated portions) of the elongated conductive body, by removing excess coating material from its outer surface 430. However, because the dimensions of the die orifice of the thickness control station 130 are constrained by the outer diameter of the elongated conductive body, a different mechanism can be used to control the coating thickness and thickness profile of the window regions 420. As illustrated in FIG. 4B, depositing a coating onto a windows region 420 with a stepped topography may result in a coating thickness profile resembling a curve. By controlling certain process parameters, the embodiments described herein allow for precise control over the thickness and the thickness profile of the layers residing in the window regions. To achieve this control, in some embodiments, the meniscus coating process described herein can be used, whereby the viscosity of the coating solution, the solids content of the coating solution, the temperature of the coating solution, the speed at which the elongated conductive body advances through the coating station, and/or the flow rate of the coating solution into the coating vessel are precisely controlled. Each of the aforementioned process parameters affects the thickness and the thickness profile of the material coated on the elongated conductive body. Because the thickness of the coating directly affects certain properties (e.g., permeability of the membrane system) of the continuous analyte sensor, achieving tight control of the thickness may also provide for tight control of these properties.

The coating thickness and the uniformity of the thickness may be controlled by solvent selection. Depending on the application contemplated, any of a variety of solvents can be used, each of which is associated with a vapor pressure. The vapor pressure of a solvent affects the rate at which the solvent evaporates. Accordingly, solvent selection may affect the thickness and/or thickness control.

Control of the viscosity can involve selection of a polymer forming the coating material, molecular weight selection for the polymer, control of polymer concentration of the solution, and solution temperature control. With a low viscosity, a coating may sometimes considerably sag to the bottom surface of the elongated conductive body, resulting in a variable layer thickness. In contrast, with a high viscosity, the coating material may be difficult to coat onto the elongated conductive body. Accordingly, it is contemplated that the system can use a coating solution with an appropriate viscosity which will allow for deposition, but will yet still provide for control over coating thickness and thickness profile. The molecular weight of a polymeric coating material may also affect the viscosity of the coating solution, with viscosity generally increasing with molecular weight. Viscosity also often correlates with temperature. Thus, in some embodiments, the temperature of the coating solution may be controlled so that the viscosity may be controlled. In some embodiments, the coating solution is controlled to have a preselected viscosity of from about 0.1 to about 500 cP, or from about 1 to about 30 cP, or from about 50 to about 100 cP.

Control of the solids content of the coating solution may be achieved by preparing a coating solution with a preselected concentration level, and sustaining this concentration level by constantly monitoring the concentration and adjusting as needed. In some embodiments, the coating solution is controlled to have a preselected solids content of from about 0.1 to about 60 weight percent, or from about 1 to about 35 weight percent, and or from about 5 to about 20 weight percent.

Control of the coating solution temperature may be achieved by use of a thermistor and a heating element (e.g., a heat exchanger). In some embodiments, the coating solution is controlled to have a preselected temperature from about 20° C. to about 100° C., and or from about 22° C. to about 35° C.

Control of the speed at which the elongated conductive body advances through the coating station can be controlled by the motor of the transport mechanism. Generally, a slower rate of withdrawal from the meniscus results in a thicker coating along the surface of the elongated conductive body. In some embodiments, the elongated conductive body may be controlled to have a rate of advancement from about 1 inch/min to about 1,000 ft/min, and or from about 1 ft/min to about 50 ft/min.

Control of the flow rate of the coating solution into the coating vessel may be achieved by controlling the output from the one or more pumps that pump coating solution into the coating vessel. In some embodiments, the flow rate into the coating vessel is from about 1 mL/min to about 25 mL/sec, and or from about 3 mL/min to about 7 mL/min.

Figure 3C:
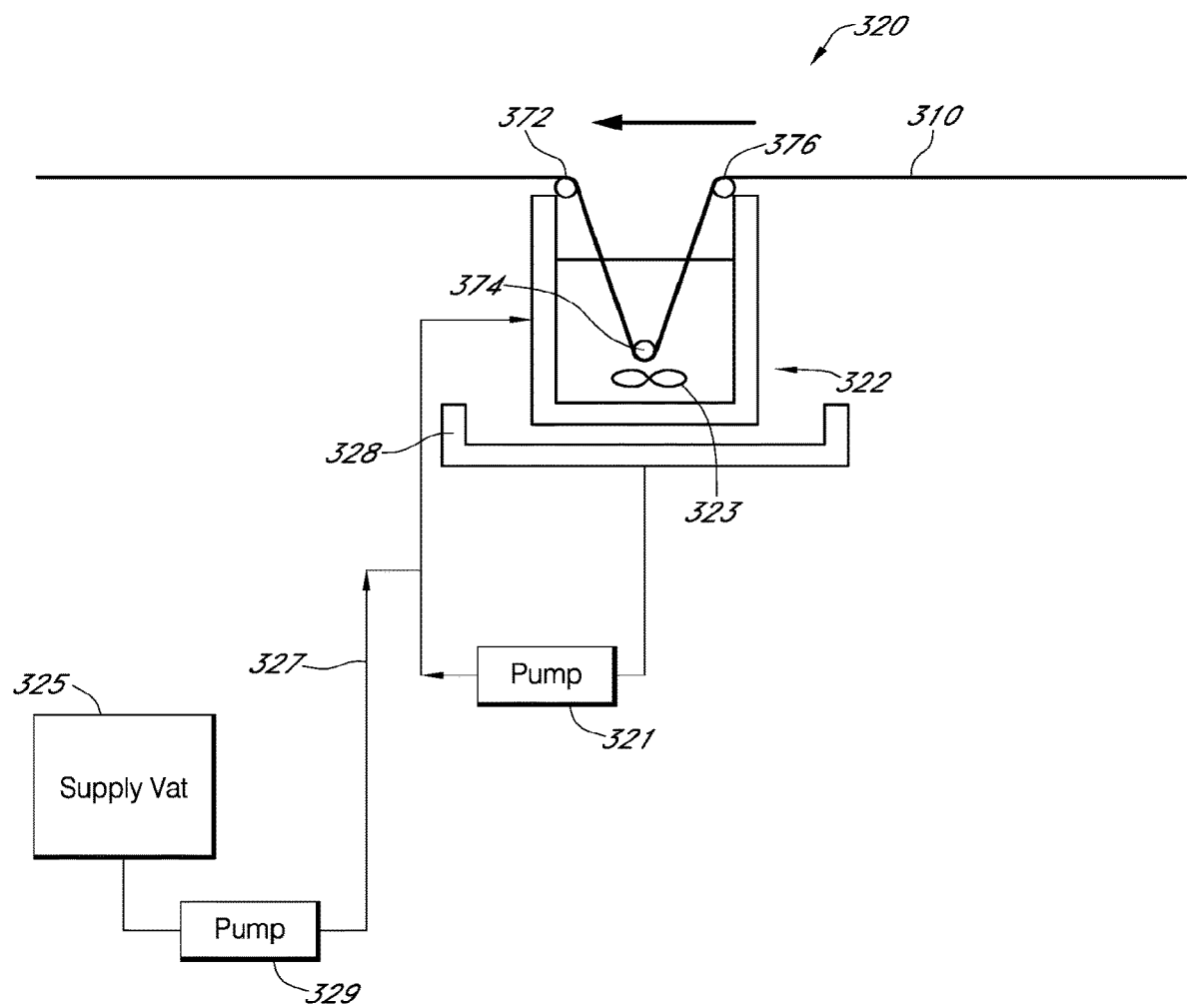
FIG. 3C is a schematic diagram of another embodiment of a coating station.

Although a meniscus coating process is used coat the elongated conductive body in some embodiments, it is contemplated that in other embodiments, other types of coating processes can be used as an alternative or in addition to the meniscus coating process. For example, as illustrated in FIG. 3C, in some embodiments, instead of being configured to advance through a meniscus, the elongated conductive body 310 can be configured to advance into the coating vessel 322, where it can dwell for a preselected period of time. A plurality of rollers or pulley 372, 374, 376 can be disposed near or in the coating vessel 322 to provide guidance to the elongated conductive body 310 as it advances along its predetermined path. By precisely controlling certain process parameters, the embodiment of the system illustrated in FIG. 3C may be capable of achieving the thickness control characteristics associated with the meniscus coating process described elsewhere herein.

Figure 3D:
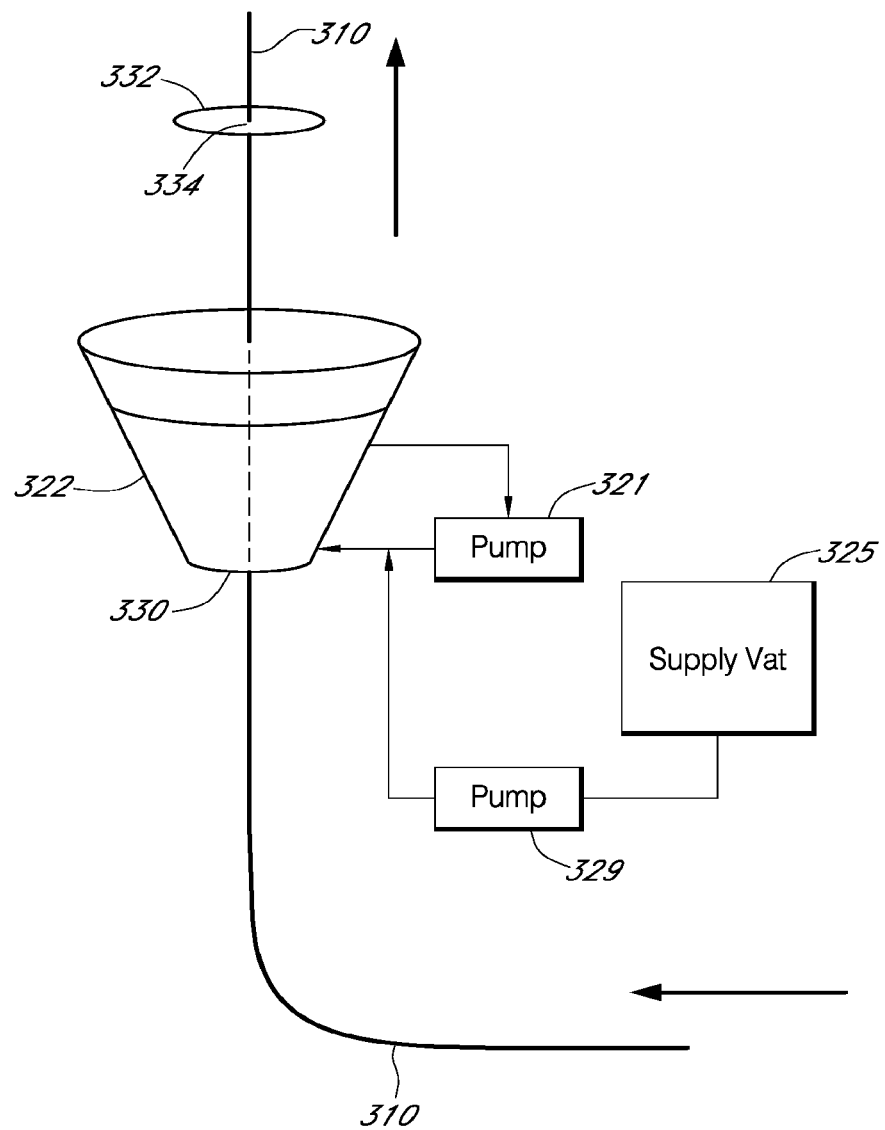
FIG. 3D is a schematic diagram of yet another embodiment of a coating station.

In yet other embodiments, a coating process employing a vertical arrangement is employed. For example, as illustrated in FIG. 3D, in some embodiments, the elongated conductive body 310 can be advanced vertically upwards through a septum 330 disposed at the bottom of a coating vessel 322, through the coating vessel 322, whereupon the elongated conductive body 310 is coated with the coating solution, and then through a thickness control device (e.g., a die 332 with an orifice 334) whereby excess coating material is removed. The septum can comprise a sealing member (e.g., a gasket or a plenum) for preventing the coating solution from leaking out of the bottom of the coating vessel 332. In these particular embodiments, the excess coating material falls back into the coating vessel 322. Similar to other embodiments described herein, the coating vessel 322 of these embodiments can be connected to a pump 321 for circulating the coating solution and a supply vat 325 for feeding coating solution into the coating vessel 322. In further embodiments, the coating vessel 322 can be equipped with a level indicator for monitoring the level of the coating solution therein. If the fluid level falls below a certain preselected level, the level indicator is configured to transmit a signal to the processor, so that additional coating solution is drawn from the supply vat 325 to the coating vessel 322 via pump 329.

Although the methods and systems described herein relate to dip coating processes, it should be understood that the coating station can employ any of a variety of other types of coating processes, such as spray coating or vapor deposition. For example, in one embodiment, the elongated conductive body is advanced through a spraying tunnel. While passing through the spraying tunnel, the elongated conductive body is coated with a coating material, which can be applied using any of a variety of known spray coating techniques, such as fog spraying or electrostatic spraying, for example. In another embodiment, a continuous manufacturing process is contemplated that utilizes physical vapor deposition to deposit a coating material. Physical vapor deposition can be used to coat one or more layers of material onto the elongated conductive body. It is contemplated that in some instances, employing physical vapor deposition to coat the elongated conductive body may result in consistent deposition and enhanced reproducibility.

Figure 3E:
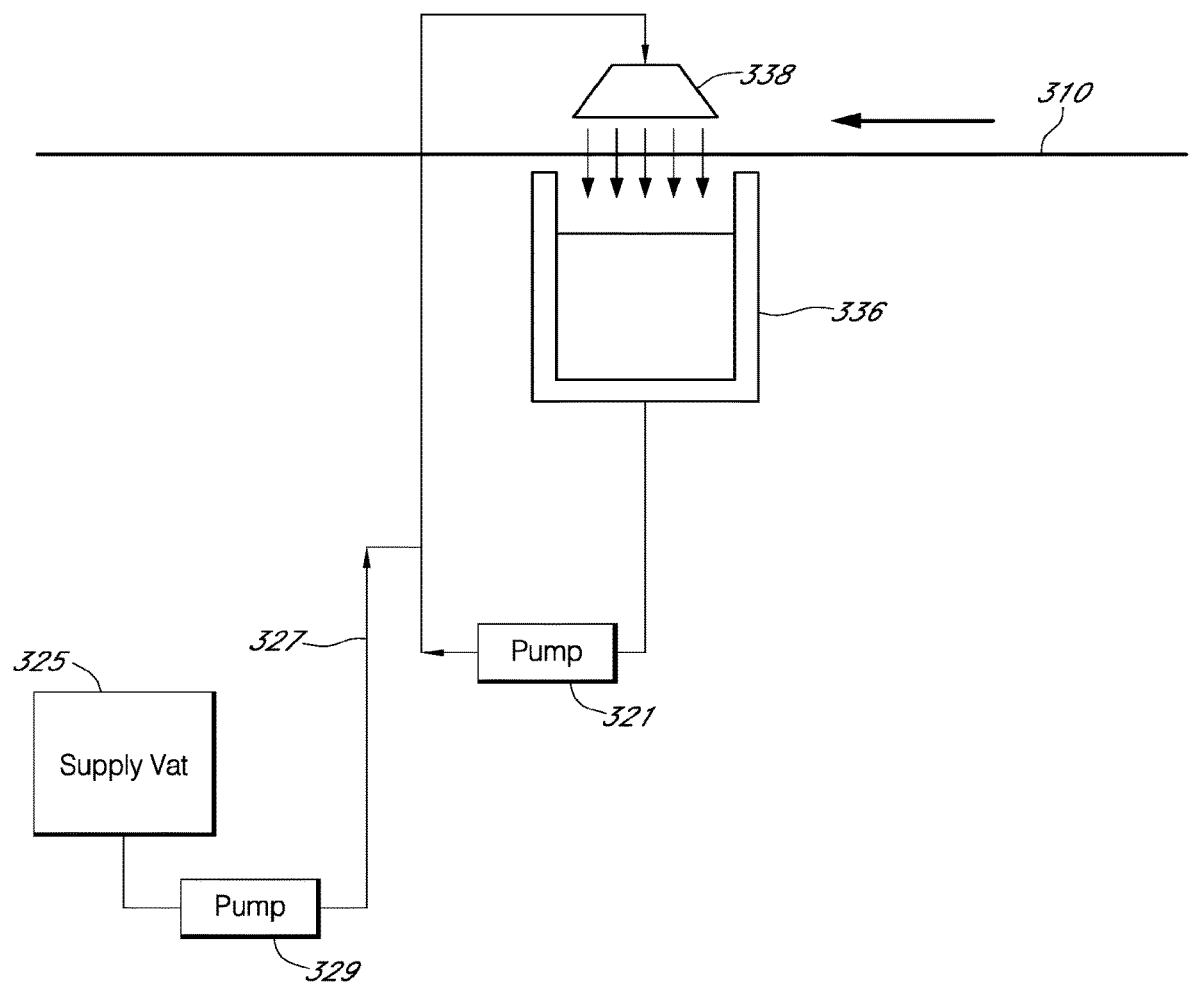
FIG. 3E is a schematic diagram of yet another embodiment of a coating station.

FIG. 3E illustrates one embodiment of a coating station that employs spray coating. Similar to some of the other embodiments described herein, in this particular embodiment, the coating station comprises a circulation pump 321 and a supply vat 325 configured to feed coating solution via a pump 329. In addition, this embodiment also comprises a nozzle 338 for spraying a coating solution and a receiving container 336 for collecting coating solution. During operation, as the elongated conductive body 310 is advanced through the coating station, it is sprayed with a jet of coating solution from the nozzle 338. Coating solution that falls off of the elongated conductive body is collected by the receiving container 336. From there, the coating solution is pumped via circulation pump 321 to the nozzle 338. In some embodiments, periodically (e.g., when the amount of coating solution in the receiving container 336 is low) coating solution from the supply vat 325 can also be pumped into the nozzle 338 via pump 329. In further embodiments, a plurality of nozzles can be provided at various angles and positions with respect to the pathway of the elongated conductive body, so as to spray the elongated conductive body with jets of coating solution from multiple positions and angles (e.g., from an angle that directs coating solution at the underside of the elongated conductive body).

Figure 3F:
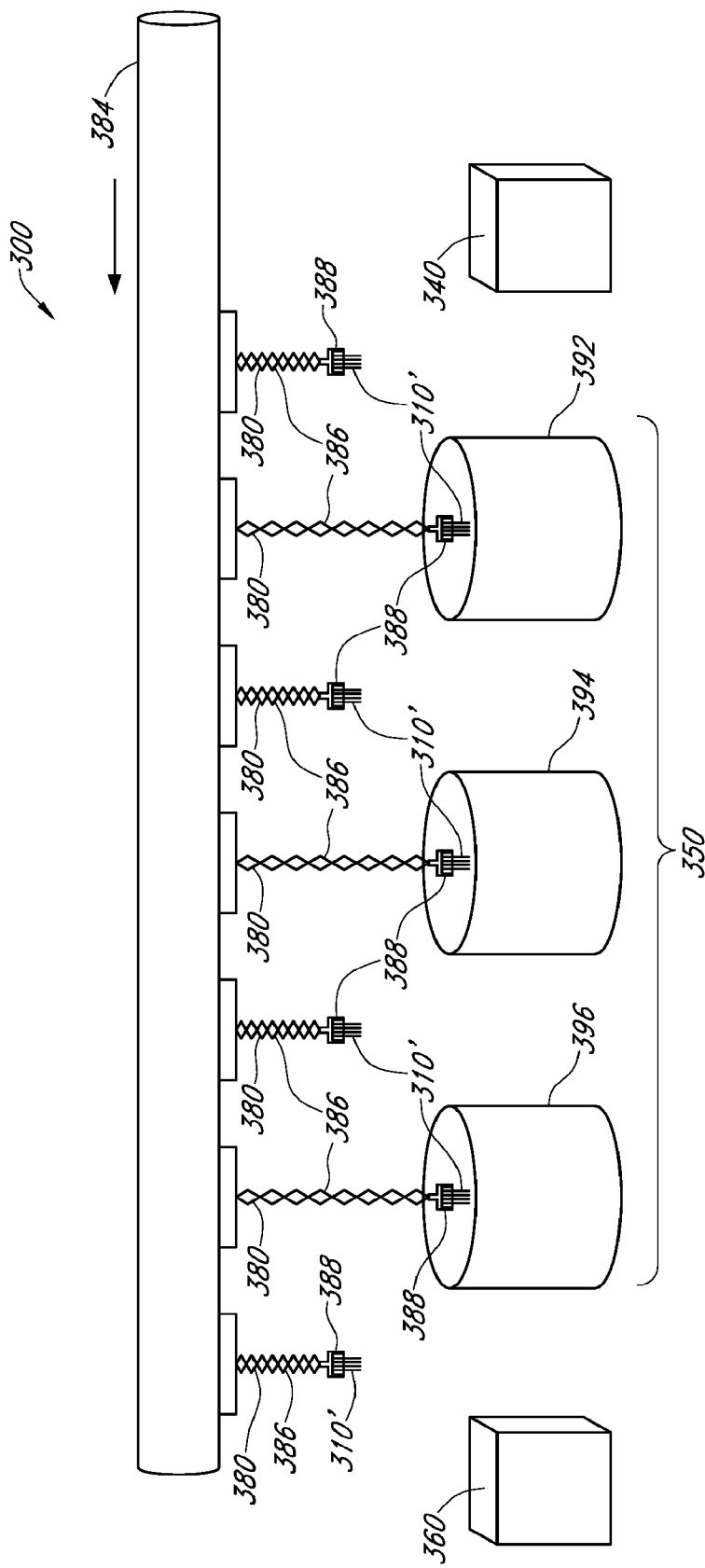
FIG. 3F is a schematic diagram of yet another embodiment of a coating station.

While the transport mechanisms illustrated in FIGS. 3A-3E involve a reel-to-reel system for moving a long, continuous strand of elongated conductive body 310 for coating, in other embodiments, the elongated conductive body being coated may be in the form of individual pieces 310', e.g., pieces formed after a singulation process whereby a long, continuous strand of elongated conductive body 310 is cut into individual pieces 310'. FIG. 3F illustrates one embodiment of a transport mechanism that can be used to move elongated conductive bodies 310' that are in the form of individual pieces. In the embodiment shown in FIG. 3F, the transport system 300 includes a conveyor that supports a plurality of robotic units 380. Each robotic unit 380 comprises a retractable arm 386 secured to the conveyor 384. The retractable arm 386 comprises an elongated conductive body holder 388 that supports the elongated conductive body 310'. Although in the embodiment illustrated in FIG. 3F, the elongated conductive body holder 388 is shown holding four elongated conductive bodies 310', in alternative embodiments, an elongated conductive body holder capable of holding any other number of elongated conductive bodies 110' may be used instead. As the retractable arm 386 is extended, the elongated conductive body 310' is moved downwards, and the elongated conductive body 310' is partially or wholly submerged in a coating solution. After a predetermined time, the retractable arm is retracted, and the elongated conductive body 310' is pulled out of the coating solution. The elongated conductive body 310' is then allowed to dry as the solvent of the coating solution evaporates. Although not shown, a heater or dryer may be disposed along the path of the conveyor or on the robotic unit to accelerate evaporation of the coating solution.

As shown in FIG. 3F, the conveyor 384 is designed to advance the elongated conductive body 310' from one coating vessel 392 to another coating vessel 394, and then to another coating vessel 396. Additionally, the conveyor 384 is designed to advance the elongated conductive body 310' from one station 340 to a coating station 350, and then to another station 360. Although with the transport system 300 shown in FIG. 3F, the conveyor 384 is shown moving the elongated conductive body 310' between three stations (including the coating station 350) and three coating vessels, it should be understood that in other embodiments, the conveyor 384 may be configured to move elongated conductive body 310' between any number of coating vessels and any number of stations.

Figure 3I:
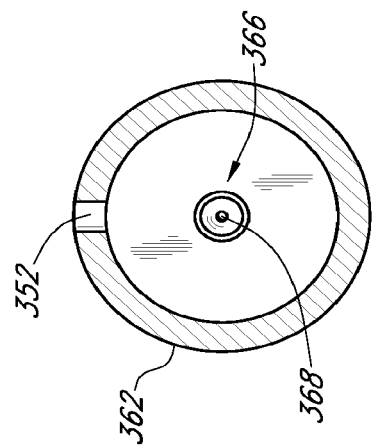
FIG. 3I provides a view of the coating chamber illustrated FIG. 3G on lines 3I-3I.
Figure 3H:
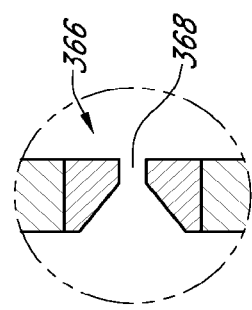
FIG. 3H is a close side view of the die illustrated in FIG. 3G.
Figure 3G:
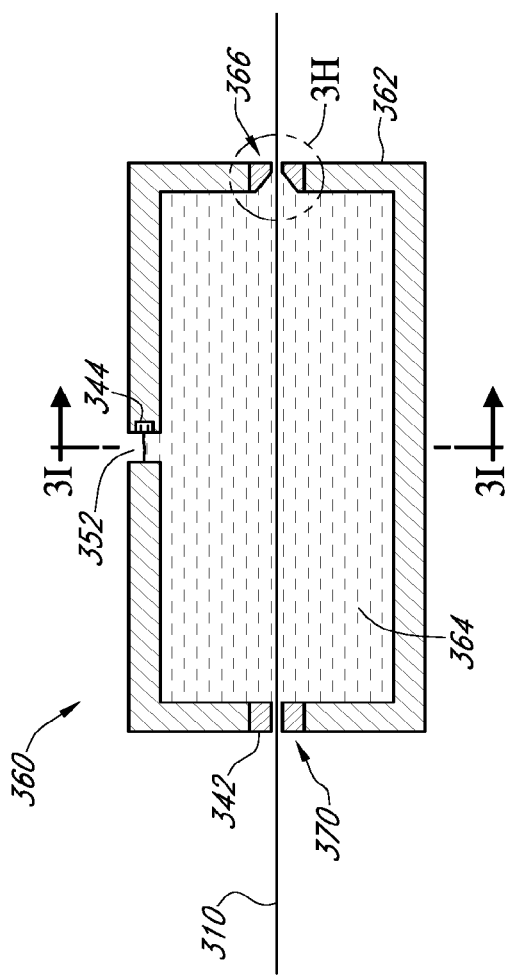
FIG. 3G is a schematic diagram of an embodiment of a coating station comprising a coating vessel with a die.
Figure 3J:
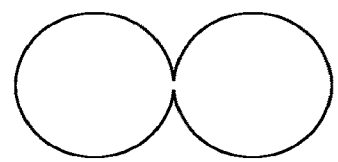
FIG. 3J illustrates various examples of cross-sectional shapes of a die orifice.
Figure 3J:
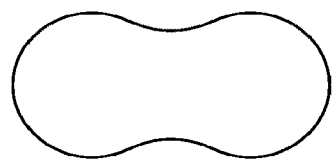
Figure 3J:
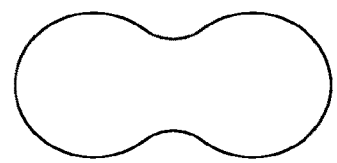
Figure 3J:
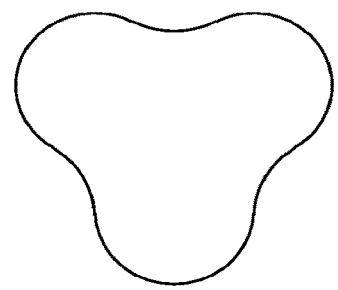
Figure 3J:
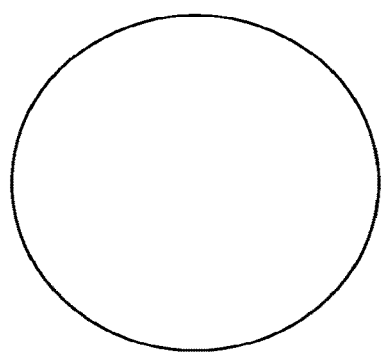
Figure 3J:
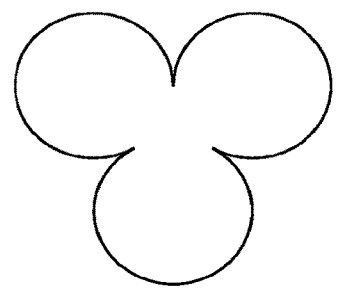
Figure 3J:
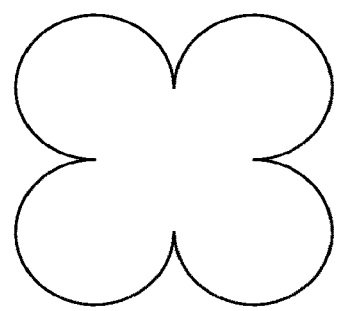
Figure 3J:
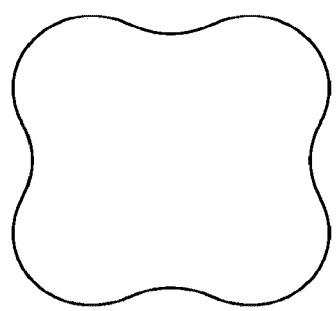
Figure 3J:
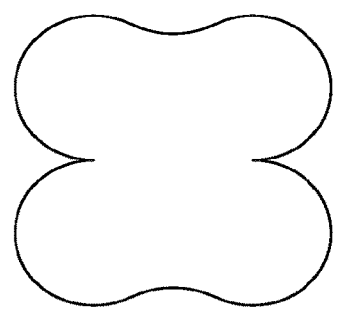

In certain embodiments, the step of depositing a coating material on the elongated conductive body and the step of controlling the thickness of the coating can be combined. For example, referring to FIG. 3G, a coating chamber 360 is shown that includes both a coating vessel 362 for holding a coating solution 364 and a die 366 (e.g., a diamond die) with an orifice 368 configured to control the coating thickness of the elongated conductive body 310 as it exits the coating chamber 360. FIG. 3H is a close side view of the die 366 and illustrates a tapering mechanism of the die. The coating solution 364 may comprise a solvent and a coating material, such as a conductive material (e.g., platinum, Ag/AgCl, etc.), an insulating material (e.g., polyurethane, polyimide, polyethylene), or a membrane material (e.g., a material used to form the electrode layer, enzyme layer, diffusion resistance layer, interference layer, etc.) FIG. 3I provides a view of the coating chamber 360 on lines 3I-3I of FIG. 3G. It has been found that the tapering mechanism illustrated in FIG. 3H facilitates a certain fluid dynamic that keeps the elongated conductive body centered along the longitudinal axis of the die orifice 368. FIG. 3J illustrates various other non-limiting examples of cross-sectional shapes of the die orifice 368 that can be used to mold the elongated conductive body to a desired shape. It should be understood that the die 366 can not only be used to coat an elongated conductive body formed of a single core or an elongated conductive body formed of a plurality of cores, but that it can also simultaneously coat a plurality of elongated conductive bodies in parallel.

The entrance passage of the coating chamber 360 includes an opening 370 that permits the elongated conductive body 310 to pass therethrough. A sealing member 342 is used to prevent the coating solution from leaking out of the opening 370. The sealing member 342 may be any of a variety of seals capable of preventing or reducing liquid leakage. Seals that can be used include, for example, o-rings, hydraulic seals, polypak seals, quad rings, radial shaft seals, v-ring seals, and the like. The coating chamber 360 may include an opening 352 for introduction of the coating solution into the coating vessel 362. Although the coating solution is shown in FIG. 3G as being introduced from the top of the coating vessel 362, it should be understood that in other embodiments the coating solution may be introduced into coating vessel from other entry points (e.g., from the side or bottom of the coating vessel) and by using various other mechanisms (e.g., via a conduit connected to a pump and a storage tank). The coating chamber 360 may also include a level indicator 344 that communicates with a control system, so that a predetermined level of coating solution 364 in the coating chamber 360 is maintained.

In some embodiments, the system is capable of depositing a coating layer having a substantially uniform thickness along the outer surface 430 of the elongated conductive body, wherein the thickness is less than about 35 microns, or less than about 25 microns, or less than about 10 micron, or less than about 5 microns, or less than about 1 microns, or even less than 0.1 microns. In some embodiments, the thickness uniformity of the outer diameter is better than about ±50% of the average thickness, or better than about ±30%, or better than about ±10%, or better than about ±5%, or even better than about ±1%. In some embodiments, the coefficient of variation of the outer diameter thickness is less than about 0.2, or less than about 0.1, or less than about 0.07, or less than about 0.05, or less than about 0.02, or even less than about 0.01.

In addition to being capable of depositing a coating layer having a substantially uniform thickness along the outer surface of the elongated conductive body, the system is also capable of depositing a coating layer with a thickness profile that is substantially uniform among the plurality of window regions 420 of the elongated conductive body. More specifically, in some embodiments, the coating layer deposited onto each window region can have a thickness profile that is consistent with those of the other window regions of the elongated conductive body.

To determine thickness profile uniformity, the mean coating thickness of each window region can be measured and compared with those of the other window regions. In some embodiments, wherein the elongated conductive body comprises 10 or more window regions, the coefficient of variation (of the 10 or more window regions) of the mean coating thickness is less than about 0.5, or less than about 0.2, or less than about 0.1, or less than about 0.05, or even less than about 0.01.

Thickness profile uniformity may also be determined by measuring coating thickness at certain locations (e.g., at a first distance one fifth from one end of the window region, at a second distance two fifths from one end of the window region, etc.) inside each window region, and comparing it with other window regions. In certain embodiments, wherein the elongated conductive body comprises 10 or more window regions, the coefficient of variation (of the 10 or more window regions) of the coating thickness at a first distance one fifth from one end of each of the 10 or more window regions is less than about 0.3, or less than about 0.2, or less than about 0.1, or still less than about 0.05, or even less than about 0.01. In certain embodiments, wherein the elongated conductive body comprises 10 or more window regions, the coefficient of variation (of the 10 or more window regions) of the coating thickness at a second distance two fifths from one end of each of the 10 or more window regions is less than about 0.3, or less than about 0.2, or less than about 0.1, or still less than about 0.05, or even less than about 0.01. In certain embodiments, wherein the elongated conductive body comprises 10 or more window regions, the coefficient of variation (of the 10 or more window regions) of the coating thickness at a third distance three fifths from one end of each of the 10 or more window regions is less than about 0.3, or less than about 0.2, or less than about 0.1, or still less than about 0.05, or even less than about 0.01. In certain embodiments, wherein the elongated conductive body comprises 10 or more window regions, the coefficient of variation (of the 10 or more window regions) of the coating thickness at a fourth distance fourth fifths from one end of each of the 10 or more window regions is less than about 0.3, or less than about 0.2, or less than about 0.1, or less than about 0.05, or even less than about 0.01. In certain embodiments, wherein the elongated conductive body comprises 10 or more window regions, the coefficient of variation (of the 10 or more window regions) of the coating thickness at a midpoint between two ends of each of the 10 or more window regions is less than about 0.3, or less than about 0.2, or less than about 0.1, or less than about 0.05, or even less than about 0.01.

By providing the capability of achieving a substantially uniform thickness profile among the plurality of window regions and a substantially uniform thickness along the outside surface of the elongated conductive body, the embodiments also provide the capability of achieving substantial uniformity with respect to certain sensor properties, such as sensitivity and current density. For example, in some embodiments, wherein the elongated conductive body comprises 10 or more window regions, the coefficient of variation (of the 10 or more window regions) of in vivo sensor sensitivity and/or in vitro sensor sensitivity at about 100 mg/dL glucose concentration is less than about 0.5, or less than about 0.25, or less than about 0.1, or less than about 0.05, or even less than about 0.01. In certain embodiments, wherein the elongated conductive body comprises 10 or more window regions, the coefficient of variation (of the 10 or more window regions) of in vivo sensor current density and/or in vitro sensor current density at about 100 mg/dL glucose concentration is less than about 0.5, or less than about 0.25, or less than about 0.1, or less than about 0.05, or even less than about 0.01.

Figure 3K:
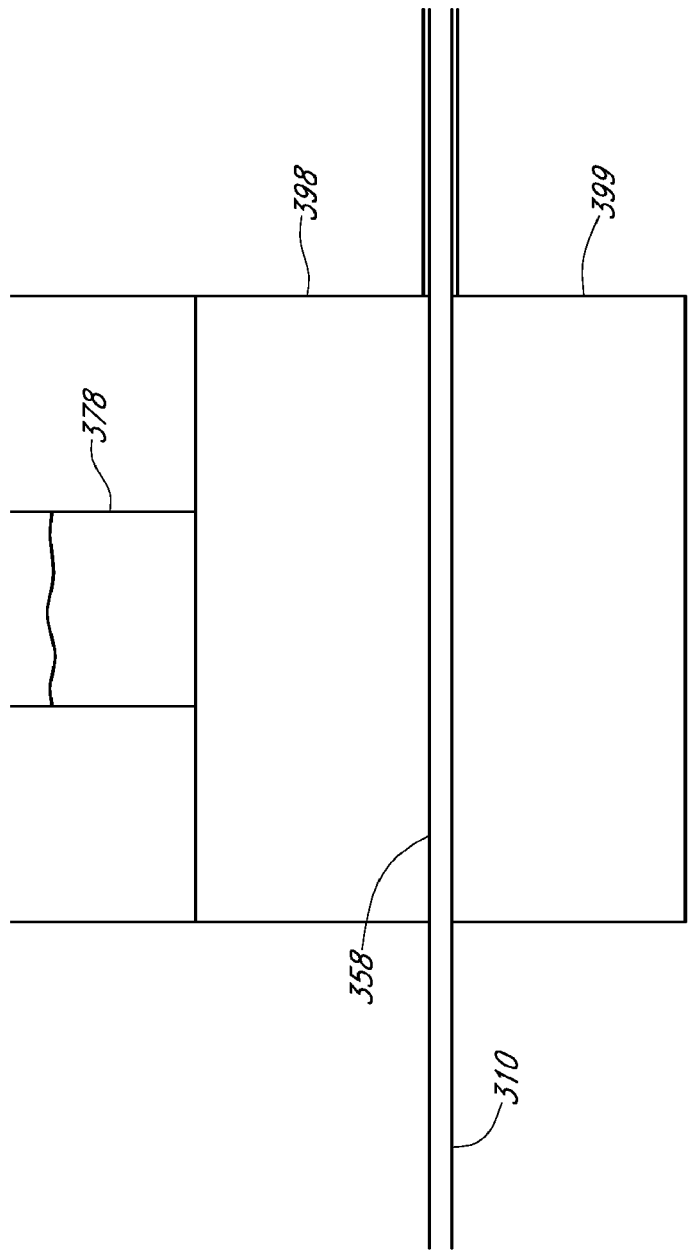
FIG. 3K is a schematic diagram of yet another embodiment of a coating station.

Although certain thickness control mechanisms (e.g., die, a gas knife, etc.) are described elsewhere herein for controlling the thickness of the coating applied onto the elongated conductive body, it is contemplated that in some embodiments these control mechanism may not be necessary. FIG. 3K illustrates one embodiment of a coating device 390 comprising two absorption pads 398, 399 that are soaked with a solution comprising the coating material. One or more of absorption pads may be in communication with a reservoir 378 holding a solution with the coating material. In this particular embodiment, the two absorption pads are arranged in an abutting relationship, such that as the elongated conductive body is advanced in a path along a plane defined by the interface between the two absorption pads. The solution with the coating material is applied to the elongated conductive body. By controlling the concentration gradient that exists at the interface 358, the amount of coating that is applied to the elongated conductive body 310 can be controlled. Other ways of controlling the thickness of the elongated conductive body include, but are not limited to, controlling the surface energy of the elongated conductive body, controlling the speed at which the elongated conductive body is advanced, and controlling the viscosity of the solution comprising the coating material. Accordingly, with multiple passes through the coating device 390, an elongated conductive body 310 with a certain preselected thickness of a coating material can be obtained. The pads may be formed of any material, such as a fibrous material, that is capable of absorbing the solution. In addition, although the embodiment illustrated in FIG. 3K includes two absorption pads, it should be understood that in other embodiments, a different number of absorption pads (e.g., three, four, five, ten, or more) having the same or different shapes or dimensions can also be used.

Thickness Control Station

Referring back to FIGS. 1A-1D, After advancing through the coating station 120, the elongated conductive body 110 is then advanced to a thickness control station 130. In some embodiments, the thickness control station 130 comprises a die (not shown) mounted transverse to the elongated conductive body. As the elongated conductive body advances through an orifice of the die, excess coating material is removed to form on the treated surface a coating layer having a substantially consistent thickness. As described above, the excess coating material removed is from the outer surface 430 of the elongated conductive body, and not from the window surface 420. The dimensions of the die orifice can vary depending on the type of coating being formed on the elongated conductive body. With respect to the coating process involving the insulating layer, the die orifice can have a radius of from about 0.1 to about 25 microns larger than that of the elongated conductive body without the insulating layer, or from about 5 to about 15 microns larger, or even from about 10 to about 14 microns larger. With respect to the coating process involving the conductive layer, the die orifice can have a radius of from about 0.1 to about 25 microns larger than that of the elongated conductive body without the conductive layer, or from about 1 to about 15 microns larger, or even from about 5 to about 10 microns larger. With respect to the coating process involving the electrode layer, the die orifice can have a radius from about 0.1 to about 25 microns larger than that of the elongated conductive body without the electrode layer, or from about 0.2 and 10 microns larger, or even from about 0.5 to about 1.5 microns larger. With respect to the coating process involving the interference layer, the die orifice can have a radius of from about 0.1 to about 25 microns larger than that of the elongated conductive body without the interference layer, or from about 0.2 to about 10 microns larger, or even from about 0.5 to about 1.5 microns larger. With respect to the coating process involving the enzyme layer, the die orifice can have a radius of from about 0.1 to about 25 microns larger than that of the elongated conductive body without the enzyme layer, or from about 0.2 to about 10 microns larger, or even from about 0.5 to about 1.5 microns larger. With respect to the coating process involving the diffusion resistance layer, the die orifice can have a radius of from about 0.1 to about 25 microns larger than that of the elongated conductive body without the diffusion resistance layer, or from about 1 to about 15 microns larger, or even from about 5 to about 10 microns larger.

While in some embodiments the die orifice has a circular or substantially circular shape, in other embodiments the die orifice can have a shape that is oval, square, rectangular, triangular, polyhedral, star-shaped, C-shaped, T-shaped, X-shaped, Y-Shaped, irregular, or the like.

In some embodiments, the thickness control station can comprise a plurality of dies, each or some of which comprise an orifice with a shape or dimension different from that of the other dies. For example, in one embodiment, the thickness control station can comprise three dies arranged in a series, with each die comprising a circular orifice, wherein a first die orifice comprises a larger diameter than that of a second die, and the second die orifice comprises a larger diameter than that of a third die. Alternatively, in some embodiments, the thickness control station can comprise one die with a plurality of orifices formed therein, with each orifice configured to receive an elongated conductive body.

In one embodiment, the die can comprise a plurality of movable members configured to collectively define the outline of an orifice, through which the elongated conductive body is configured to advance. The movable members can be controlled by the processor to move to different positions and arrangements to form orifices of different shapes and dimensions. This feature provides the system with the capability to adjust the shape and dimension of the orifice to conform to certain preselected process parameters (e.g., preselected shape or thickness of the elongated conductive body). In some embodiments, to make certain that the elongated conductive body is centered with respect to its entry into the die orifice, guide rollers or pulleys can be disposed near the entrance and/or exit of the die, to provide precise guidance to the moving elongated conductive body.

As the process progresses, a buildup of coating material may form in the region of the orifice. To remove this buildup, the thickness control station can include a solvent source that periodically or continuously sends solvent to the orifice. In some embodiments, the thickness control station can comprise a pan for collecting excess coating material that falls from the elongated conductive body or the die. The excess coating material may be discarded or reused if suitable.

In addition to the die described above, it is contemplated that other known techniques for removing excess coating material can also be used. For example, in some embodiments, as an alternative or in addition to the die, a gas knife, using impinging jets of inert gas (e.g., nitrogen) can be used.

Drying or Curing Station

As shown in FIG. 1A, the system 100 comprises a drying or curing station 140 for drying and curing the coating material deposited onto the elongated conductive body 110. As the elongated conductive body 110 advances through the drying/curing station 140, residual solvent on the surface of the elongated conductive body 110 is evaporated. Furthermore, crosslinkable components of the coating material can be substantially crosslinked. The curing process can be carried out by any of a variety of conventional drying techniques, such as by UV, infrared, microwave, x-ray, gamma ray, or electron beam radiation, whereby radiation is directed at the coating material, or alternatively by heat, such as by conduction drying or convection drying, for example, by hot air convection drying using a hot air convection oven. Depending in part on the particular coating material used and the coating thickness, one or more of the above-mentioned techniques may be used as an alternative (or in addition) to other techniques. For example, while not wishing to be bound by theory, it is believed that a high energy radiation curing mechanism (e.g., short wavelength UV) may sometimes be used when the deposited layer is thick, because high energy radiation typically penetrates coating material better than infrared light, and thus may provide more curing uniformity along the entire thickness of the coated material. Radiation-based curing may also be used in some embodiments because it provides tight control over the level of radiation, thereby allowing for better control of the curing process. The curing process may take place under a variety of process conditions. In one embodiment, the drying or curing process occurs in a curing chamber and/or oven at a temperature of from about 20° C. to about 500° C., or from about 50° C. to about 150° C., or even from about 200° C. to about 400° C. In some embodiments, the system can include a humidifier/dehumidifier for maintaining proper relative humidity in the drying/curing station.

Thickness Measurement Station

Referring back to the embodiment illustrated in FIG. 1A, the system 100 includes a thickness measurement station 150 comprising a thickness measurement sensor or micrometer configured for measuring the thickness of the elongated conductive body 110 (with or without coating), as it passes through the thickness measurement station 150. After obtaining a reading, the micrometer is configured to transmit to the processor 160 a signal indicative of the measured thickness. If the measured thickness is determined to be less than the preselected thickness, the system is configured to repeat the coating process until a layer having the preselected thickness is formed.

It is contemplated that the thickness measurement sensor or micrometer can be any of a variety of devices capable of measuring a dimension indicative of a thickness of a coating formed on the elongated conductive body. For example, in some embodiments, the micrometer can be an optical micrometer, but in other embodiments the micrometer can be a gauge device or other similar device configured to contact the elongated conductive body for thickness measurement. Optical micrometers that can be used include light emitting diode (LED) devices, laser devices, or other similar devices capable of measuring certain elongated bodies (e.g., wires and webs) at suitable sampling rates. Typically, with an optical micrometer, the micrometer itself is positioned near the pathway of the elongated conductive body and configured to measure the thickness of the elongated conductive body without actually contacting it.

In some embodiments, the thickness measurement sensor is configured to periodically measure the outside diameter of the elongated conductive body. The thickness measurement sensor can also be operatively connected to the processor, which is programmed to compare the latest measurement value of the diameter with a prior measurement value corresponding to the diameter prior to the latest coating sequence. The processor may also be programmed to calculate the thickness of the latest coating by subtracting the prior measurement value from the latest measurement value. The thickness of the coated elongated conductive body will of course progressively increase with each successive layer of coating material deposited onto the elongated conductive body. Once a determination has been made as to the layer thickness of a certain segment of the elongated conductive body, the processor is programmed to instruct the thickness measurement sensor to measure another segment of the elongated conductive body as it advances into the thickness measurement sensor. In some embodiments, the thickness measurement sensor may be set to make a thickness measurement about every 100 cm of the elongated conductive body, or less than about every 50 cm, or less than about every 25 cm, or still less than about every 10 cm, or less than about every 5 cm, or less than about every 2.5 cm, or less than about every 1 cm, or less than about every 1 mm, or even less than about every 100 microns. The measurements made by the thickness measurement sensor can be for the outer surface of the elongated conductive body, the window surface, or both. Based upon the signal transmitted from the thickness measurement sensor, the processor 160 may control certain parameters of the coating process. For example, if a particular coating thickness (e.g., thickness of the electrode layer, enzyme layer, and/or diffusion resistance layer) is measured to be less than the preselected thickness, the system may be programmed to repeat the coating process once, twice, or more times, until the preselected thickness has been achieved.

Alternatively, in other embodiments, the system may be programmed to run the coating process for a preselected number of iterations, instead of programmed to run the coating process repeatedly until a certain preselected thickness is achieved. In these embodiments, thickness control can still be achieved because of the high level of precision of thickness control provided by the system.

In some embodiments, the thickness measurement station 150 may not be configured to measure the exact thickness of the elongated conductive body. Instead, the thickness measurement station may include a vision system that is configured to detect certain surface irregularities on the elongated conductive body. Irregularities can include, but are not limited to, exposed patches that resemble an undercoating (e.g., an insulating coating underlying a conductive coating) and that indicate a section of the elongated conductive body in which coating is very thin or nonexistent. The exposed patches can show up on the vision system with a color or reflection that is different than that expected. After a surface irregularity has been detected, the coating process can be stopped. Alternatively, the process can be continued, with the section of the detected surface irregularity recorded, and the recorded section can be removed in subsequent processing.

Post-Coating Treatment Station

After the elongated conductive body has been coated with at least one layer of material, such as a conductive material, insulating material, or membrane material (e.g., materials that form the electrode, interference, enzyme, and/or diffusion resistance layers), with each layer having been determined as having the preselected thickness, the elongated conductive body can then be advanced to a post-coating treatment station, where the elongated conductive body is cleaned and further processed, for example, through an another surface treatment process (e.g., plasma treatment). In some embodiments, after singulation of the elongated conductive body into individual sensors, the ends or tips of the singulated individual sensors may have various exposed metal portions not covered by a membrane or an insulating layer. A sensor formed without a seal covering these end portions may pick up various levels of unwanted signals. Thus, in some embodiments, the exposed portions are sealed off using any of a variety of known techniques, such as, for example, by dipping, spraying, shrink tubing, or crimp wrapping an insulating, membrane, or other isolating material onto the sensor tip. In certain embodiments, in which the sensor tip is capped with a membrane material, the tip can serve as a working electrode. After the end sealing process, certain portions (e.g., the back ends) of the singulated sensors can be etched to expose a conductive material, to provide the sensors with electrical connection. Alternatively or additionally, a mechanical connector may be clamped onto the elongated conductive body's conductive surface, cutting through the membrane in the process. Thereafter, the sensors can be delivered to other stations for further processing.

After the continuous analyte sensors have been completely built, the sensors are then packaged into containers or boxes for shipping to a patient, hospital, or retailer. The containers or boxes may be formed of special materials that are capable of protecting the sensors from harsh environmental conditions.

Singulation Station

During any time of the sensor manufacturing process, the elongated conductive body can be cut for singulation into individual pieces. For example, in some embodiments, singulation can be performed before coating of conductive and/or insulating materials. In other embodiments, singulation can be performed after coating of the conductive and/or insulating materials, but before coating of membrane materials. In yet other embodiments, singulation can be performed after coating of conductive and/or insulating materials and after coating of membrane materials. Any of a variety of known cutting systems, such as a system comprising a hydraulic cutting device, for example, can be used.

Figure 11:
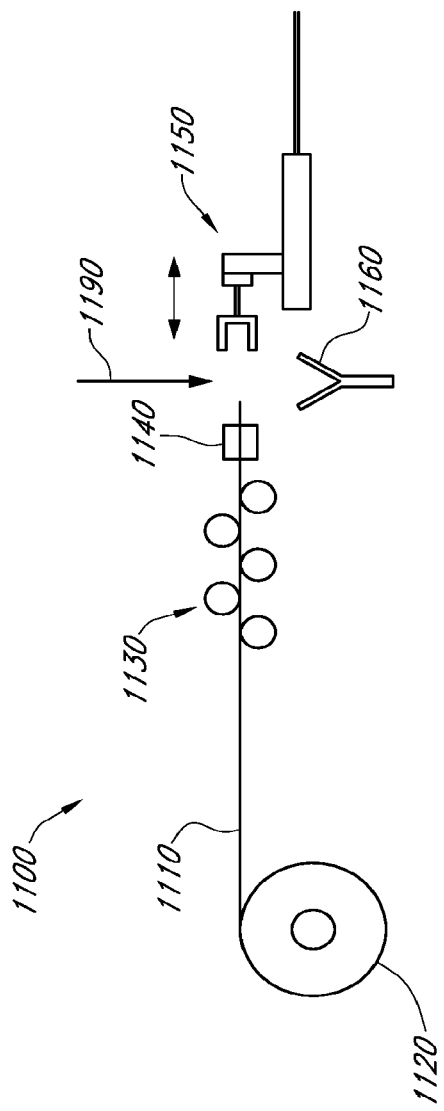
FIG. 11 illustrates one embodiment of a system that integrates etching and singulation of the elongated conductive body.

FIG. 11 illustrates one embodiment of a system 1100 that integrates etching (to remove or strip portions of a coated assembly structure) and singulation of the elongated conductive body into individual pieces. In this embodiment, the cutting system 1100 includes a supply spool 1120 which feeds an elongated conductive body 1110 into an elongated conductive body straightener 1130 (e.g., a wire straightener). The elongated conductive body 1110 is then fed into a rotating mandrel 1140, which rotates the elongated conductive body 1110. Periodically, an elongated conductive body gripping device 1150 moves forward and grasps the end of the elongated conductive body 1110 and then moves backwards to position the elongated conductive body 1110 for etching by any of the etching processes described elsewhere herein (e.g., by laser ablation 1190). Rotation of the elongated conductive body 1110 can involve a complete rotation (i.e., a rotation of 360 degrees or more), through which a portion associated with the entire circumference of the elongated conductive body 1110 is etched. Alternatively, rotation of the elongated conductive body can be partial and controlled such that only certain sections associated with the elongated conduct body's circumference is etched. After the etching process is completed, a section of the elongated conductive body 1110 is cut by a cutter 1160. The steps described are then continuously repeated. It should be understood that the system described above is merely exemplary, and some components (e.g., the mandrel 1140 or the etching mechanism) may be omitted or replaced by other components (e.g., a drying or curing mechanism).

Sensor Manufacturing Process

Figure 5:
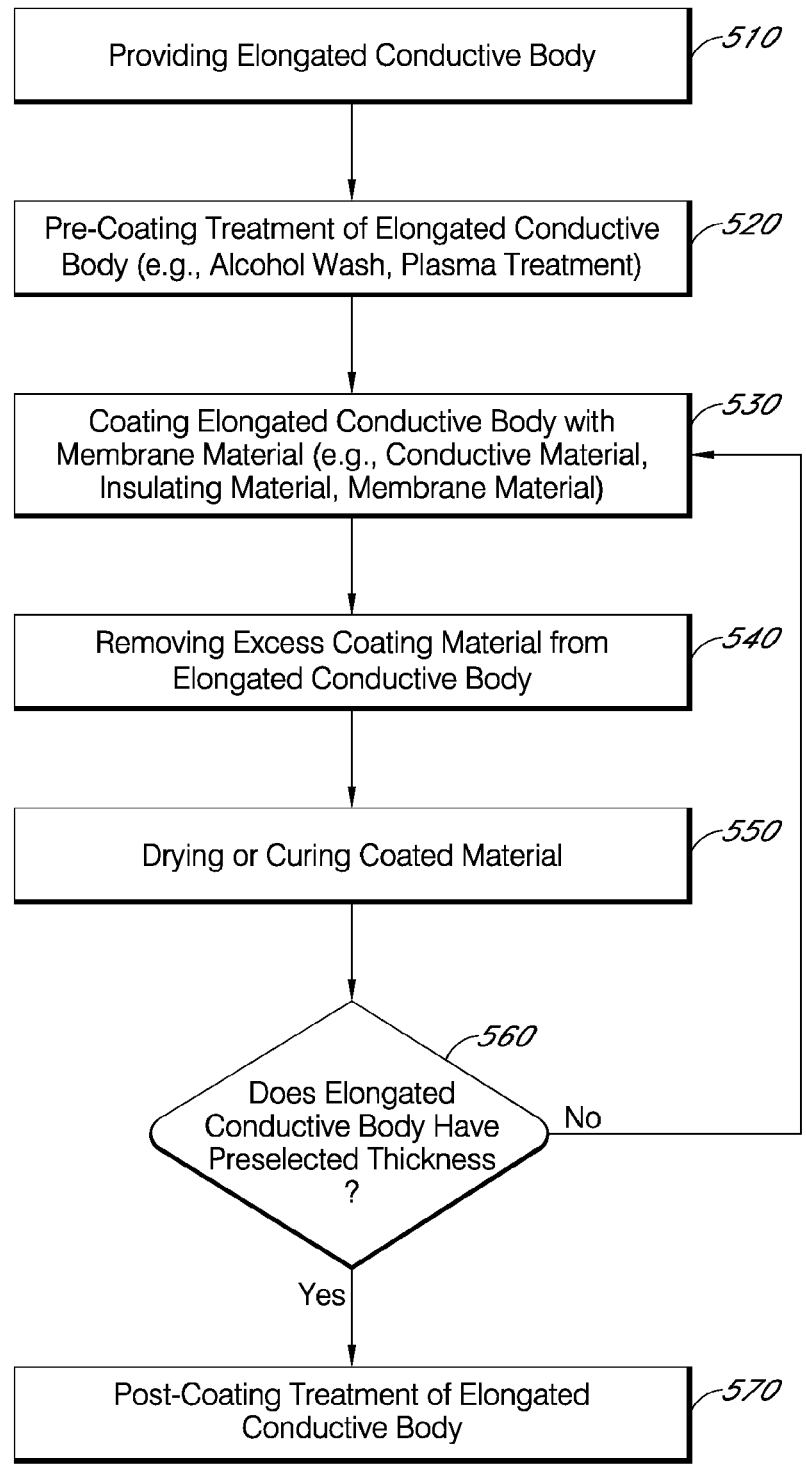
FIG. 5 is a flowchart summarizing the steps of one embodiment of a method for continuously manufacturing analyte sensors.

FIG. 5 is a flowchart summarizing the steps of one embodiment of a method for continuously manufacturing analyte sensors. In step 510, an elongated conductive body is provided. The elongated conductive body can be a bare elongated core (e.g., a metal wire), a cladded elongated core, or a bare or cladded elongated core coated with one, two, three, four, five, or more layers of material. Although not shown in FIG. 5, in some embodiments, step 510 can be preceded by one or more steps, wherein the above-described elongated conductive body (as shown in FIG. 4A) is built by coating an elongated core (e.g., a wire) with one or more layers of material (e.g., an insulating layer and a conductive layer) to form a coated assembly structure, and then removing portions of the coated assembly structure. For example, in one embodiment, the elongated core is advanced through a coating station/thickness control station/drying/curing station/thickness measurement station series/sequence, whereby it is coated with an insulating material. The series/sequence may be repeated until an insulating layer having a preselected thickness has been deposited, as measured by the thickness measurement sensor. The elongated conductive body is then advanced through a coating station/thickness control station/drying/curing station/thickness measurement station sequence, whereby it is coated with a conductive material. Again, the sequence may be repeated until a conductive layer having a preselected thickness has been deposited. After the insulating and conductive layers have been deposited onto the elongated core, the elongated conductive body can then be advanced to an etching station, where portions of the coated assembly structure is stripped or otherwise removed (e.g., to expose the electroactive surfaces of the elongated core, thereby creating window regions corresponding to electroactive surface areas).

In step 520, the elongated conductive body is advanced through a pre-coating treatment station, where it is cleaned with a solvent to remove surface contaminants. In some embodiments, an additional drying step can be provided to evaporate any residual solvents left on the surface of the elongated conductive body.

In step 530, the elongated conductive body is advanced through a coating station, where a coating solution comprising a solvent and a coating material (e.g., a material to form a conductive layer, insulating layer, or a membrane) is deposited onto the elongated conductive body. The layers that may form the membrane system are described in greater detail below. As the solvent portion of the coating solution evaporates, a solid layer of the coating material is formed on the elongated conductive body. In some embodiments, the coating solution is deposited by a meniscus coating process, whereby the elongated conductive body is advanced through a meniscus established at an opening of a coating vessel. The meniscus coating process described herein provides the system with the capability of precisely controlling the thickness and thickness profile of the coating deposited.

In step 540, the elongated conductive body is advanced through a thickness control station, where excess coating material can be removed to form on the treated surface a layer of coating having a substantially consistent thickness. In some embodiments, the coating station and the thickness control station may be integrated into one station.

In step 550, the elongated conductive body is advanced through the drying or curing station, where it may be dried under ambient conditions or heated to remove residual solvent on the surface of the elongated conductive body. In certain embodiments, at the drying or curing station, crosslinkable components of the coating material are substantially crosslinked. The curing process can be carried out by any of a variety of conventional drying techniques including, but not limited to, by UV, infrared, microwave, x-ray, gamma ray, or electron beam radiation, or by heat.

In step 560, the elongated conductive body is advanced through the thickness measurement station, where a measurement is made of the thickness of the elongated conductive body, and a signal indicative of the measurement is transmitted to the processor. The processor then compares the measured thickness with a preselected thickness. If the measured thickness is determined to be less than the preselected thickness, the system is programmed to repeat the coating process until a layer having the preselected thickness is formed.

In step 570, after being coated with multiple layers of material (e.g., insulating, conductive, electrode, interference, enzyme, and/or diffusion resistance material), with each layer having the preselected thickness, the elongated conductive body is advanced into the post-coating treatment station, where it can be cleaned and/or undergo further treatment. Thereafter, the individual sensors can be delivered to other stations for further processing.

It should be understood that the method described above is merely exemplary, and some steps may be omitted or replaced by other steps. Furthermore, although the steps of the method are described in a particular order, the various steps need not be performed sequentially or in the order described. For example, in some embodiments, an elongated conductive body is provided, as indicated by step 510. Thereafter, it undergoes processing, as indicated by steps 520, 530, 540, 550, and 560, whereby a coating forming a first layer (e.g., an insulating layer) with a preselected thickness is deposited on the elongated conductive body. The coating process (i.e., the sequence formed of steps 520, 530, 540, 550, and 560) can be repeated several times, with each passing sequence resulting in a successive layer (e.g., a second layer comprising an enzyme layer, a third layer comprising a diffusion resistance layer, etc.) with a preselected thickness being deposited onto the elongated conductive body. After the preselected layers have been deposited, the elongated conductive body can then be transferred to a station for post-coating treatment, as indicated by step 570.

To demonstrate the method described in FIG. 5, an example is provided herein describing one embodiment of coating polyurethane (an insulating material) onto the outer conductive surface of an elongated conductive body. Although the material described in this example is polyurethane, it should be understood that other insulating materials (e.g., polyethylene, polyimide, etc.) may be also be used in accordance with the method described herein.

In step 510, an elongated conductive body is provided which has an outer conductive layer formed of platinum and an inner core formed of another material (e.g., stainless steel, titanium, tantalum, glass, polymeric material, non-conductive material, etc.). In an alternative embodiment, the entire elongated conductive body may be monolithic and formed of a conductive material, such as platinum, platinum-iridium, gold, palladium, iridium, graphite, carbon, conductive polymers, and combinations thereof.

Next, in step 520 the elongated conductive body is treated (e.g., washed with alcohol or treated with plasma). In some embodiments, an adhesion promoter may be applied to the outer surface of the elongated conductive body. The adhesion promoter may be used to cause surface reaction to improve adhesion of the polyurethane to the conductive surface of the elongated conductive body, and thereby reduce the risk of delamination. The adhesion promoters, in a non-limiting embodiment, can be monomers, oligomers and/or polymers. Such materials include, but are not limited to, organometallics such as silanes, (e.g., mercapto silanes, acrylate or methacrylate functional silanes, vinyl silanes, amino silanes, epoxy silanes, isocyanate silanes, fluoro silanes, and alkyl silanes), siloxanes, titanates, zirconates, aluminates, metal containing compounds, zirconium aluminates, hydrolysates thereof and mixtures thereof. In one embodiment, silane is used as an adhesion promoter, and it is used as a component of a solution. In a further embodiment, the solution comprises from about 90% to 98% organic solvent (e.g., ethanol, tetrahydrofuran), about 1% to 5% water, and about 1 to 5% silane onto the outer surface of the elongated conductive body. The solvents may then be removed by air drying and/or by using an oven.

Thereafter, in step 530, the polyurethane is coated onto the elongated conductive body using any of the coating techniques described elsewhere herein, such as a meniscus coating method. The polyurethane coating is then dried or cured. In certain embodiments, the polyurethane may have a thickness of from about 5 microns to about 50 microns, or from about 12 microns to about 25 microns, or even from about 18 microns to about 23 microns. Excess coating materials of polyurethane are then removed by use of a die, in accordance with step 540. The cycle from step 510 to step 550 can then be repeated until a preselected thickness of the polyurethane layer has been achieved.

To further demonstrate the method described in FIG. 5, another example is provided herein. This particular example describes one embodiment of coating a platinum material onto the elongated core or an Ag/AgCl material (i.e., a conductive material) onto the polyurethane layer described in the example above. Although the materials used in this example are platinum, Ag/AgCl, and polyurethane, it should be understood that other conductive materials and insulating materials may also be used in accordance with the method described herein.

With respect to coating of Ag/AgCl onto the polyurethane, the coating material can involve an Ag/AgCl solution or paste which can be purchased from commercially available sources or alternatively prepared to have certain specified properties. Typically, an AgCl layer is consumed during a period when the Ag/AgCl electrode is used as a cathode. Accordingly, by controlling the composition, thickness, or other properties of the Ag/AgCl layer, the effective lifespan of a sensor (i.e., the period of time that it can function properly) can be controlled by the manufacturing method. The silver grain and the silver chloride grain can have any of a variety of shapes, such as a shape similar to a sphere, plate, flake, a polyhedron, or combinations thereof.

In some embodiments, the silver grain in the Ag/AgCl solution or paste can have an average particle size associated with a maximum particle dimension that is less than about 100 microns, or less than about 50 microns, or less than about 30 microns, or less than about 20 microns, or less than about 10 microns, or even less than about 5 microns. The silver chloride grain in the Ag/AgCl solution or paste can have an average particle size associated with a maximum particle dimension that is less than about 100 microns, or less than about 80 microns, or less than about 60 microns, or less than about 50 microns, or less than about 20 microns, or even less than about 10 microns. The silver grain and the silver chloride grain may be incorporated at a ratio of the silver chloride grain:silver grain of from about 0.01:1 to 2:1 by weight, and sometimes from about 0.1:1 to 1:1. The silver grains and the silver chloride grains are then mixed with a carrier (e.g., a polyurethane) to form a solution or paste. In certain embodiments, the Ag/AgCl component comprises from about 10% to about 65% by weight of the total Ag/AgCl solution or paste, or from about 20% to about 50% by weight of the total Ag/AgCl solution or paste, or even from about 23% to about 37% by weight of the total Ag/AgCl solution or paste. In some embodiments, the Ag/AgCl solution or paste has a viscosity (under ambient conditions) that is from about 1 to about 500 centipoise, or from about 10 to about 300 centipoise, or even from about 50 to about 150 centipoise.

Prior to the coating step 530, an elongated conductive body is provided in step 510. In one embodiment associated with coating of platinum onto the elongated core, the elongated conductive body is only an elongated core. In one embodiment associated with coating of Ag/AgCl onto polyurethane, the elongated conductive body has an outer conductive layer formed of platinum with an inner elongated core formed of another material (e.g., stainless steel, titanium, tantalum, polymeric material, non-conductive material, etc.). Disposed over the platinum layer is a layer of polyurethane deposited using the method described in the example above. In alternative embodiments, the entire elongated conductive body may be monolithic and formed of a conductive material, such as platinum, platinum-iridium, gold, palladium, iridium, graphite, carbon, conductive polymers, and combinations thereof.

Next, in step 520 the elongated conductive body is treated (e.g., washed with an alcohol wash, treated with plasma, or corona treatment). Similar to the example described above regarding the coating of polyurethane, an adhesion promoter may optionally be applied to the polyurethane to improve the adhesion of the polyurethane to the Ag/AgCl material being deposited or of the elongated core material (e.g., stainless steel, tantalum) to the platinum material being deposited.

Thereafter, in step 530, the platinum solution or Ag/AgCl solution or paste is coated onto the elongated conductive body using any of the coating techniques described elsewhere herein. In one embodiment, the coating chamber 360 illustrated in FIG. 3G is used to perform the coating step 530. In addition, the die 366 in the coating chamber is used to perform the step 540 of removing excess platinum, Ag/AgCl, or other material from the elongated conductive body. In one embodiment associated with coating of platinum onto the elongated core, the coated platinum layer may have a thickness of from a thickness corresponding to a layer formed from a few platinum atoms to about 200 microns, or from about 1 micron to about 10 microns, or even from about 3 microns to about 5 microns. In one embodiment associated with the coating of Ag/AgCl onto the elongated core, the coated Ag/AgCl layer can have a thickness of from about 0.5 microns to about 30 microns, or from about 1 micron to about 20 microns, or even from about 5 microns to about 15 microns. The cycle from step 510 to step 550 is then be repeated until a preselected thickness of the platinum layer or Ag/AgCl layer has been achieved. It is contemplated that the ratio of the thickness of the Ag/AgCl layer to the thickness of the polyurethane layer can be controlled, so as to allow for a certain error margin (e.g., an error margin associated with the etching process) that would not result in a defective sensor (e.g., due to a defect resulting from an etching process that cuts into a depth more than intended, thereby unintentionally exposing an electroactive surface). This ratio may be different depending on the type of etching process used, e.g., whether it is laser ablation, grit blasting, chemical etching, or some other etching method. For laser ablation, the ratio of the thickness of the Ag/AgCl layer to the thickness of the polyurethane layer can be from about 1:5 to about 1:1, or from about 1:3 to about 1:2.

Membrane System

The membrane systems described herein can be formed using the systems and methods described above, and are suitable for use with implantable sensors in contact with a biological fluid. For example, the membrane system can be utilized with sensors for measuring analyte levels in a biological fluid, such as sensors for monitoring glucose levels for individuals having diabetes. In some embodiments, the analyte-measuring sensor is a continuous sensor. A wide variety of sensor configurations are contemplated with respect to sensor placement. For example, in some embodiments, the sensor can be configured for transdermal (e.g., transcutaneous) placement, but in other embodiments the sensor can be configured for intravascular placement, subcutaneous placement, intramuscular placement, or intraosseous placement. The sensor can use any method to provide an output signal indicative of the concentration of the analyte of interest; these methods can include, for example, invasive, minimally invasive, or non-invasive sensing techniques.

Although some of the description that follows is directed at glucose-measuring devices, the membrane systems described herein are not limited to use in devices that measure or monitor glucose. Rather, these membrane systems are suitable for use in any of a variety of devices, including, for example, devices that detect and quantify other analytes present in biological fluids (e.g., cholesterol, amino acids, alcohol, galactose, and lactate), cell transplantation devices, drug delivery devices, and the like.

Figure 6B:
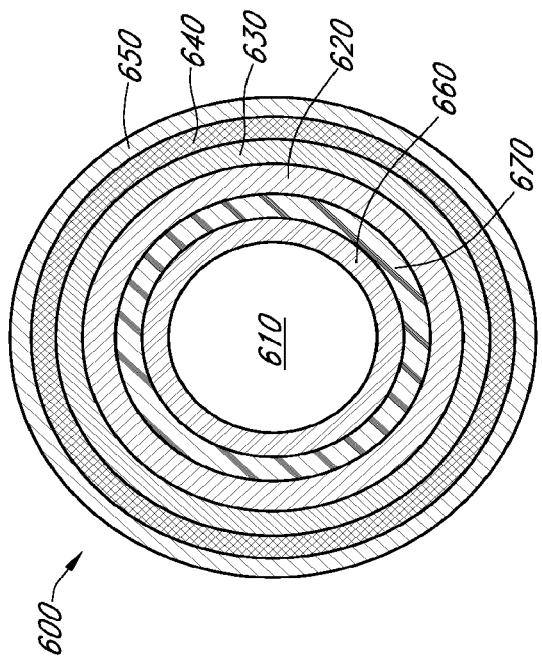
FIGS. 6A and 6B are cross-sectional views through one embodiment of the elongated conductive body of FIG. 4B on lines 6A-6A and 6B-6B, respectively.
Figure 6A:
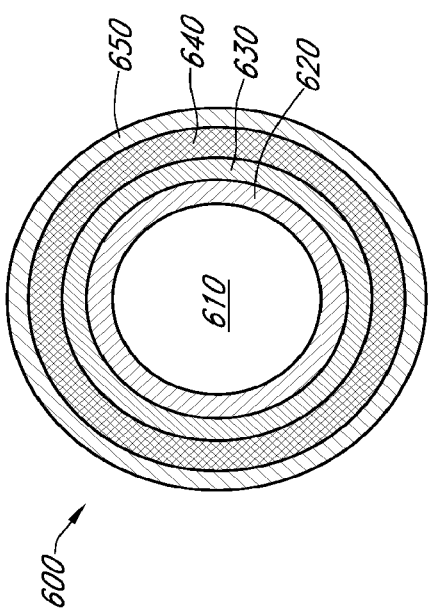

FIG. 6A is a cross-sectional view through one embodiment of the elongated conductive body of FIG. 4B on line 6A-6A, illustrating one embodiment of the membrane system 600. The cross-section illustrated in FIG. 6A corresponds to the window surface of the elongated conductive body. As described above, the window surface can correspond to a working electrode formed in part, for example, by removing a portion of the insulating material and conductive material from an electroactive surface the elongated conductive body by ablation, etching, or other like techniques. FIG. 6B is a cross-sectional view through the elongated conductive body of FIG. 4B on line 6B-6B.

In the particular embodiment shown in FIGS. 6A and 6B, the membrane system 600 comprises an electrode layer 620, interference layer 630, enzyme layer 640, and a diffusion resistance layer 650, located around the core 610 of the elongated conductive body. It should be understood that any of the layers described herein, e.g., the electrode, interference, enzyme, or diffusion resistance layer, may be omitted. In addition, it should be understood the membrane system can have any of a variety of layer arrangements, with some arrangements having more or less layers than other arrangements. For example, in some embodiments, the membrane system can comprise one interference layer, one enzyme layer, and two diffusion resistance layers, but in other embodiments, the membrane system can comprise one electrode layer, one enzyme layer, and one diffusion resistance layer. Additionally, it should be understood that although the exemplary embodiments illustrated in FIGS. 6A and 6B involve circumferentially extending membrane systems covering an elongated conductive body with a circular cross-section, the membranes described herein can be applied to any planar or non-planar surface and an elongated conductive body with any variety of cross-sectional shapes, such as oval, square, rectangular, triangular, polyhedral, star-shaped, C-shaped, T-shaped, X-shaped, Y-Shaped, irregular, or the like, for example. As shown, the portion of the elongated conductive body corresponding to the section illustrated in FIG. 6B comprises an additional conductive layer 670 and an insulating layer 660 that separates the core 610 from the conductive layer 670.

In some embodiments, one or more layers of the membrane system can be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyamides, polyimides, polystyrenes, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some embodiments, one or more layers of the membrane system are formed from a silicone polymer. In further embodiments, the silicone composition can have molecular weight of from about 50,000 to about 800,000 g/mol. It has been found that having the polymers formed with this molecular weight range facilitates the preparation of cross-linked membranes that provide the strength, tear resistance, stability, and toughness advantageous for use in vivo.

In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers can be used. For example, commercially available silicone polymer precursor compositions can be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components can be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

In some embodiments, one or more layer of the membrane system is formed from a blend of a silicone polymer and a hydrophilic polymer. By "hydrophilic polymer," it is meant that the polymer has a substantially hydrophilic domain in which aqueous substances can easily dissolve. It has been found that use of such a blend may provide high oxygen solubility and allow for the transport of glucose or other such water-soluble molecules (for example, drugs) through the membrane. In one embodiment, the hydrophilic polymer comprises both a hydrophilic domain and a partially hydrophobic domain (e.g., a copolymer), whereby the partially hydrophobic domain facilitates the blending of the hydrophilic polymer with the hydrophobic silicone polymer. In one embodiment, the hydrophobic domain is itself a polymer (i.e., a polymeric hydrophobic domain). For example, in one embodiment, the hydrophobic domain is not a simple molecular head group but is rather polymeric.

The silicone polymer for use in the silicone/hydrophilic polymer blend can be any suitable silicone polymer, include those described above. The hydrophilic polymer for use in the silicone/hydrophilic polymer blend can be any suitable hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044). In one embodiment, the hydrophilic polymer is a copolymer of poly(ethylene oxide) (PEO) and poly(propylene oxide) (PPO), such as PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof, for example. In some embodiments, the copolymers can be optionally substituted with hydroxy substituents. Commercially available examples of PEO and PPO copolymers include the PLURONIC® brand of polymers available from BASF®. Some PLURONIC® polymers are triblock copolymers of poly(ethylene oxide)-poly(propylene oxide)-poly(ethylene oxide) having the general molecular structure:

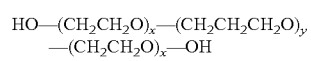

wherein the repeat units x and y vary among various PLURONIC® products. The poly(ethylene oxide) blocks act as a hydrophilic domain allowing the dissolution of aqueous agents in the polymer. The poly(propylene oxide) block acts as a hydrophobic domain facilitating the blending of the PLURONIC® polymer with a silicone polymer. In one embodiment, PLURONIC® F-127 is used having x of approximately 100 and y of approximately 65. The molecular weight of PLURONIC® F-127 is approximately 12,600 g/mol as reported by the manufacture. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The membrane system of some embodiments can comprise at least one polymer containing a surface-active group. The term "surface-active group" and "surface-active end group" as used herein are broad terms and are used in their ordinary sense, including, without limitation, surface-active oligomers or other surface-active moieties having surface-active properties, such as alkyl groups, which are inclined to migrate towards a surface of a membrane formed thereof. In some embodiments, the surface-active group-containing polymer is a surface-active end group-containing polymer. In some of these embodiments, the surface-active end group-containing polymer is a polymer having covalently bonded surface-active end groups. However, it is contemplated that other surface-active group-containing polymers may also be used and can be formed by modification of fully-reacted base polymers via the grafting of side chain structures, surface treatments or coatings applied after membrane fabrication (e.g., via surface-modifying additives), blending of a surface-modifying additive to a base polymer before membrane fabrication, immobilization of the surface-active-group-containing soft segments by physical entrainment during synthesis, or the like.

Base polymers useful for certain embodiments can include any linear or branched polymer on the backbone structure of the polymer. Suitable base polymers can include, but are not limited to, epoxies, polyolefins, polysiloxanes, polyethers, acrylics, polyesters, carbonates, and polyurethanes, wherein polyurethanes can include polyurethane copolymers such as polyether-urethane-urea, polycarbonate-urethane, polyether-urethane, silicone-polyether-urethane, silicone-polycarbonate-urethane, polyester-urethane, and the like. In some embodiments, base polymers can be selected for their bulk properties, such as, but not limited to, tensile strength, flex life, modulus, and the like. For example, polyurethanes are known to be relatively strong and to provide numerous reactive pathways, which properties may be advantageous as bulk properties for a membrane layer of the continuous sensor.

In some embodiments, a base polymer synthesized to have hydrophilic segments can be used to form at least a portion of the membrane system. For example, a linear base polymer including biocompatible segmented block polyurethane copolymers comprising hard and soft segments can be used. It is contemplated that polyisocyanates can be used for the preparation of the hard segments of the copolymer and may be aromatic or aliphatic diisocyanates. The soft segments used in the preparation of the polyurethane can be derived from a polyfunctional aliphatic polyol, a polyfunctional aliphatic or aromatic amine, or the like that can be useful for creating permeability of the analyte (e.g., glucose) therethrough, and can include, for example, polyvinyl acetate (PVA), poly(ethylene glycol) (PEG), polyacrylamide, acetates, polyethylene oxide (PEO), polyethylacrylate (PEA), polyvinylpyrrolidone (PVP), and variations thereof (e.g., PVP vinyl acetate).

Alternatively, in some embodiments, the membrane system can comprise a combination of a base polymer (e.g., polyurethane) and one or more hydrophilic polymers, such as, PVA, PEG, polyacrylamide, acetates, PEO, PEA, PVP, and variations thereof (e.g., PVP vinyl acetate), as a physical blend or admixture, wherein each polymer maintains its unique chemical nature. It is contemplated that any of a variety of combination of polymers can be used to yield a blend with desired glucose, oxygen, and interference permeability properties. For example, in some embodiments, the membrane can comprise a blend of a polycarbonate-urethane base polymer and PVP, but in other embodiments, a blend of a polyurethane, or another base polymer, and one or more hydrophilic polymers can be used instead. In some of the embodiments involving use of PVP, the PVP portion of the polymer blend can comprise from about 5% to about 50% by weight of the polymer blend, or from about 15% to 20%, or even from about 25% to 40%. It is contemplated that PVP of various molecular weights may be used. For example, in some embodiments, the molecular weight of the PVP used can be from about 25,000 daltons to about 5,000,000 daltons, or from about 50,000 daltons to about 2,000,000 daltons, or even greater than 5,000,000 daltons, for example, from 6,000,000 daltons to about 10,000,000 daltons.

Coating solutions that include at least two surface-active group-containing polymers can be made using any of the methods of forming polymer blends known in the art. In one exemplary embodiment, a solution of a polyurethane containing silicone end groups is mixed with a solution of a polyurethane containing fluorine end groups (e.g., wherein the solutions include the polymer dissolved in a suitable solvent such as acetone, ethyl alcohol, DMAC, THF, 2-butanone, and the like). The mixture can then be coated onto to the surface of the elongated conductive body using the coating process described elsewhere herein. The coating can then be cured under high temperature (e.g., about 50-150° C.), as the elongated conductive body is advanced through the drying/curing station.

Some amount of cross-linking agent can also be included in the mixture to induce cross-linking between polymer molecules. Non-limiting examples of suitable cross-linking agents include isocyanate, carbodiimide, gluteraldehyde or other aldehydes, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final film.

Described below are examples of layers that can be coated onto the elongated conductive body to form the membrane system.

Diffusion Resistance Layer

In some embodiments, the membrane system comprises a diffusion resistance layer, which may be disposed more distal to the elongated core than the other layers. A molar excess of glucose relative to the amount of oxygen exists in blood, i.e., for every free oxygen molecule in extracellular fluid, there are typically more than 100 glucose molecules present (see Updike et al., *Diabetes Care* 5:207-21(1982)). Accordingly, without a semipermeable membrane situated over the enzyme layer to control the flux of glucose and oxygen, a linear response to glucose levels can sometimes be obtained only up to about 40 mg/dL. However, in a clinical setting, a linear response to glucose levels is desirable up to at least about 500 mg/dL. The diffusion resistance layer serves to address these issues by controlling the flux of oxygen and other analytes (for example, glucose) to the underlying enzyme layer.

The diffusion resistance layer can include a semipermeable membrane that controls the flux of oxygen and glucose to the underlying enzyme layer, thereby rendering oxygen in non-rate-limiting excess. As a result, the upper limit of linearity of glucose measurement is extended to a much higher value than that which is achieved without the diffusion resistance layer. In some embodiments, the diffusion resistance layer exhibits an oxygen-to-glucose permeability ratio of approximately 200:1, but in other embodiments the oxygen-to-glucose permeability ratio can be approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion may provide sufficient excess oxygen at all reasonable glucose and oxygen concentrations found in the subcutaneous matrix (See Rhodes et al., Anal. Chem., 66:1520-1529 (1994)).

In some embodiments, the diffusion resistance layer is formed of a base polymer synthesized to include a polyurethane membrane with both hydrophilic and hydrophobic regions to control the diffusion of glucose and oxygen to an analyte sensor. A suitable hydrophobic polymer component can be a polyurethane or polyether urethane urea. Polyurethane is a polymer produced by the condensation reaction of a diisocyanate and a difunctional hydroxyl-containing material. A polyurea is a polymer produced by the condensation reaction of a diisocyanate and a difunctional amine-containing material. Diisocyanates that can be used include aliphatic diisocyanates containing from about 4 to about 8 methylene units. Diisocyanates containing cycloaliphatic moieties can also be useful in the preparation of the polymer and copolymer components of the membranes of some embodiments. The material that forms the basis of the hydrophobic matrix of the diffusion resistance layer can be any of those known in the art that is suitable for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In some embodiments, the diffusion resistance layer can comprise a blend of a base polymer (e.g., polyurethane) and one or more hydrophilic polymers (e.g., PVA, PEG, polyacrylamide, acetates, PEO, PEA, PVP, and variations thereof). It is contemplated that any of a variety of combination of polymers may be used to yield a blend with desired glucose, oxygen, and interference permeability properties. For example, in some embodiments, the diffusion resistance layer can be formed from a blend of a silicone polycarbonate-urethane base polymer and a PVP hydrophilic polymer, but in other embodiments, a blend of a polyurethane, or another base polymer, and one or more hydrophilic polymers can be used instead. In some of the embodiments involving the use of PVP, the PVP portion of the polymer blend can comprise from about 5% to about 50% by weight of the polymer blend, or from about 15% to 20%, and or from about 25% to 40%. It is contemplated that PVP of various molecular weights may be used. For example, in some embodiments, the molecular weight of the PVP used can be from about 25,000 daltons to about 5,000,000 daltons, or from about 50,000 daltons to about 2,000,000 daltons, or even greater than about 5,000,000 daltons, e.g., from 6,000,000 daltons to about 10,000,000 daltons.

In certain embodiments, the thickness of the diffusion resistance layer can be from about 0.05 microns or less to about 200 microns or more. In some of these embodiments, the thickness of the diffusion resistance layer can be from about 0.05, 0.1, 0.15, 0.2, 0.25, 0.3, 0.35, 0.4, 0.45, 0.5, 1, 1.5, 2, 2.5, 3, 3.5, 4, 6, 8 microns to about 9, 10, 11, 12, 13, 14, 15, 16, 17, 18, 19, 19.5, 20, 30, 40, 50, 60, 70, 75, 80, 85, 90, 95, or 100 microns. In some embodiments, the thickness of the diffusion resistance layer is from about 2, 2.5 or 3 microns to about 3.5, 4, 4.5, or 5 microns in the case of a transcutaneously implanted sensor or from about 20 or 25 microns to about 40 or 50 microns in the case of a wholly implanted sensor.

The description herein of the diffusion resistance layer is not intended to be applicable only to the diffusion resistance layer; rather the description can also be applicable to any other layer of the membrane system, such as the enzyme layer, electrode layer, or interference layer, for example.

Enzyme Layer

In some embodiments, the membrane system comprises an enzyme layer, which may be disposed more proximal to the elongated core than the diffusion resistance layer. The enzyme layer comprises a catalyst configured to react with an analyte. In one embodiment, the enzyme layer is an immobilized enzyme layer including glucose oxidase. In other embodiments, the enzyme layer can be impregnated with other oxidases, for example, alcohol dehydrogenase, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

In some embodiments, the catalyst (enzyme) can be impregnated or otherwise immobilized into the diffusion resistance layer such that a separate enzyme layer is not required (e.g., wherein a unitary layer is provided including the functionality of the diffusion resistance layer and enzyme layer). In some embodiments, the enzyme layer is formed from a polyurethane, for example, aqueous dispersions of colloidal polyurethane polymers including the enzyme.

In some embodiments, the thickness of the enzyme layer can be from about 0.01, 0.05, 0.6, 0.7, or 0.8 microns to about 1, 1.2, 1.4, 1.5, 1.6, 1.8, 2, 2.1, 2.2, 2.5, 3, 4, 5, 10, 20, 30 40, 50, 60, 70, 80, 90, or 100 microns. In some embodiments, the thickness of the enzyme layer is from about 0.05, 0.1, 0.15, 0.2, 0.25, 0.3, 0.35, 0.4, 0.45, 0.5, 1, 1.5, 2, 2.5, 3, 4, or 5 microns to about 6, 7, 8, 9, 10, 11, 12, 13, 14, 15, 16, 17, 18, 19, 19.5, 20, 25, or 30 microns, or from about 2, 2.5, or 3 microns to about 3.5, 4, 4.5, or 5 microns in the case of a transcutaneously implanted sensor or from about 6, 7, or 8 microns to about 9, 10, 11, or 12 microns in the case of a wholly implanted sensor.

It should be understood that the description herein of the enzyme layer is not intended to be applicable only to the enzyme layer; rather the description can also be applicable to any other layer of the membrane system, such as the diffusion resistance layer, electrode layer, or interference layer, for example.

Electrode Layer

In some embodiments, the membrane system comprises an electrode layer, which may be disposed more proximal to the elongated core than any other layer. The electrode layer is configured to facilitate electrochemical reaction on the electroactive surface and can include a semipermeable coating for maintaining hydrophilicity at the electrochemically reactive surfaces of the sensor interface. In other embodiments, the functionality of the electrode layer can be incorporated into the diffusion resistance layer, so as to provide a unitary layer that includes the functionality of the diffusion resistance layer, enzyme layer, and/or electrode layer.

The electrode layer can enhance the stability of an adjacent layer by protecting and supporting the material that makes up the adjacent layer. The electrode layer may also assist in stabilizing the operation of the device by overcoming electrode start-up problems and drifting problems caused by inadequate electrolyte. The buffered electrolyte solution contained in the electrode layer may also protect against pH-mediated damage that can result from the formation of a large pH gradient between the substantially hydrophobic interference layer and the electrodes due to the electrochemical activity of the electrodes.

In one embodiment, the electrode domain includes hydrophilic polymer film (e.g., a flexible, water-swellable, hydrogel) having a "dry film" thickness of from about 0.05 microns or less to about 20 microns or more, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or even from about 3, 2.5, 2, or 1 microns, or less, to about 3.5, 4, 4.5, or 5 microns or more. "Dry film" thickness refers to the thickness of a cured film cast from a coating formulation by standard coating techniques.

In certain embodiments, the electrode layer can be formed of a curable mixture of a urethane polymer and a hydrophilic polymer. In some of these embodiments, coatings are formed of a polyurethane polymer having anionic carboxylate functional groups and non-ionic hydrophilic polyether segments, wherein the polyurethane polymer undergoes aggregation with a water-soluble carbodiimide (e.g., 1-ethyl-3-(3-dimethylaminopropyl)carbodiimide (EDC)) in the presence of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as W-121 and W-123; and a polyester-polyurethane backbone containing carboxylate groups, identified as W-110-2. In some embodiments, BAYBOND® 123, an aqueous anionic dispersion of an aliphatic polycarbonate urethane polymer sold as a 35 weight percent solution in water and co-solvent N-methyl-2-pyrrolidone, can be used.

In some embodiments, the electrode layer is formed from a hydrophilic polymer that renders the electrode layer substantially more hydrophilic than an overlying layer (e.g., interference layer, enzyme layer). Such hydrophilic polymers can include, a polyamide, a polylactone, a polyimide, a polylactam, a functionalized polyamide, a functionalized polylactone, a functionalized polyimide, a functionalized polylactam or combinations thereof, for example.

In some embodiments, the electrode layer is formed primarily from a hydrophilic polymer, and in some of these embodiments, the electrode layer is formed substantially from PVP. PVP is a hydrophilic water-soluble polymer and is available commercially in a range of viscosity grades and average molecular weights ranging from about 18,000 to about 500,000, under the PVP K® homopolymer series by BASF Wyandotte and by GAF Corporation. In certain embodiments, a PVP homopolymer having an average molecular weight of about 360,000 identified as PVP-K90 (BASF Wyandotte) can be used to form the electrode layer. Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

In certain embodiments, the electrode layer is formed entirely from a hydrophilic polymer. Useful hydrophilic polymers contemplated include, but are not limited to, poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers can be used in some embodiments.

It is contemplated that in certain embodiments, the hydrophilic polymer used may not be crosslinked, but in other embodiments, crosslinking may be used and achieved by any of a variety of methods, for example, by adding a crosslinking agent. In some embodiments, a polyurethane polymer can be crosslinked in the presence of PVP by preparing a premix of the polymers and adding a crosslinking agent just prior to the production of the membrane. Suitable cross-linking agents contemplated include, but are not limited to, carbodiimides (e.g., 1-ethyl-3-(3-dimethylaminopropyl) carbodiimide hydrochloride, UCARLNK®. XL-25 (Union Carbide)), epoxides and melamine/formaldehyde resins. Alternatively, it is also contemplated that crosslinking can be achieved by irradiation at a wavelength sufficient to promote crosslinking between the hydrophilic polymer molecules, which is believed to create a more tortuous diffusion path through the layer.

The flexibility and hardness of the coating can be varied as desired by varying the dry weight solids of the components in the coating formulation. The term "dry weight solids" as used herein is a broad term, and is to be given its ordinary and customary meaning to a person of ordinary skill in the art (and is not to be limited to a special or customized meaning), and refers without limitation to the dry weight percent based on the total coating composition after the time the crosslinker is included. In one embodiment, a coating formulation can contain from about 6 to about 20 dry weight percent, or about 8 dry weight percent, PVP; from about 3 to about 10 dry weight percent, or about 5 dry weight percent cross-linking agent; and from about 70 to about 91 weight percent, or about 87 weight percent of a polyurethane polymer, such as a polycarbonate-polyurethane polymer, for example. The reaction product of such a coating formulation is referred to herein as a water-swellable cross-linked matrix of polyurethane and PVP.

In some embodiments, underlying the electrode layer is an electrolyte phase that when hydrated is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrode layer. It is contemplated that certain embodiments can use any suitable electrolyte solution, including standard, commercially available solutions. Generally, the electrolyte phase can have the same osmotic pressure or a lower osmotic pressure than the sample being analyzed. In some embodiments, the electrolyte phase comprises normal saline.

It should be understood that the description herein of the electrode layer is not intended to be applicable only to the electrode layer; rather the description can also be applicable to any other layer of the membrane system, such as the diffusion resistance layer, enzyme layer, or interference layer, for example.

Interference Layer

In some embodiments, the membrane system may comprise an interference layer configured to substantially reduce the permeation of one or more interferents into the electrochemically reactive surfaces. The interference layer may be configured to be substantially less permeable to one or more of the interferents than to the measured species. It is also contemplated that in some embodiments, where interferent blocking may be provided by the diffusion resistance layer (e.g., via a surface-active group-containing polymer of the diffusion resistance layer), a separate interference layer may not be used.

In some embodiments, the interference layer is formed from a silicone-containing polymer, such as a polyurethane containing silicone, or a silicone polymer. While not wishing to be bound by theory, it is believed that, in order for an enzyme-based glucose sensor to function properly, glucose would not have to permeate the interference layer, where the interference layer is located more proximal to the electroactive surfaces than the enzyme layer. Accordingly, in some embodiments, a silicone-containing interference layer, comprising a greater percentage of silicone by weight than the diffusion resistance layer, can be used without substantially affecting glucose concentration measurements. For example, in some embodiments, the silicone-containing interference layer can comprise a polymer with a high percentage of silicone (e.g., from about 25%, 30%, 35%, 40%, 45%, or 50% to about 60%, 70%, 80%, 90% or 95%).

In one embodiment, the interference layer can include ionic components incorporated into a polymeric matrix to reduce the permeability of the interference layer to ionic interferents having the same charge as the ionic components. In another embodiment, the interference layer can include a catalyst (for example, peroxidase) for catalyzing a reaction that removes interferents.

In certain embodiments, the interference layer can include a thin membrane that is designed to limit diffusion of certain species, for example, those greater than 34 kD in molecular weight. In these embodiments, the interference layer permits certain substances (for example, hydrogen peroxide) that are to be measured by the electrodes to pass through, and prevents passage of other substances, such as potentially interfering substances. In one embodiment, the interference layer is constructed of polyurethane. In an alternative embodiment, the interference layer comprises a high oxygen soluble polymer, such as silicone.

In some embodiments, the interference layer is formed from one or more cellulosic derivatives. In general, cellulosic derivatives can include polymers such as cellulose acetate, cellulose acetate butyrate, 2-hydroxyethyl cellulose, cellulose acetate phthalate, cellulose acetate propionate, cellulose acetate trimellitate, or blends and combinations thereof.

In some alternative embodiments, other polymer types that can be utilized as a base material for the interference layer include polyurethanes, polymers having pendant ionic groups, and polymers having controlled pore size, for example. In one such alternative embodiment, the interference layer includes a thin, hydrophobic membrane that is non-swellable and restricts diffusion of low molecular weight species. The interference layer is permeable to relatively low molecular weight substances, such as hydrogen peroxide, but restricts the passage of higher molecular weight substances, including glucose and ascorbic acid.

It is contemplated that in some embodiments, the thickness of the interference layer can be from about 0.01 microns or less to about 20 microns or more. In some of these embodiments, the thickness of the interference layer can be from about 0.01, 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. In some of these embodiments, the thickness of the interference layer can be from about 0.2, 0.4, 0.5, or 0.6, microns to about 0.8, 0.9, 1, 1.5, 2, 3, or 4 microns.

It should be understood that the description herein of the interference layer is not intended to be applicable only to the interference layer; rather the description can also be applicable to any other layer of the membrane system, such as the diffusion resistance layer, enzyme layer, or electrode layer, for example.

Therapeutic Agents

A variety of therapeutic (bioactive) agents can be used with the analyte sensor system. In some embodiments, the therapeutic agent is an anticoagulant for preventing coagulation within or on the sensor. In some embodiments, the therapeutic agent is an antimicrobial, such as but not limited to an antibiotic or antifungal compound. In some embodiments, the therapeutic agent is an antiseptic and/or disinfectant. Therapeutic agents can be used alone or in combination of two or more agents. The therapeutic agents can be dispersed throughout the material of the sensor. In some embodiments, the membrane system can include a therapeutic agent that is incorporated into a portion of the membrane system, or which is incorporated into the device and adapted to diffuse through the membrane.

There are a variety of systems and methods by which the therapeutic agent can be incorporated into the membrane system. In some embodiments, the therapeutic agent is incorporated at the time of manufacture of the membrane system. For example, the therapeutic agent can be blended prior to curing the membrane system. In other embodiments, the therapeutic agent is incorporated subsequent to membrane system manufacture, for example, by coating, imbibing, solvent-casting, or sorption of the bioactive agent into the membrane system. Although the therapeutic agent can be incorporated into the membrane system, in some embodiments the therapeutic agent can be administered concurrently with, prior to, or after insertion of the device intravascularly, for example, by oral administration, or locally, for example, by subcutaneous injection near the implantation site. In some embodiments, a combination of therapeutic agent incorporated in the membrane system and therapeutic agent administration locally and/or systemically can be used.

To the extent publications and patents or patent applications incorporated by reference herein contradict the disclosure contained in the specification, the specification is intended to supersede and/or take precedence over any such contradictory material.

Terms and phrases used in this document, and variations thereof, unless otherwise expressly stated, should be construed as open ended as opposed to limiting. As examples of the foregoing, the term "including" should be read to mean "including, without limitation" or the like; the term "comprising" as used herein is synonymous with "including", "containing", or "characterized by", and is inclusive or open-ended and does not exclude additional, unrecited elements or method steps; the term "example" is used to provide exemplary instances of the item in discussion, not an exhaustive or limiting list thereof; adjectives such as "known", "conventional", "normal", "standard", and terms of similar meaning should not be construed as limiting the item described to a given time period or to an item available as of a given time, but instead should be read to encompass known, normal, or standard technologies that may be available or known now or at any time in the future; and use of terms like "preferred", "desired", or "desirable", and terms of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. In addition, as used in this application, the articles "a" and "an" should be construed as referring to one or more than one (i.e., to at least one) of the grammatical objects of the article. By way of example, "an element" means one element or more than one element.

The presence in some instances of broadening words and phrases such as "one or more", "at least", "but not limited to", or other like phrases should not be read to mean that the narrower case is intended or required in instances where such broadening phrases may be absent.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method, comprising:
   removing, using at least one laser, a first portion of a first conductive layer of an elongated conductive body associated with a transcutaneous analyte sensor, the elongated body comprising:
   an insulating layer;
   a second conductive layer, the insulating layer separating the first conductive layer and the second conductive layer; and
   removing a first portion of the insulating layer to expose at least one electroactive surface of the second conductive layer.

2. The method of claim 1, wherein removing the first portion of the insulating layer comprises removing, using the at least one laser, the first portion of the insulating layer using the at least one laser.

3. The method of claim 2, wherein removing, using the at least one laser, the first portion of the first conductive layer and removing, using the at least one laser, the first portion of the insulating layer comprises pulsing the at least one laser.

4. The method of claim 1, wherein the at least one laser is a first laser and wherein removing the first portion of the insulating layer comprises the first portion of the insulating layer using a second laser.

5. The method of claim 1, wherein the elongated body has a longitudinal axis, and the first portion of the first conductive layer has a first length along the longitudinal axis, and the first portion of the insulating layer has a second length along the longitudinal axis, wherein the first length is greater than the second length.

6. The method of claim 1, wherein the at least one laser has a wavelength from about 100 nm to about 800 nm.

7. The method of claim 6, wherein the at least one laser has a wavelength from about 300 nm to about 800 nm.

8. The method of claim 1, wherein removing the first portion of the first conductive layer comprises removing a depth of the first conductive layer from about 0.5 microns to about 10 microns.

9. The method of claim 1, wherein removing the first portion of the insulating layer comprises removing a depth of the insulating layer from about 0.5 microns to about 10 microns.

10. The method of claim 1, wherein removing the first portion of the first conductive layer and/or removing the first portion of the insulating layer includes removing material in a preselected pattern.

11. The method of claim 10, wherein the preselected pattern includes a plurality of spacings from about 5 mm to about 50 mm.

12. The method of claim 1, wherein the at least one laser is a first laser, and wherein removing the first portion of the first conductive layer and/or removing the first portion of the insulating layer the method further comprises a second laser distributed around a perimeter of the elongated conductive body.

13. The method of claim 12, wherein the first laser and second laser are turned on sequentially or simultaneously to remove material in a preselected pattern.

14. The method of claim 1, wherein the elongated conductive body has a longitudinal axis, and wherein removing the first portion of the first conductive layer and/or removing the first portion of the insulating layer, further comprises:
   rotating the elongated body about the longitudinal axis for a predetermined number of revolutions over time to remove, using the at least one laser, the first portion of the first conductive layer and/or to remove, using the at least one laser, the first portion of the insulating layer.

15. The method of claim 14, wherein the predetermined number of revolutions over time is from about 10 revolutions per minute to about 60 revolutions per minute.

16. A method of material removal, comprising:
   removing, using at least one laser, a first portion of a first conductive layer of an elongated conductive body associated with a transcutaneous analyte sensor, the elongated body comprising:
   a second conductive layer;
   a first insulating layer positioned between the first conductive layer and the second conductive layer;
   a third conductive layer;
   a second insulating layer positioned between the second conductive layer and the third conductive layer; and
   removing, using the at least one laser, a first portion of the first insulating layer to expose at least one electroactive surface of the second conductive layer.

17. The method of claim 16, wherein the elongated conductive body has a longitudinal axis, and the first portion of the first conductive layer comprises a first length along the longitudinal axis, and the first portion of the first insulating layer comprises a second length along the longitudinal axis, wherein the first length is greater than the second length.

18. The method of claim 16, further comprising:
   removing, using the at least one laser, a second portion of the first conductive layer;
   removing, using the at least one laser, a second portion of the first insulating layer;
   removing, using the at least one laser, a first portion of the second conductive layer; and
   removing, using the at least one laser, a first portion of the second insulating layer to expose at least one electroactive surface of the third conductive layer.

19. The method of claim 18, wherein the elongated conductive body has a longitudinal axis, and the first portion of the second conductive layer comprises a first length along the longitudinal axis, and the first portion of the second insulative layer comprises a second length along the longitudinal axis, wherein the first length is greater than the second length.

* * * * *